US008153100B2

(12) United States Patent
McBride et al.

(10) Patent No.: US 8,153,100 B2
(45) Date of Patent: *Apr. 10, 2012

(54) METHODS AND COMPOSITIONS FOR F-18 LABELING OF PROTEINS, PEPTIDES AND OTHER MOLECULES

(75) Inventors: William J. McBride, Boonton, NJ (US); Christopher A. D'Souza, Suffern, NY (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 320 days.

This patent is subject to a terminal disclaimer.

(21) Appl. No.: 12/433,212

(22) Filed: Apr. 30, 2009

(65) Prior Publication Data

US 2009/0246130 A1  Oct. 1, 2009

Related U.S. Application Data

(63) Continuation-in-part of application No. 12/343,655, filed on Dec. 24, 2008, now Pat. No. 7,993,626, which is a continuation-in-part of application No. 12/112,289, filed on Apr. 30, 2008, now Pat. No. 7,563,433, which is a continuation-in-part of application No. 11/960,262, filed on Dec. 19, 2007, now Pat. No. 7,597,876.

(60) Provisional application No. 60/884,521, filed on Jan. 11, 2007.

(51) Int. Cl.
*A61K 51/00* (2006.01)
*A61M 36/14* (2006.01)

(52) U.S. Cl. ............... 424/1.89; 424/1.11; 424/1.65; 424/1.69; 424/1.81; 424/1.85

(58) Field of Classification Search .......... 424/1.11, 424/1.65, 1.59, 1.73, 1.81, 1.85, 1.89, 9.1, 424/9.3, 9.4, 9.6, 9.7, 9.8, 9.5, 1.49, 1.53; 534/7, 10–16; 530/300, 317, 333, 338, 344, 530/350; 514/1, 1.11

See application file for complete search history.

(56) References Cited

U.S. PATENT DOCUMENTS

| 5,256,395 | A | 10/1993 | Barbet et al. | |
|---|---|---|---|---|
| 5,446,147 | A | 8/1995 | Kung et al. | |
| 5,686,116 | A * | 11/1997 | Bockman et al. | 424/650 |
| 6,056,939 | A | 5/2000 | Desreux et al. | |
| 6,207,858 | B1 | 3/2001 | Chinn et al. | |
| 6,605,615 | B2 | 8/2003 | Medina et al. | |
| 6,838,073 | B1 | 1/2005 | Collins et al. | |
| 6,953,567 | B2 | 10/2005 | Griffiths et al. | |
| 7,011,816 | B2 | 3/2006 | Griffiths et al. | |
| 7,081,452 | B2 | 7/2006 | Brechbiel et al. | |
| 7,163,935 | B2 | 1/2007 | Brechbiel et al. | |
| 7,563,433 | B2 * | 7/2009 | McBride et al. | 424/1.89 |
| 7,597,876 | B2 * | 10/2009 | McBride et al. | 424/1.89 |
| 2002/0006379 | A1 * | 1/2002 | Hansen et al. | 424/1.49 |
| 2003/0064523 | A1 | 4/2003 | Popov et al. | |
| 2005/0136001 | A1 | 6/2005 | McBride et al. | |
| 2006/0140858 | A1 | 6/2006 | Goldenberg et al. | |
| 2006/0228300 | A1 | 10/2006 | Chang et al. | |
| 2008/0027220 | A1 | 1/2008 | Stossel et al. | |
| 2008/0038191 | A1 * | 2/2008 | Perrin et al. | 424/1.45 |
| 2008/0089838 | A1 | 4/2008 | Hansen et al. | |
| 2008/0170989 | A1 | 7/2008 | McBride et al. | |

FOREIGN PATENT DOCUMENTS

| WO | 2007027385 | 3/2007 |
|---|---|---|
| WO | 2008088648 | 7/2008 |

OTHER PUBLICATIONS

Murata et al., "Formation of the Stable Myosin-ADP-Aluminum Fluoride and Myosin-ADP-Beryllium Fluoride Complexes and Their Analysis Using 19F NMR", J. Biol. Chem. 268(10):7093-7100 (1993).
International Search Report for PCT/US09/42333, filed Apr. 30, 2009, date of mailing Nov. 13, 2009.
Cai et al. "Chemistry with [18F]Fluoride Ion" Eur. J. Org. Chem. 2008, pp. 2853-2873.
Clark et al. "The Preparation of Fluorine-18 Labelled Compounds Using a Recirculatory Neon Target" Radiochem. Radioanal. Letters 14(2):101-108 (1973).
Imahori et al. "Fluorine-18-Labeled Fluoroboronophenylalanine PET in Patients with Glioma" J Nucl Med 1998; 39:325-333.
Karacay et al. "18F labeling of a peptide for PET imaging of receptor-expressing tumors" Abstract # 1567, 2009 SNM Annual Meeting Scientific Abstracts 50(Suppl. 2), p. 318P, May 2009.
Mamat et al. "Recent Applications of Click Chemistry for the Synthesis of Radiotracers for Molecular Imaging" Mini-Reviews in Organic Chemistry, 2009, vol. 6, pp. 21-34.
Marik et al. "Click for PET: rapid preparation of [18F]fluoropeptides using CuI catalyzed 1,3-dipolar cycloaddition" Tetrahedron Letters 47 (2006) 6681-6684.
McBride et al. "A new method of labeling peptides and proteins with F-18 via a metal ligand" Abstract #384, J Nucl Med. 2008; 49 (Supplement 1):97P.
McBride et al. "A new method of labeling peptides and proteins with F-18 via a metal ligand", PowerPoint Presentation, 55th SNM Annual Meeting, New Orleans, LA, Jun. 17, 2008.

(Continued)

*Primary Examiner* — D L Jones

(74) *Attorney, Agent, or Firm* — Richard A. Nakashima

(57) ABSTRACT

The present application discloses compositions and methods of synthesis and use of $^{18}F$ or $^{19}F$ labeled molecules of use in PET or MRI imaging. The labeled molecules may be peptides or proteins, although other types of molecules may be labeled. Preferably, the $^{18}F$ or $^{19}F$ is conjugated to a targeting molecule by formation of a metal complex and binding of the $^{18}F$- or $^{19}F$-metal complex to a chelating moiety. Alternatively, the metal may first be conjugated to the chelating group and subsequently the $^{18}F$ or $^{19}F$ bound to the metal. In other embodiments, the $^{18}F$ or $^{19}F$ labeled moiety may comprise a targetable construct used in combination with a bispecific antibody to target a disease-associated antigen. The $^{18}F$ or $^{19}F$ labeled targetable construct peptides are stable in serum at 37° C. for a sufficient time to perform PET or MRI imaging.

27 Claims, 20 Drawing Sheets

OTHER PUBLICATIONS

McBride et al. "A New Method of Labeling Peptides with F-18 Via a Metal Ligand", Abstract #04, Cancer Biother Radiopharm Aug. 2008; 23(4): 514.

McBride et al. "A New Method of Labeling Peptides with F-18 Via a Metal Ligand" PowerPoint Presentation, 19th Winter Fluorine Conference, St. Pete Beach, FL, Jan. 13, 2009.

McBride et al. "A New Method of Labeling Peptides with F-18 Via a Metal Ligand" Abstract #68, 19th Winter Fluorine Conference (Jan. 11-16, 2009) Abstract Book, p. 32.

McBride et al. "A novel method of radiolabeling peptides with aluminium-fluoride-18 (AlF-18) using various NOTA derivatives" Abstract # 202, 2009 SNM Annual Meeting Scientific Abstracts 50(Suppl. 2), pp. 52P-53P, May 2009.

Miller et al. "Synthesis of 11C, 18F, 15O, and 13N Radiolabels for Positron Emission Tomography" Angew. Chem. Int. Ed. 2008, vol. 47, pp. 8998-9033.

Schirrmacher et al. "Recent Developments and Trends in 18F-Radiochemistry: Syntheses and Applications" Mini-Reveiws in Organic Chemistry, 2007, vol. 4, pp. 317-329.

Schoffelen et al. "Pretargeted immunoPET for imaging colorectal cancer in a mouse model" Abstract # 381, 2009 NM Annual Meeting Scientific Abstracts 50(Suppl. 2), pp. 100P, May 2009.

Ting et al. "Toward [18F]-Labeled Aryltrifluoroborate Radiotracers: In Vivo Positron Emission Tomography Imaging of Stable Aryltrifluoroborate Clearance in Mice" J. Am. Chem. Soc. 2008, 130, 12045-12055.

Ting et al. "Arylfruoroborates and Alkylfluorosilicates as Potential PET Imaging Agents: High-Yielding Aqueous Biomolecular 18F-Labeling" J. Am. Chem. Soc. 2005, 127, 13094-13095.

Wagner, Henry N. "Advancing a Molecular Theory of Disease", J Nulc Med 49(8):15N-34N. (2008).

Wester et al. "Fluorine-18 Labeling of Peptides and Proteins", Review, Ernst Schering Res. Found. Workshop 62:79-111 (2007).

* cited by examiner

Synthesis of tetra *tert*-butyl *C*-NETA-succinyl

**Detailed Synthesis of tetra *tert*-butyl *C*-NETA-succinyl**

Synthesis of Bis-t-butyl NOTA

Synthesis of tetra *tert*-butyl *L*-NETA

6
S-NETA

(A)

(B)

(A)

(B)

(C)

F-18

Ga-68

SEQUENCE LISTING

<160> NUMBER OF SEQ ID NOS: 22

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Tyr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Tyr Lys Lys
1

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
                20                  25                  30

Ala Val Glu Tyr Phe Thr Arg Leu Arg Glu Ala Arg Ala
                35                  40                  45

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ile Glu Tyr Leu Ala Lys Gln Ile Val Asp Asn Ala Ile Gln Gln
1               5                   10                  15

Ala

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Gly Gln Ile Glu Tyr Leu Ala Lys Gln Ile Val Asp Asn Ala Ile
1               5                   10                  15

Gln Gln Ala Gly Cys
                20

<210> SEQ ID NO 7
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Ser Gly Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
                20                  25                  30

Arg Gln Gln Pro Pro Asp Leu Val Glu Phe Ala Val Glu Tyr Phe Thr
                35                  40                  45

Arg Leu Arg Glu Ala Arg Ala
        50                  55

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
```

```
                            20                  25

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Gly Gly Cys Gly
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp Tyr Ala Ile His Gln
1               5                   10                  15

Ala

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ile Glu Tyr Lys Ala Lys Gln Ile Val Asp His Ala Ile His Gln
1               5                   10                  15

Ala

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ile Glu Tyr His Ala Lys Gln Ile Val Asp His Ala Ile His Gln
1               5                   10                  15

Ala

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Gln Ile Glu Tyr Val Ala Lys Gln Ile Val Asp His Ala Ile His Gln
1               5                   10                  15

Ala

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Glu Gln Tyr Ala Asn Gln Leu Ala Asp Gln Ile Ile Lys Glu Ala
1               5                   10                  15

Thr Glu

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Glu Glu Leu Ala Trp Lys Ile Ala Lys Met Ile Trp Ser Asp Val
1               5                   10                  15

Phe Gln Gln Cys
            20

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25
```

```
<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Trp Val Trp Ala Val Gly His Leu Met
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser Gly Gly Gly Gly Ser
1               5                   10
```

US 8,153,100 B2

METHODS AND COMPOSITIONS FOR F-18 LABELING OF PROTEINS, PEPTIDES AND OTHER MOLECULES

RELATED APPLICATIONS

This application is a continuation-in-part of U.S. patent application Ser. No. 12/343,655, filed Dec. 24, 2008, which was a continuation-in-part of U.S. patent application Ser. No. 12/112,289, filed Apr. 30, 2008, which was a continuation-in-part of U.S. patent application Ser. No. 11/960,262, filed Dec. 19, 2007, which claimed the benefit under 35 U.S.C. §119(e) of Provisional U.S. Patent Application No. 60/884,521, filed Jan. 11, 2007, each of which is incorporated herein by reference in its entirety.

FIELD

In certain embodiments, the present invention concerns a simple method of labeling peptides or other molecules with $^{18}$F, which are of use for in vivo imaging. Preferably, the $^{18}$F is attached as a conjugate [complex] with aluminum or another metal via a chelating moiety, which may be covalently linked to a protein, peptide or other molecule. The preferred specific activity of the $^{18}$F-labeled peptide/molecule would be about 500 to 1,000, more preferably 1,000 to 2,000, more preferably 1,000 to 5,000 Ci/mmol at the time of administration to the patient. Specific activities that are in the range of 100 to tens of thousands of Ci/mmol would also be of use. Although higher specific activities are preferred for certain imaging applications, in other alternative embodiments a lower specific activity of a metal-$^{18}$F complex with NOTA (1,4,7-triazacyclononane-1,4,7-triacetic acid) or another chelating moiety could be of use, for example, as a renal flow imaging agent or for heart and brain imaging agents to image blood flow. Preferably, $^{18}$F labeling is accomplished without need for a purification step to separate unlabeled from labeled peptide/molecule. More preferably, $^{18}$F-labeled peptides or other molecules are stable under in vivo conditions, such as in human serum, for at least several hours. In the most preferred embodiment, the $^{18}$F-labeled molecule may be prepared in a form suitable for imaging studies in one hour or less. Using the disclosed methods, labeling of molecules may be accomplished in as little as 5 minutes. The $^{18}$F— labeled molecules are of use, for example, in PET imaging techniques. In alternative embodiments, the labeling methods may be used with other fluorine isotopes such as $^{19}$F, for example for NMR imaging techniques.

BACKGROUND

Positron Emission Tomography (PET) has become one of the most prominent functional imaging modalities in diagnostic medicine, with very high sensitivity (fmoles), high resolution (4-10 mm) and tissue accretion that can be adequately quantitated (Volkow et al., 1988, Am. J. Physiol. Imaging 3:142). Although [$^{18}$F]2-deoxy-2-fluoro-D-glucose ([$^{18}$F]FDG) is the most widely used functional imaging agent in oncology (Fletcher et al., 2008, J. Nucl. Med. 49:480), there is a keen interest in developing other labeled compounds for functional imaging to complement and augment anatomic imaging methods (Torigian et al., 2007, CA Cancer J. Clin. 57:206), especially with the hybrid PET/computed tomography systems currently in use. Thus, there is a need to have facile methods of conjugating positron-emitting radionuclides to various molecules of biological and medical interest.

Peptides or other small molecules can be labeled with the positron emitters $^{18}$F, $^{64}$Cu, $^{11}$C, $^{66}$Ga, $^{68}$Ga, $^{76}$Br, $^{94m}$Tc, $^{86}$Y, and $^{124}$I to name a few. The positron emitted from the nucleus of the isotope is ejected with different energies depending on the isotope used. When the positron reacts with an electron two 511 keV gamma rays are emitted in opposite directions. The energy of the ejected positron controls the average distance that a positron travels before it is annihilated by hitting an electron. The higher the ejection energy the further the positron travels before the collision with an electron. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized.

The half-life of the isotope is also important, since the half-life must be long enough to attach the isotope to a targeting molecule, analyze the product, inject it into the patient, and allow the product to localize, clear from non-target tissues and then image. If the half-life is too long the specific activity may not be high enough to obtain enough photons for a clear image and if it is too short the time needed for manufacturing, commercial distribution and biodistribution may not be sufficient. $^{18}$F ($\beta^+$635 keV 97%, $t_{1/2}$ 110 min) is one of the most widely used PET emitting isotopes because of its low positron emission energy, lack of side emissions and suitable half-life.

$^{18}$F is produced with a high specific activity. When an isotope is attached to a molecule for targeting it is usually accompanied by some unreacted targeting agent, which is often present in a large molar excess compared to the radiolabeled product. Usually, the labeled product and the unlabeled product can compete for the same target in vivo so the presence of the cold targeting agent lowers the effective specific activity of the targeting agent. If the $^{18}$F is attached to a molecule which has a very high uptake such as 2-fluoro-2-deoxy glucose (FDG) then effective specific activity is not as important. However, if one is targeting a receptor with a labeled peptide or performing an immunoPET pretargeting study with a limited number of binding sites available, the cold targeting agent could potentially block the uptake of the radiolabeled targeting agent if the cold targeting agent is present in excess.

Conventionally, $^{18}$F is attached to compounds by binding it to a carbon atom (Miller et al., 2008, Angew Chem Int Ed 47:8998-9033), but attachments to silicon (Shirrmacher et al., 2007, Bioconj Chem 18:2085-89; Hohne et al., 2008, Bioconj Chem 19:1871-79) and boron (Ting et al., 2008, Fluorine Chem 129:349-58) have also been reported. Binding to carbon usually involves multistep syntheses, including multiple purification steps, which is problematic for an isotope with a 110-min half-life. Current methods for $^{18}$F labeling of peptides typically involve the labeling of a reagent at low specific activity, HPLC purification of the reagent and then conjugation to the peptide of interest. The conjugate is often repurified after conjugation to obtain the desired specific activity of labeled peptide.

An example is the labeling method of Poethko et al. (J. Nucl. Med. 2004; 45: 892-902) in which 4-[$^{18}$F]fluorobenzaldehyde is first synthesized and purified (Wilson et al, J Labeled Compounds and Radiopharm. 1990; XXVIII: 1189-1199) and then conjugated to the peptide. The peptide conjugate is then purified by HPLC to remove excess peptide that was used to drive the conjugation to completion. Other examples include labeling with succinyl [$^{18}$F]fluorobenzoate (SFB) (e.g., Vaidyanathan et al., 1992, Int. J. Rad. Appl. Instrum. B 19:275), other acyl compounds (Tada et al., 1989, Labeled Compd. Radiopharm. XXVII:1317; Wester et al., 1996, Nucl. Med. Biol. 23:365; Guhlke et al., 1994, Nucl. MEd. Biol 21:819), or click chemistry adducts (Li et al., 2007, Bioconjugate Chem. 18:1987). The total synthesis and formulation time for these methods ranges between 1-3 hours, with most of the time dedicated to the HPLC purification of the labeled peptides to obtain the specific activity required for in vivo targeting. The multiple reactions and purifications would not be a problem if $^{18}$F had a long half-life. However, with a 2 hr half-life, all of the manipulations that are needed to attach the $^{18}$F to the peptide are a significant burden. These methods are also tedious to perform and require the use of equipment designed specifically to produce the labeled product and/or the efforts of specialized professional chemists. They are also not conducive to kit formulations that could routinely be used in a clinical setting.

One alternative method for delivery of labeled adducts to tumors or other target tissues has involved a pretargeting approach (e.g., U.S. Pat. Nos. 7,052,872; 7,074,405; 7,138,103, each incorporated herein by reference). Prior studies using the bispecific antibody (bsMAb) pretargeting procedure (e.g., McBride et al., 2006, J. Nucl. Med. 10:1678-88) have focused on the use of $^{124}$I, achieving better targeting of colon cancer xenografts in animal models than directly radiolabeled fragments or $^{18}$F-FDG. While the technique has had impressive results, $^{124}$I is not a viable candidate for this imaging procedure, primarily because of its high cost (more than $2000 per dose) and relatively poor imaging properties compared to other alternatives. Other antibody-based targeting methods have had to rely on radioiodinated products for a variety of reasons, mostly because tumor/background ratios require >6 h before achieving acceptable levels. However, the pretargeting method can achieve acceptable imaging conditions within 1 h (Hamacher et al., 1986, J. Nucl. Med. 27:235; Iwata et al., 2000, Appl. Radiat. Isot. 52:87).

A need exists for a rapid, simple method of $^{18}$F labeling of targeting moieties, such as proteins or peptides, that results in targeting constructs of suitable specific activity and in vivo stability for detection and/or imaging, while minimizing the requirements for specialized equipment or highly trained personnel and reducing operator exposure to high levels of radiation. More preferably a need exists for methods of preparing $^{18}$F-labeled targeting peptides of use in pretargeting technologies. A further need exists for prepackaged kits that could provide compositions required for performing such novel methods.

SUMMARY

Fluoride binds to practically all other elements and some of those bonds are relatively stable. Peptides bearing metal binding ligands are known to bind radiometals stably and at very high specific activity. The approach utilized in the present invention was to first bind the $^{18}$F to a metal and then chelate the $^{18}$F metal complex with a ligand on the peptide. An initial question was which metal to choose. The metals of group III A (aluminum, gallium, indium, and thallium) were the first choice. Lutetium may also be of use. The metal binding ligand of use to attach an $^{18}$F-metal complex to a protein, peptide or other molecule is also important, as different metals bind with different affinities to various chelating agents, such as NOTA, NETA, DOTA, DTPA and other chelating groups discussed in more detail below. Alternatively, one might attach the metal or other atom to the peptide first and then add the $^{18}$F.

Aluminum fluoride complexes are reported to be stable in-vitro (Martinez et al, Inorg Chem. 1999; 38: 4765-4660; Antonny et al. J. Biol. Chem. 1992; 267: 6710-6718). Aluminum fluoride becomes incorporated into bone and into the enamel of teeth so the complexes can also be stable in-vivo (Li, Crit. Rev. Oral Biol. Med. 2003; 14: 100-114).

The skilled artisan will realize that virtually any delivery molecule can be used to attach the $^{18}$F for imaging purposes, so long as it contains derivatizable groups that may be modified without affecting the ligand-receptor binding interaction between the delivery molecule and the cellular or tissue target receptor. Although the Examples below concern $^{18}$F-labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, lipids, etc. may be $^{18}$F-labeled and utilized for imaging purposes.

Similarly, the type of diseases or conditions that may be imaged is limited only by the availability of a suitable delivery molecule for targeting a cell or tissue associated with the disease or condition. Many such delivery molecules are known, as exemplified in the Examples below. For example, any protein or peptide that binds to a diseased tissue or target, such as cancer, may be labeled with $^{18}$F by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with $^{18}$F by the described methods and used for imaging and/or detection of tumors, for example by PET scanning or other known techniques.

In certain Examples below, the exemplary $^{18}$F-labeled peptides may be of use for imaging purposes as targetable constructs in a pre-targeting method, utilizing bispecific or multispecific antibodies or antibody fragments. In this case, the antibody or fragment will comprise one or more binding sites for a target associated with a disease or condition, such as a tumor-associated or autoimmune disease-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the Examples section of which is incorporated herein by reference.) Similarly, antibodies or fragments thereof that bind to targetable constructs are also well known in the art (Id.), such as the 679 monoclonal antibody that binds to HSG (histamine succinyl glycine). Generally, in pretargeting methods the bispecific or multispecific antibody is administered first and allowed to bind to cell or tissue target antigens. After an appropriate amount of time for unbound antibody to clear from circulation, the e.g. $^{18}$F-labeled targetable construct is administered to the patient and binds to the antibody localized to target cells or tissues, then an image is taken for example by PET scanning.

In an alternative exemplary embodiment, a non-peptide receptor targeting agent such as folic acid may be conjugated to NOTA or another chelating moiety and then labeled with, for example, an $^{18}$F-metal complex that binds to NOTA. Such non-peptide receptor targeting agents may include, for example, TA138, a non-peptide antagonist for the integrin $\alpha_v\beta_3$ receptor (Liu et al., 2003, Bioconj. Chem. 14:1052-56). Similar non-peptide targeting agents known in the art that can be conjugated to DOTA, NOTA or another chelating agent for $^{18}$F-metal complexes may be utilized in the claimed methods. Other receptor targeting agents are known in the art, such as the somatostatin receptor targeting agent In-DTPA octreotide (TYCO®). As discussed below, an $^{18}$F-metal complex could potentially be chelated using DTPA and used for imaging purposes. The NODAGATOC peptide could be labeled with $Al^{18}F$ for somatostatin receptor targeting (Eisenwiener et. al. Bioconj. Chem. 2002, 13(3):530-41). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

Imaging techniques and apparatus for $^{18}$F imaging by PET scanning are also well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

Although the Examples below demonstrate the use of $^{18}$F-metal complexes for PET imaging, the skilled artisan will realize that stable metal-fluoride complexes, such as the non-radioactive $^{27}$Al and $^{19}$F complex, could also be bound to NOTA or other chelators and attached to peptides or other targeting agents for use as an MRI contrast agent. The [AlF]-chelator complexes could also be attached to polymers for MRI imaging. The AlF-chelator derivatives could be used as PARACEST MRI imaging agents (Woessner et. al. Magn. Reson. Med. 2005, 53: 790-99).

BRIEF DESCRIPTION OF THE DRAWINGS

The following Figures are included to illustrate particular embodiments of the invention and are not meant to be limiting as to the scope of the claimed subject matter.

DETAILED DESCRIPTION

Figure 1:
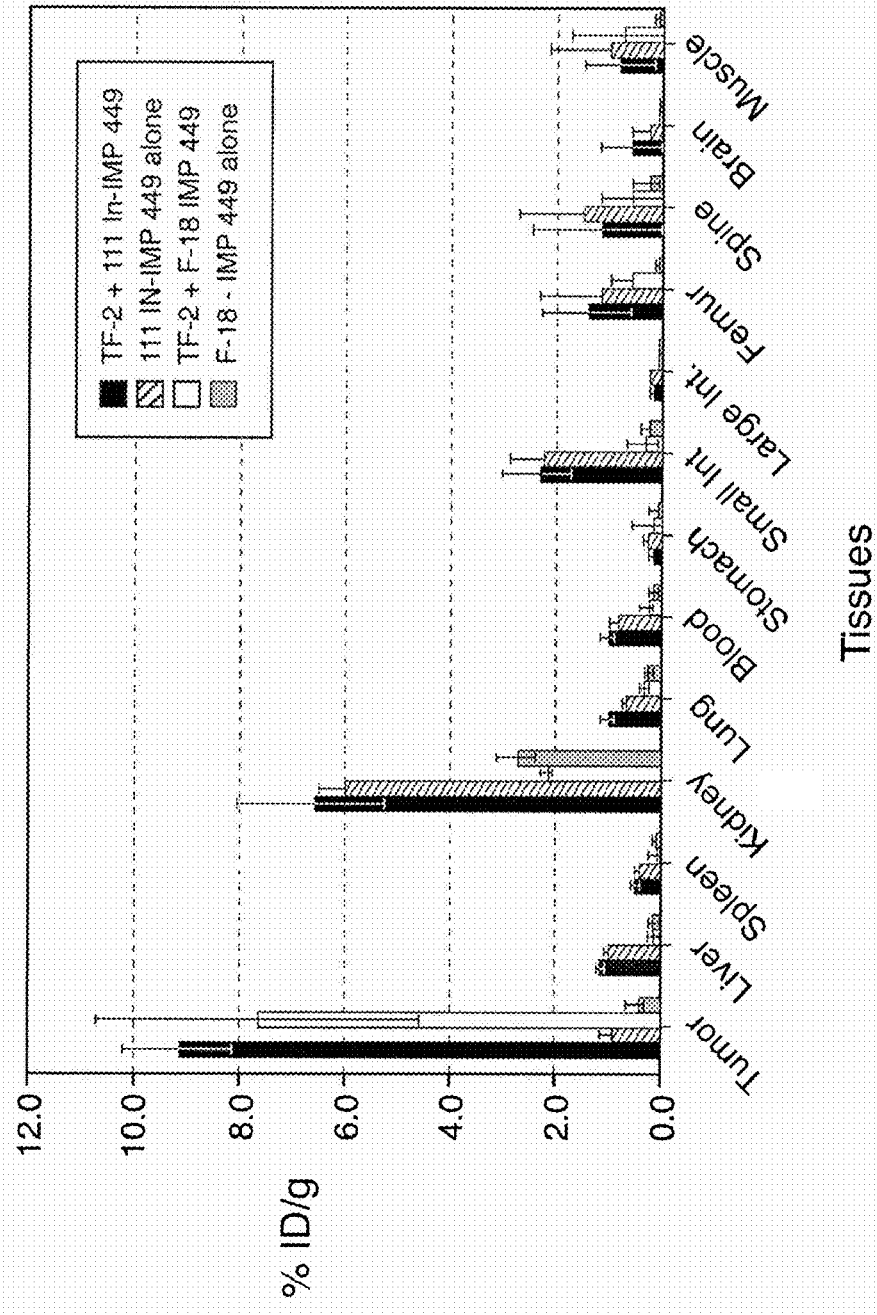
FIG. 1. Comparative biodistribution of $^{111}$In and $^{18}$F labeled IMP 449 in mice with or without TF2 bispecific antibody.

The following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae*, *Legionella pneumophilia*, *Streptococcus pyogenes*, *Escherichia coli*, *Neisseria gonorrhoeae*, *Neisseria meningitidis*, Pneumococcus, *Hemophilis influenzae B*, *Treponema pallidum*, Lyme disease spirochetes, *Pseudomonas aeruginosa*, *Mycobacterium leprae*, *Brucella abortus*, *Mycobacterium tuberculosis* and *Chlostridium tetani*.

As used herein, a "radiolysis protection agent" refers to any molecule, compound or composition that may be added to an $^{18}$F-labeled complex or molecule to decrease the rate of breakdown of the $^{18}$F-labeled complex or molecule by radiolysis. Any known radiolysis protection agent, including but not limited to ascorbic acid, may be used.

Comparison of $^{18}$F Labeling Techniques

A variety of techniques for labeling molecules with $^{18}$F are known. Table 1 lists the properties of several of the more commonly reported fluorination procedures. Peptide labeling through carbon often involves $^{18}$F-binding to a prosthetic group through nucleophilic substitution, usually in 2- or 3-steps where the prosthetic group is labeled and purified, attached to the compound, and then purified again. This general method has been used to attach prosthetic groups through amide bonds, aldehydes, and "click chemistry" (Marik et al., 2006, Bioconjug Chem 17:1017-21; Poethko et al., 2004, J Nucl Med 45:892-902; Li et al., 2007, Bioconjug Chem 18:989-93). The most common amide bond-forming reagent has been N-succinimidyl 4-$^{18}$F-fluorobenzoate ($^{18}$F-SFB), but a number of other groups have been tested (Marik et al., 2006). In some cases, such as when $^{18}$F-labeled active ester amide-forming groups are used, it may be necessary to protect certain groups on a peptide during the coupling reaction, after which they are cleaved. The synthesis of this $^{18}$F-SFB reagent and subsequent conjugation to the peptide requires many synthetic steps and takes about 2-3 h.

A simpler, more efficient $^{18}$F-peptide labeling method was developed by Poethko et al. (2004), where a 4-$^{18}$F-fluorobenzaldehyde reagent was conjugated to a peptide through an oxime linkage in about 75-90 min, including the dry-down step. The newer "click chemistry" method attaches $^{18}$F-labeled molecules onto peptides with an acetylene or azide in the presence of a copper catalyst (Li et al, 2007; Glaser and Arstad, 2007, Bioconjug Chem 18:989-93). The reaction between the azide and acetylene groups forms a triazole connection, which is quite stable and forms very efficiently on peptides without the need for protecting groups. Click chemistry produces the $^{18}$F-labeled peptides in good yield (~50%) in about 75-90 min with the dry-down step.

TABLE 1

Summary of selected $^{18}$F-peptide labeling methods.

| Author/Ref. | Schirrmacer et al. (2007) | Höhne et al. (2008) | Li et al. (2007) | Glaser & Arstad (2007) | Poethko et al. (2004) | Marik et al (2006) |
|---|---|---|---|---|---|---|
| Attachment | Silicon | Silicon | Click | Click | Aldehyde/oxime | Amide |
| Rx steps | 2 | 1 | 2 | 2 | 2 | many |
| Rx time (min)[a] | 40 | 115-155 | 110 | 65-80 (estimated) | 75-90 min (estimated) | 110+ |
| Yield[b] | 55% | 13% | 54% | 50% | 40% | 10% |
| HPLC-purification steps | 1 | 1 | 2 | 1 + distillation | 1 | 2 |
| Specific Activity (GBq/μmol) | 225-680 | 62 | high | high | high | high |

[a]Including dry-down time
[b]Decay corrected

A more recent method of binding $^{18}$F to silicon uses isotopic exchange to displace $^{19}$F with $^{18}$F (Shirrmacher et al., 2007). Performed at room temperature in 10 min, this reaction produces the $^{18}$F-prosthetic aldehyde group with high specific activity (225-680 GBq/μmol; 6,100-18,400

Ci/mmol). The $^{18}$F-labeled aldehyde is subsequently conjugated to a peptide and purified by HPLC, and the purified labeled peptide is obtained within 40 min (including drydown) with 55% yield. This was modified subsequently to a single-step process by incorporating the silicon into the peptide before the labeling reaction (Hohne et al, 2008). However, biodistribution studies in mice with an $^{18}$F-silicon-bombesin derivative showed bone uptake increasing over time (1.35±0.47% injected dose (ID)/g at 0.5 h vs. 5.14±2.71% ID/g at 4.0 h), suggesting a release of $^{18}$F from the peptide, since unbound $^{18}$F is known to localize in bone (Hohne et al., 2008). HPLC analysis of urine showed a substantial amount of $^{18}$F activity in the void volume, which presumably is due to $^{18}$F$^-$ fluoride anion released from the peptide. It would therefore appear that the $^{18}$F-silicon labeled molecule was not stable in serum. Substantial hepatobiliary excretion was also reported, attributed to the lipophilic nature of the $^{18}$F-silicon-binding substrate, and requiring future derivatives to be more hydrophilic. Methods of attaching $^{18}$F to boron also have been explored; however, the current process produces conjugates with low specific activity (Ting et al., 2008).

Antibodies and peptides are coupled routinely with radiometals, typically in 15 min and in quantitative yields (Meares et al., 1984, Acc Chem Res 17:202-209; Scheinberg et al., 1982, Science 215:1511-13). For PET imaging, $^{64}$Cu and, more recently, $^{68}$Ga have been bound to peptides via a chelate, and have shown reasonably good PET-imaging properties (Heppler et al., 2000, Current Med Chem 7:971-94). Since fluoride binds to most metals, we sought to determine if an $^{18}$F-metal complex could be bound to a chelator on a targeting molecule (Tewson, 1989, Nucl Med. Biol. 16:533-51; Martin, 1996, Coordination Chem Rev 141:23-32). We have focused on the binding of an Al$^{18}$F complex, since aluminum-fluoride can be relatively in vivo (Li, 2003, Crit. Rev Oral Biol Med 14:100-114; Antonny et al., 1992, J Biol Chem 267:6710-18). We have reported initial studies that showed the feasibility of this approach to prepare an $^{18}$F-labeled peptide for in vivo targeting of cancer with a bispecific antibody (bsMAb) pre-targeting system, a highly sensitive and specific technique for localizing cancer, in some cases better than $^{18}$F-FDG (fluorodeoxyglucose) (McBride et al., 2008, J Nucl Med (suppl) 49:97 P; Wagner, 2008, J Nucl Med 49:23 N-24N; Karacay et al., 2000, Bioconj Chem 11:842-54; Sharkey et al., 2008, Cancer Res 68; 5282-90; Gold Et al., 2008, Cancer Res 68:4819-26; Sharkey et al., 2005, Nature Med 11:1250-55; Sharkey et al., 2005, Clin Cancer Res 11:7109s-7121s; McBride et al., 2006, J Nucl Med 47:1678-88; Sharkey et al., 2008, Radiology 246:497-508). These studies revealed that an Al$^{18}$F complex could bind stably to a 1,4,7-triazacyclononane-1,4,7-triacetic acid (NOTA), but the yields were low.

In the Examples below, new labeling conditions and several new NOTA derivatives were examined that enhanced yields from about 10% to about 80%, providing a feasible method for $^{18}$F labeling of peptides and other molecules of use for PET imaging.

Targetable Construct Peptides

In certain embodiments, the $^{18}$F-labeled moiety may comprise a peptide or other targetable construct. $^{18}$F-labeled peptides (or proteins) may be selected to bind directly to a targeted cell, tissue, pathogenic organism or other target for imaging and/or detection. In other embodiments, $^{18}$F-labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as an $^{18}$F-labeled peptide, may be administered to the subject and allowed to bind to the bispecific antibody and localize at the diseased cell or tissue, after which the distribution of the $^{18}$F-labeled targetable construct may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. More usually, the targetable construct peptide will have four or more residues, such as the peptide DOTA-Phe-Lys(HSG)-Tyr-Lys(HSG)-NH$_2$ (SEQ ID NO: 1). wherein DOTA is 1,4,7,10-tetraazacyclododecane1,4,7,10-tetraacetic acid and HSG is the histamine succinyl glycyl group. Alternatively, the DOTA may be replaced by a NOTA (1,4,7-triaza-cyclononane-1,4,7-triacetic acid), TETA (p-bromoacetamido-benzyl-tetraethylaminetetraacetic acid), NETA ([2-(4,7-bis-carboxymethyl[1,4,7]triazacyclononan-1-yl-ethyl]-2-carbonylmethyl-amino]acetic acid) or other known chelating moiety.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

The haptens of the immunogen comprise a recognition moiety, for example, a chemical hapten. Using a chemical hapten, preferably the HSG hapten, high specificity of the linker for the antibody is exhibited. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). Thus, binding of the linker with the attached hapten would be highly specific for the antibody or antibody fragment. However, other haptens and antibodies that bind to them are known in the art and may be used, such as In-DTPA and the 734 antibody (e.g., U.S. Patent Application Publication No. 20050002945).

Chelate Moieties

In some embodiments, an $^{18}$F-labeled molecule may comprise one or more hydrophilic chelate moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triaza-cyclononane-1,4,7-triacetic acid), DOTA, TETA (p-bromoacetamido-benzyl-tetraethylaminetetraacetic acid) and NETA are also of use with a variety of metals, that may potentially be used as ligands for $^{18}$F conjugation.

DTPA and DOTA-type chelators, where the ligand includes hard base chelating functions such as carboxylate or amine groups, are most effective for chelating hard acid cations, especially Group Ia and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. No. 5,256,395) and are readily coupled to a targeting antibody to form a bispecific antibody, it is possible to use a peptide hapten with cold diDTPA chelator and another chelator for binding an $^{18}$F complex, in a pretargeting protocol. One example of such a peptide is Ac-Lys(DTPA)-Tyr-Lys (DTPA)-Lys(Tscg-Cys)-NH$_2$ (SEQ ID NO:2). Other hard acid chelators such as DOTA, TETA and the like can be substituted for the DTPA and/or Tscg-Cys groups, and MAbs specific to them can be produced using analogous techniques to those used to generate the anti-di-DTPA MAb.

Another useful chelator may comprise a NOTA-type moiety, for example as disclosed in Chong et al. (*J. Med. Chem.*, 2008, 51:118-25, incorporated herein by reference). Chong et al. disclose the production and use of a bifunctional C-NETA ligand, based upon the NOTA structure, that when complexed with $^{177}$Lu or $^{205/206}$Bi showed stability in serum for up to 14 days. The chelators are not limiting and these and other examples of chelators that are known in the art and/or described in the following Examples may be used in the practice of the invention.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to $^{18}$F, to be incorporated into a targetable construct for eventual capture by a pretargeted bispecific antibody.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference in its Examples section).

The administration of a bispecific antibody (bsAb) and an $^{18}$F-labeled targetable construct may be conducted by administering the bsAb antibody at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr (alternatively 48-96 hours) before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the $^{18}$F-labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

Alternatively, a technique known as "dock-and-lock" (DNL), described in more detail below, has been demonstrated for the simple and reproducible construction of a variety of multivalent complexes, including complexes comprising two or more different antibodies or antibody fragments. (See, e.g., U.S. patent application Ser. Nos. 11/389,358, filed Mar. 24, 2006; 11/391,584, filed Mar. 28, 2006; 11/478,021, filed Jun. 29, 2006; 11/633,729, filed Dec. 5, 2006; and 11/925,408, filed Oct. 26, 2007, the Examples section of each of which is incorporated herein by reference.) Such constructs are also of use for the practice of the claimed methods and compositions described herein.

A clearing agent may be used which is given between doses of the bispecific antibody (bsAb) and the targetable construct. A clearing agent of novel mechanistic action may be used, namely a glycosylated anti-idiotypic Fab' fragment targeted against the disease targeting arm(s) of the bsAb. In one example, anti-CEA (MN-14 Ab) x anti-peptide bsAb is given and allowed to accrete in disease targets to its maximum extent. To clear residual bsAb from circulation, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the $^{18}$F-labeled targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety. However, alternative methods and compositions for clearing agents are known and any such known clearing agents may be used.

Formulation and Administration

The $^{18}$F-labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the $^{18}$F-labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection. Injection may be intravenous, intraarterial, intralymphatic, intrathecal, or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising $^{18}$F-labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, for imaging purposes it is desirable to provide the recipient with a dosage of bispecific antibody that is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject for imaging purposes are 1 to 200 mg, more preferably 1 to 70 mg, most preferably 1 to 20 mg, although higher or lower doses may be used.

In general, the dosage of $^{18}$F label to administer will vary depending upon such factors as the patient's age, weight, height, sex, general medical condition and previous medical history. Preferably, a saturating dose of the $^{18}$F-labeled molecules is administered to a patient. For administration of $^{18}$F-labeled molecules, the dosage may be measured by millicuries. A typical range for $^{18}$F imaging studies would be five to 10 mCi.

Administration of Peptides

Various embodiments of the claimed methods and/or compositions may concern one or more $^{18}$F-labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, $^{18}$F-labeled peptides are administered in a pretargeting protocol, the peptides would preferably be administered i.v. Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. 1, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based $^{18}$F-labeled molecules suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, the Examples section of which is incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

Methods for Raising Antibodies

Abs to peptide backbones may be generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the targetable construct, e.g., In(III)-DTPA chelates. Monoclonal mouse antibodies to an In(III)-di-DTPA are known (Barbet '395 supra).

Targeting antibodies of use, for example as components of bispecific antibodies, may be specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Recent reports on tumor associated antigens (TAAs) include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). Further it is known that TACI and B cell maturation antigen (BCMA) are bound by the tumor necrosis factor homolog—a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Exemplary target antigens of use for imaging various diseases or conditions, such as a malignant disease, a cardiovascular disease, an infectious disease, an inflammatory disease, an autoimmune disease, or a neurological disease may include carbonic anhydrase IX, CCCL19, CCCL21, CSAp, CDT, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product.

Where imaging or detection involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, P1GF, ED-B fibronectin, an oncogene, an oncogene product, CD66a-d, necrosis antigens, IL-2, T101, TAG, IL-6, MIF, TRAIL-R1 (DR4) and TRAIL-R2 (DR5).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., Proc. Nat'l Acad. Sci. USA 86: 3833 (1989), incorporated herein by reference. Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is incorporated herein by reference.

Alternatively, fully human antibodies can be obtained from transgenic non-human animals. See, e.g., Mendez et al., Nature Genetics, 15: 146-156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment may be derived from human antibody fragments isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994), which are incorporated herein by reference. Many of the difficulties associated with generating monoclonal antibodies by B-cell immortalization can be overcome by engineering and expressing antibody fragments in E. coli, using phage display.

A similar strategy can be employed to obtain high-affinity scFv. See, e.g., Vaughn et al., Nat. Biotechnol., 14: 309-314 (1996). An scFv library with a large repertoire can be constructed by isolating V-genes from non-immunized human donors using PCR primers corresponding to all known $V_H$, $V_{kappa}$ and $V_{80}$ gene families. Following amplification, the $V_{kappa}$ and $V_{lambda}$ pools are combined to form one pool. These fragments are ligated into a phagemid vector. The scFv linker, $(Gly_4, Ser)_3$ (SEQ ID NO: 21), is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (NUNC®; MAX-ISORP®). Similar results can be achieved by constructing a combinatorial immunoglobulin library from lymphocytes or spleen cells of immunized rabbits and by expressing the scFv constructs in P. pastoris. See, e.g., Ridder et al., Biotechnology, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181-188 (1998); Osbourn et al., Immunotechnology, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRIN- CIPLES AND APPLICATIONS, Birch et al., (eds.), pages 137-185 (Wiley-Liss, Inc. 1995).

A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain attached to human constant region sequences.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bispecific antibodies include engineered recombinant Abs which have additional cysteine residues so that they crosslink more strongly than the more common immunoglobulin isotypes. See, e.g., FitzGerald et al., Protein Eng. 10:1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021-7025, 1995.

Preferred bispecific antibodies are those which incorporate the Fv of MAb Mu-9 and the Fv of MAb 679 or the Fv of MAb MN-14 and the Fv of MAb 679, and their human, chimerized or humanized counterparts. The MN-14, as well as its chimerized and humanized counterparts, are disclosed in U.S. Pat. No. 5,874,540. Also preferred are bispecific antibodies which incorporate one or more of the CDRs of Mu-9 or 679. The antibody can also be a fusion protein or a bispecific antibody that incorporates a Class III anti-CEA antibody and the Fv of 679. Class III antibodies, including Class III anti-CEA are discussed in detail in U.S. Pat. No. 4,818,709.

The skilled artisan will realize that bispecific antibodies may incorporate any antibody or fragment known in the art that has binding specificity for a target antigen that is known to be associated with a disease state or condition. Such known antibodies include, but are not limited to, hR1 (anti-IGF-1R, U.S. Provisional Patent Application Ser. No. 61/145,896, filed Jan. 20, 2009) hPAM4 (anti-MUC1, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. patent application Ser. No. 11/368,296), hMN-14 (anti-CEA, U.S. Pat. No. 6,676,924), hMN-15 (anti-CEA, U.S. patent application Ser. No. 10/672,278), hRS7 (anti-EGP-1, U.S. Pat. No. 7,238,785) and hMN-3 (anti-CEA, U.S. patent application Ser. No. 10/672,278) the Examples section of each cited patent or application incorporated herein by reference. The second MAb may also be selected from any anti-hapten antibody known in the art, including but not limited to h679 (U.S. Pat. No. 7,429,381) and 734 (U.S. patent application Ser. No. 10/776,470), the Examples section of each of which is incorporated herein by reference.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; and U.S. Patent Application Publ. No. 20040185053; 20040202666; 20050271671; 20060193865; 20060210475; 20070087001; each incorporated herein by reference.) Such known antibodies are of use for detection and/or imaging of a variety of disease states or conditions (e.g., hMN-14 or TF2 bsMAb (CEA-expressing carcinomas), hA20 bsMab (TF-4-lymphoma), hPAM4 (TF-10 pancreas cancers), RS7 bsMAb (lung, breast, ovarian, prostatic cancers), hMN-15 or hMN3 bsMAb (inflammation), human gp120 and/or gp41 bsMAbs (HIV), anti-platelet bsMab and anti-thrombin bsMAb (clot imaging), anti-myosin bsMAb (cardiac necrosis)).

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393;

6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agens Chemother. 2006; 50(5):1773-9, all incorporated herein by reference.

In certain embodiments, the bsAb F-18 labeled targetable constructs may be used in intraoperative, intravascular, and/or endoscopic tumor and lesion detection, biopsy and therapy as described in U.S. Pat. No. 6,096,289.

General Techniques for Antibody Cloning and Construction

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (Proc. Natl. Acad. Sci., USA, 86: 3833 (1989)). Based on the V gene sequences, a humanized MAb can then be designed and constructed as described by Leung et al. (Mol. Immunol., 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al., 1989) or the extended primer set described by Leung et al. (BioTechniques, 15: 286 (1993)). The $V_H$ sequences can be amplified using the primer pair VH1BACK/VH1FOR (Orlandi et al, 1989) or the primers annealing to the constant region of murine IgG described by Leung et al. (Hybridoma, 13:469 (1994)).

PCR reaction mixtures containing 10 µl of the first strand cDNA product, 10 µl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified V κ and $V_H$ fragments can be purified on 2% agarose (BioRad, Richmond, Calif.). The humanized V genes can be constructed by a combination of long oligonucleotide template syntheses and PCR amplification as described by Leung et al. (Mol. Immunol., 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (Proc. Natl. Acad. Sci., USA, 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human MAb by, for example, an ELISA assay. Alternatively, the Vκ and $V_H$ expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gillies et al. (J. Immunol. Methods 125:191 (1989) and also shown in Losman et al., Cancer, 80:2660 (1997)). Another vector that is useful is the GS vector, as described in Barnes et al., Cytotechnology 32:109-123 (2000). Other appropriate mammalian expression systems are described in Werner et al., Arzneim.-Forsch./Drug Res. 48(II), Nr. 8, 870-880 (1998).

Co-transfection and assay for antibody secreting clones by ELISA, can be carried out as follows. About 10 µg of VKpKh (light chain expression vector) and 20 µg of VHpG1g (heavy chain expression vector) can be used for the transfection of $5×10^6$ SP2/0 myeloma cells by electroporation (BioRad, Richmond, Calif.) according to Co et al., J. Immunol., 148: 1149 (1992). Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2µ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.).

The antibody concentration is determined by ELISA and its concentration adjusted to about 1 mg/ml using PBS. Sodium azide, 0.01% (w/v), is conveniently added to the sample as preservative.

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. patent application Ser. Nos. 11/187,863; 11/253,666; 11/487,215 and 11/877,728; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression may be utilized, such as Sp2/0, an Sp2/0 derivative, NSO, YB2/0, CHO, HEK 293, COS-1, COS-7, HepG2, BHK21, P3X3Ag8.653 or BSC-1

Bispecific and Multispecific Antibodies

Bispecific antibodies can be prepared by techniques known in the art, for example, an anti-CEA tumor Ab and an anti-peptide Ab are both separately digested with pepsin to their respective F(ab')$_2$ fragments. The anti-CEA-Ab-F(ab')$_2$ is reduced with cysteine to generate Fab' monomeric units which are further reacted with the cross-linker bis(maleimido) hexane to produce Fab'-maleimide moieties. The anti-peptide Ab-F(ab')$_2$ is reduced with cysteine and the purified, recovered anti-peptide Fab'-SH is reacted with the anti-CEA-Fab'-maleimide to generate the Fab'×Fab' bi-specific Ab. Alternatively, the anti-peptide Fab'-SH fragment may be coupled with the anti-CEA F(ab')$_2$ to generate a F(ab')$_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. Bispecific or multispecific antibodies may incorporate any known antibody of therapeutic use, as discussed above in the preceding section.

Numerous methods to produce bispecific or multispecific antibodies are known, as disclosed, for example, in U.S. Patent Application Publication No. 20050002945, filed Feb. 11, 2004, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL), discussed in more detail below, has been utilized to produce combinations of virtually any desired antibodies, antibody fragments and other effector molecules (see, e.g., U.S. Patent Application Publ. Nos. 20060228357; 20060228300; 20070086942; 20070140966 and 20070264265, the Examples section of each incorporated herein by reference). The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, pro-apoptotic agents, or a combination thereof. Any of the techniques known in the art for making bispecific or multispecific antibodies may be utilized in the practice of the presently claimed methods.

Dock-and-Lock (DNL)

In preferred embodiments, bispecific or multispecific antibodies or other constructs may be produced using the dock-and-lock technology (see, e.g., U.S. patent application Ser. Nos. 11/389,358; 11/391,584; 11/478,021; 11/633,729 and 11/925,408, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RII: are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. patent application Ser. Nos. 11/389,358; 11/391,584; 11/478,021; 11/633,729 and 11/925,408, the Examples section of each of which is incorporated herein by reference.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361,026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472,511; U.S. Ser. No. 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. No. 09/823,746; U.S. Ser. No. 09/337,756; U.S. Provisional Application No. 60/342,103; and U.S. Pat. No. 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Amino Acid Substitutions

In certain embodiments, the disclosed methods and compositions may involve production and use of proteins or peptides with one or more substituted amino acid residues. For example, the DDD and/or AD sequences used to make DNL constructs may be further optimized, for example to increase the DDD-AD binding affinity. Potential sequence variations in DDD or AD sequences are discussed in the Examples below.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gin, asn, lys; Asn (N) his, asp, lys, arg, gln; Asp (D) asn, glu; Cys (C) ala, ser; Gln (O) glu, asn; Glu (E) gin, asp; Gly (G) ala; His (H) asn, gin, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Imaging Using Labeled Molecules

Methods of imaging using labeled molecules are well known in the art, and any such known methods may be used with the $^{18}$F-labeled molecules disclosed herein. See, e.g., U.S. Pat. Nos. 6,241,964; 6,358,489; 6,953,567 and published U.S. Patent Application Publ. Nos. 20050003403; 20040018557; 20060140936, the Examples section of each incorporated herein by reference. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

In certain embodiments, $^{18}$F-labeled molecules may be of use in imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001. Such imaging can be conducted by direct $^{18}$F labeling of the appropriate targeting molecules, or by a pretargeted imaging method, as described in Goldenberg et al. (2007, Update Cancer Ther. 2:19-31); Sharkey et al. (2008, Radiology 246: 497-507); Goldenberg et al. (2008, J. Nucl. Med. 49:158-63); Sharkey et al. (2007, Clin. Cancer Res. 13:5777s-5585s); McBride et al. (2006, J. Nucl. Med. 47:1678-88); Goldenberg et al. (2006, J. Clin. Oncol. 24:823-85), see also U.S. Patent Publication Nos. 20050002945, 20040018557, 20030148409 and 20050014207, each incorporated herein by reference.

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}F$, $^{68}Ga$, $^{64}Cu$, and $^{124}I$. Such radionuclides may be imaged by well-known PET scanning techniques.

In preferred embodiments, the $^{18}F$-labeled peptides, proteins and/or antibodies are of use for imaging of cancer. Examples of cancers include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or diagnose malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

The exemplary conditions listed above that may be detected, diagnosed and/or imaged are not limiting. The skilled artisan will be aware that antibodies, antibody fragments or targeting peptides are known for a wide variety of conditions, such as autoimmune disease, cardiovascular disease, neurodegenerative disease, metabolic disease, cancer, infectious disease and hyperproliferative disease. Any such condition for which an $^{18}$F-labeled molecule, such as a protein or peptide, may be prepared and utilized by the methods described herein, may be imaged, diagnosed and/or detected as described herein.

Kits

Various embodiments may concern kits containing components suitable for detecting, diagnosing and/or imaging diseased tissue in a patient by $^{18}$F PET imaging. Exemplary kits may contain an antibody, fragment or fusion protein, such as a bispecific antibody of use in pretargeting methods as described herein. Other components may include a targetable construct for use with such bispecific antibodies. Preferably, the targetable construct is pre-conjugated to a chelating group that may be used to attach an Al$^{18}$F complex or a complex of $^{18}$F with a different metal. However, in alternative embodiments it is contemplated that a chelator may be included separately, to attach to an Al$^{18}$F complex before conjugation of the Al$^{18}$F-chelating moiety to a targetable construct or other targeting peptide, protein or other molecule. Although certain preferred embodiments described in the Examples below utilize bispecific antibodies and $^{18}$F-labeled targetable constructs in a pretargeting method, the skilled artisan will realize that in other embodiments, the $^{18}$F labeling methods disclosed and claimed herein may be utilized with non-antibody targeting proteins, peptides or other molecules.

The kit may contain additional reagents and other components of use to attach freshly prepared Al$^{18}$F or $^{18}$F-metal to a targetable construct or other targeting molecule and/or, optionally to partially or fully purify an $^{18}$F-labeled targeting molecule from unlabeled targeting molecules, unincorporated $^{18}$F and other components of the mixture. However, the skilled artisan will realize that in certain preferred embodiments, the efficiency of incorporation and labeling and the specific radioactivity of the labeled construct are sufficiently high that an unpurified $^{18}$F-labeled targeting molecule, prepared as described herein, may be utilized for PET imaging. In most preferred embodiments, the kit may contain all components needed to prepare and use an $^{18}$F-labeled protein, peptide or other molecule for PET imaging, other than freshly prepared $^{18}$F which may be obtained from commercial sources.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and

EXAMPLES

Example 1

$^{18}$F Labeling of Peptide IMP 272

The first peptide that was prepared and $^{18}$F-labeled was IMP 272:

DTPA-Gln-Ala-Lys(HSG)-D-Tyr-Lys(HSG)-NH$_2$   MH$^+$ 1512

Acetate buffer solution—Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28×10$^{-7}$ mol IMP 272 was dissolved in 364 μL of the 0.1 M pH 4 acetate buffer solution to obtain a 2 mM stock solution of the peptide.

F-18 Labeling of IMP 272—A 3 μL aliquot of the aluminum stock solution was placed in a REACTI-VIAL™ and mixed with 50 μL $^{18}$F (as received) and 3 μL of the IMP 272 solution. The solution was heated in a heating block at 110° C. for 15 min and analyzed by reverse phase HPLC. The HPLC trace (not shown) showed 93% free $^{18}$F and 7% bound to the peptide. An additional 10 μL of the IMP 272 solution was added to the reaction and it was heated again and analyzed by reverse phase HPLC (not shown). The HPLC trace showed 8% $^{18}$F at the void volume and 92% of the activity attached to the peptide. The remainder of the peptide solution was incubated at room temperature with 150 μL PBS for ~1 hr and then examined by reverse phase HPLC. The HPLC (not shown) showed 58% $^{18}$F unbound and 42% still attached to the peptide. The data indicate that $^{18}$F—Al-DTPA complex may be unstable when mixed with phosphate.

Reverse Phase HPLC—Reverse phase HPLC analysis was done under the following conditions:

Column: WATERS® XTERRA™ MS C$_{18}$ 5 μm, 4.6×250 mm
Flow Rate: 1 mL/min
Gradient Buffers Buffer C, 0.1% NH$_4$OAc in DI water, Buffer D, 90% acetonitrile 10% water and 0.1% NH$_4$OAc
Gradient: 100% Buffer C to 100% Buffer D using a linear gradient over 30 min.
Run Time: 30 min Size Exclusion HPLC—The size exclusion HPLC was done under the following conditions:

Column: BIORAD® BIO-SIL™ SEC 250, 300×7.8 mm
Gradient: Isocratic
Eluent Buffer: 0.2 M Phosphate pH 6.8
Flow Rate: 1 mL/min
Run Time: 30 min All radiometric traces were obtained using a PERKIN ELMER® 610Tr to monitor the emission of $^{18}$F. Tables 2-4 are tabular representations of the data.

TABLE 2

$^{18}$F + IMP 272 + AlCl$_3$ heated at 110° C. for 15 min, followed by analysis by reverse phase HPLC.
Regions: $^{18}$F Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 130.0 | | | |
| Region 1 | 2.30 | 3.30 | 2.60 | 85270.0 | 200050.0 | 93.15 | 96.31 |
| Bkg 2 | 4.40 | 4.50 | 4.40 | 210.0 | | | |
| Region 2 | 8.70 | 9.80 | 9.00 | 5590.0 | 14720.0 | 6.85 | 7.09 |
| 2 Peaks | | | | | 214770.0 | 100.00 | 103.40 |

TABLE 3

$^{18}$F + excess IMP 272 + AlCl$_3$ heated at 110° C. for 15 min, followed by analysis by reverse phase HPLC.
Regions: $^{18}$F Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 340.0 | | | |
| Region 1 | 2.40 | 3.20 | 2.70 | 6450.0 | 20549.6 | 7.76 | 8.23 |
| Bkg 2 | 7.10 | 7.20 | 7.10 | 630.0 | | | |
| Region 2 | 7.30 | 8.70 | 8.50 | 3140.0 | 13113.6 | 4.95 | 5.25 |
| Region 3 | 8.70 | 10.00 | 9.00 | 93700.0 | 231023.9 | 87.28 | 92.57 |
| Bkg 3 | 10.70 | 10.80 | 10.70 | 520.0 | | | |
| 3 Peaks | | | | | 264687.1 | 100.00 | 106.06 |

TABLE 4

Phosphate Challenge in PBS for 90 min at room temp. Aliquot of $^{18}F$ + excess IMP 272 + $AlCl_3$ heated at 110° C. for 15 min and analyzed by reverse phase HPLC.
Regions: $^{18}F$ Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.00 | 2.10 | 2.00 | 350.0 | | | |
| Region 1 | 2.40 | 3.30 | 2.70 | 81930.0 | 162403.6 | 58.23 | 62.44 |
| Bkg 2 | 4.20 | 4.30 | 4.20 | 410.0 | | | |
| Bkg 3 | 7.50 | 7.60 | 7.50 | 780.0 | | | |
| Region 2 | 7.80 | 8.60 | 8.40 | 2110.0 | 5564.7 | 2.00 | 2.14 |
| Region 3 | 8.60 | 9.80 | 8.90 | 44590.0 | 110942.0 | 39.78 | 42.66 |
| Bkg 4 | 10.50 | 10.60 | 10.50 | 460.0 | | | |
| 3 Peaks | | | | | 278910.3 | 100.00 | 107.24 |

The labeled peptide was purified by applying the labeled peptide solution onto a 1 cc (30 mg) WATERS® HLB column (Part #186001879) and washing with 300 µL water to remove unbound F-18. The peptide was eluted by washing the column with 2×100 µL 1:1 EtOH/$H_2O$. The purified peptide was incubated in water at 25° C. and analyzed by reverse phase HPLC (not shown). The HPLC analysis showed that the $^{18}F$-labeled IMP 272 was not stable in water. After 40 min incubation in water about 17% of the $^{18}F$ was released from the peptide, while 83% was retained (not shown).

Example 2

Immunoreactivity of $^{18}F$ IMP 272

The peptide (16 µL 2 mM IMP 272, 48 µg) was labeled with $^{18}F$ and analyzed for antibody binding by size exclusion HPLC. The size exclusion HPLC showed that the peptide bound hMN-14×679 but did not bind to the irrelevant bispecific antibody hMN-14×734 (not shown).

Example 3

IMP 272 $^{18}F$ Labeling with Other Metals

A ~3 µL aliquot of the metal stock solution ($6\times10^{-9}$ mol) was placed in a polypropylene cone vial and mixed with 75 µL $^{18}F$ (as received), incubated at room temperature for ~2 min and then mixed with 20 µL of a 2 mM ($4\times10^{-8}$ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown). These results demonstrate that the $^{18}F$ metal labeling technique is not limited to an aluminum ligand, but can also utilize other metals as well. With different metal ligands, different chelating moieties may be utilized to optimize binding of an F-18-metal conjugate.

Example 4

Standard $^{18}F$ Peptide Labeling Conditions Used to Screen Other Peptides For Al—$^{18}F$ Binding A 3 µL aliquot of the 2 mM aluminum stock solution was placed in a polypropylene cone vial and mixed with 50 µL $^{18}F$ (as received), incubated at room temperature for ~2 min and then mixed with 16 to 20 µL of a 2 mM peptide solution in 0.1 M NaOAc pH 4 buffer. The solution was heated in a heating block at 100° C. for 15 min and analyzed by reverse phase HPLC (PHENOMENEX™, GEMINI®, 5 µL, C-18, 110A, 250×4.6 mm HPLC Column).

Peptides Tested
 IMP 272: DTPA-Gln-Ala-Lys(HSG)-D-Tyr-Lys(HSG)-$NH_2$ $MH^+$ 1512
 IMP 288 DOTA-D-Tyr-D-Lys(HSG)-D-Glu-D-Lys(HSG)-$NH_2$ $MH^+$ 1453
 IMP 326 DTPA-ITC-NH—NH-Phe-CO-D-Tyr-D-Lys(HSG)-D-Glu-D-Lys(HSG)-$NH_2$ $MH^+$ 1477
 IMP 329 Deferoxamine-NH—CS—NH—NH-Ph-CO-D-Tyr-D-Lys(HSG)-D-Glu-D-Lys(HSG)-$NH_2$ $MH^+$ 1804
 IMP 331 NTA-iAsp-D-Ala-D-Lys(HSG)-D-Tyr-D-Lys(HSG)-$NH_2$ $MH^+$ 1240
 IMP 332 EDTADpr-D-Ala-D-Lys(HSG)-D-Ala-D-Lsy(HSG)-$NH_2$ $MH^+$ 1327
 IMP 333 DTPA-Dpr(DTPA)-D-Ala-D-Lys(HSG)-D-Ala-D-Lys(HSG)-$NH_2$ $MH^+$ 1845
 IMP 334 $(H203P)_2$—C(OH)—$(CH_2)_3$—NH-Gly-D-Lys(HSG)-D-Glu-D-Lys(HSG)-$NH_2$ $MH^+$ 1192
 IMP 337 Ac-D-Ser($PO_3H_2$)-D-Ser($PO_3H_2$)-D-Ala-D-Lys(HSG)-D-Ala-D-Lys(HSG)-$NH_2$ $MH^+$ 1291
 IMP 338 Ac-D-Ser($PO_3H_2$)-D-Ala-D-Lys(HSG)-D-Ala-D-Lys(HSG)-$NH_2$ $MH^+$ 1126
 IMP 345 DTPA-D-Ser($PO_3H_2$)-D-Ala-D-Lys(HSG)-D-Ala-D-Lys(HSG)-$NH_2$ $MH^+$ 1459
 IMP 349 DTPA-D-Cys(($H_2O_3P)_2$—CH—$CH_2$—S)-D-Ala-D-Lys(HSG)-D-Ala-D-Lys(HSG)-$NH_2$ $MH^+$ 1583
 IMP 361 DTPA-Dpr(BrCH$_2$CO—)-D-Ala-D-Lys(HSG)-D-Ala-D-Lys(HSG)-$NH_2$ $MH^+$ 1498
 IMP 366 DTPA-Dpr(Ph-S—$CH_2$CO—)-D-Ala-D-Lys(HSG)-D-Ala-D-Lys(HSG)-$NH_2$ $MH^+$ 1528
 IMP 368 Sym-DTPA-D-Ala-D-Lys(HSG)-D-Ala-D-Lys(HSG)-$NH_2$ $MH^+$ 1292
 IMP 369 Sym-DTPA-NH—CH(2-Br-Phe-)-$CH_2$—CO—D-Ala-D-Lys(HSG)-D-Ala-D-Lys(HSG)-$NH_2$ $MH^+$ 1517
 IMP 370 Sym-DTPA-NH—CH(2-$O_2$N-Phe-)-$CH_2$—CO— D-Ala-D-Lys(HSG)-D-Ala-D-Lys(HSG)-$NH_2$ $MH^+$ 1484
 IMP 371 DTPA-NH—CH(2-$O_2$N-Phe-)-$CH_2$—CO—D-Ala-D-Lys(HSG)-D-Ala-D-Lys(HSG)-$NH_2$ $MH^+$ 1484
 IMP 372 DTPA-Dpr(Ser)-D-Ala-D-Lys(HSG)-D-Ala-D-Lys(HSG)-$NH_2$ $MH^+$ 1465
 IMP 373 DTPA-Dpr(Sym-DTPA)-D-Ala-D-Lys(HSG)-D-Ala-D-Lys(HSG)-$NH_2$ $MH^+$ 1753
 IMP 374 DTPA-Dpr(Cl-$CH_2$CO-Cys(Et)-)-D-Ala-D-Lys(HSG)-D-Ala-D-Lys(HSG)—$NH_2$ $MH^+$ 1585
 IMP 375 DTPA-Dpr(2-Br-Phe-CHNH$_2$—$CH_2$—CO—)-D-Ala-D-Lys(HSG)-D-Ala-D-Lys(HSG)-$NH_2$ $MH^+$ 1603

IMP 376 DTPA-Cys(HO₃S—S)-D-Tyr-D-Ala-D-Lys(HSG)-D-Ala-D-Lys(HSG)-NH₂ MH⁺ 1558

IMP 379 DTPA-Dpr(2-H₂N-Phe-CO—)-D-Ala-D-Lys(HSG)-D-Ala-D-Lys(HSG)-NH₂ MH⁺ 1497

IMP 382 DTPA-Dpr(H)-D-Ala-D-Lys(HSG)-D-Ala-D-Lys(HSG)-NH₂ MH⁺ 1378

IMP 383 DTPA-Dpr(Gla-)-D-Ala-D-Lys(HSG)-D-Ala-D-Lys(HSG)-NH₂ MH⁺ 1507

IMP 384 DTPA-Dpr(2-HO-Phe-CHNH₂—CH₂—CO—)-D-Ala-D-Lys(HSG)-D-Ala-D-Lys(HSG)-NH₂ MH⁺ 1541

IMP 385 DTPA-Dpr(Dpr)-D-Ala-D-Lys(HSG)-D-Ala-D-Lys(HSG)-NH₂ MH⁺ 1464

IMP 386 DTPA-Dpr(2-pyridyl-CH₂—CHNH₂—CO—)-D-Ala-D-Lys(HSG)-D-Ala-D-Lys(HSG)-NH₂ MH⁺ 1526

IMP 387 DTPA-Dpr(D-9-anthrylalanine)-D-Ala-D-Lys(HSG)-D-Ala-D-Lys(HSG)-NH₂ MH⁺ 1625

IMP 389 DTPA-Dpr(2-carboxy piperizinyl)-D-Ala-D-Lys(HSG)-D-Ala-D-Lys(HSG)-NH₂ MH⁺ 1490

IMP 422
IMP 422 MH⁺1657

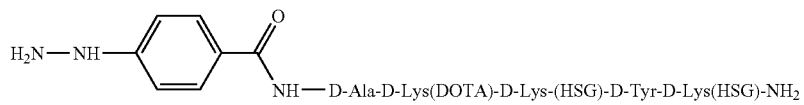

IMP 426
IMP 426 MH⁺1596

IMP 428
IMP 428 MH⁺1716

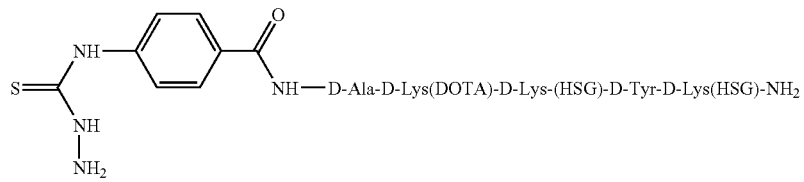

IMP 449 NOTA-ITC benzyl-D-Ala-D-Lys(HSG)-D-Tyr-D-Lys(HSG)-NH₂ MH⁺ 1459

IMP 460 NODA-GA-D-Ala-D-Lys(HSG)-D-Tyr-D-Lys(HSG)-NH₂ MH⁺ 1366

In an alternative configuration for a NOTA type ligand. The NOTA moiety could be made from D or L para-nitrophenylalanine and the iminodiacetic acid portion would come from diaminopropionic acid, which could be D or L. Furthermore, the position of the ethylene bridge could be switched with the diaminopropionic acid to give a different configuration of groups on the ligand. All of these modifications could affect binding kinetics and stability of the complex, which is subsequently formed. Alternatively, a NODA-Ga peptide could be labeled with, for example, $^{68}$Ga or $^{18}$F.

In certain embodiments, alternative chelating moieties may be used to bind to metal-$^{18}$F complexes. Some exemplary potential chelating moieties are based on the structure of NETA. As discussed above, Chong et al. (2007) report that NETA ligands may show improved serum stability when complexed with various metals. Chelator design may also be optimized to increase the binding affinity of the peptide for metal-$^{18}$F.

Results of Peptide Labeling Screening Study

Most of the DTPA derivatives showed labeling comparable to the labeling of IMP 272. There were exceptions, IMP 349, bearing the bisphosphonate group on a cysteine side chain, labeled very poorly. The DOTA ligand did not bind the Al$^{18}$F. The ITC DTPA ligand of IMP 326 did not bind the Al$^{18}$F as well as DTPA. The NTA ligand of IMP 331 did not bind the Al$^{18}$F. The EDTA ligand of IMP 332 bound the A $^{18}$F but not as well as the DTPA. Symmetrical DTPA ligand did not bind the A $^{18}$F. The phosphonates and phosphate groups tested did not bind A $^{18}$F well under the conditions tested.

The screen did show that a group that was attached near the DTPA could influence the stability of the Al$^{18}$F-DTPA complex. The screen showed that IMP 375 labeled better and formed a complex that was significantly more stable than IMP 272. IMP 375 labeled well and was stable in water, showing 95.4% remaining bound after 5 hours at 25° C. (not shown).

For in vivo use a peptide with high serum stability would be preferred. The peptide labeling screening study only looked at the binding of Al$^{18}$F. Some of the peptides that did not label well with Al$^{18}$F might label better with another metal binding to the $^{18}$F.

Peptide Synthesis

The peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (US Patent Application Pub. No. US 2005/0002945 A1, application Ser. No. 10/776,470, the Examples section of which is incorporated herein by reference).

The tri-t-butyl DOTA, symmetrical tetra-t-butyl DTPA, ITC-benzyl DTPA, p-SCN-Bn-NOTA and TACN were obtained from MACROCYCLICS® (Dallas, Tex.). The DiB-ocTACN, NODA-GA(tBu)$_3$ and the NO2AtBu were purchased from CheMatech (Dijon, France). The Aloc/Fmoc Lysine and Dap (diaminopropionic acid derivatives (also Dpr)) were obtained from CREOSALUS® (Louisville, Ky.) or BACHEM® (Torrance, Calif.). The Sieber Amide resin was obtained from NOVABIOCHEM® (San Diego, Calif.). The remaining Fmoc amino acids were obtained from CREOSALUS®, BACHEM®, PEPTECH® (Burlington, Mass.), EMD BIOSCIENCES® (San Diego, Calif.), CHEM IMPEX® (Wood Dale, Ill.) or NOVABIOCHEM®. The aluminum chloride hexahydrate was purchased from SIGMA-ALDRICH® (Milwaukee, Wis.). The remaining solvents and reagents were purchased from FISHER SCIENTIFIC® (Pittsburgh, Pa.) or Sigma-Aldrich® (Milwaukee, Wis.). $^{18}$F was supplied by IBA MOLECULAR® (Somerset, N.J.)

IMP 272 was synthesized as described (McBride et al., US Patent Application Publ. No. 20040241158 A1, application Ser. No. 10/768,707, the Examples section of which is incorporated herein by reference). IMP 288 was made as described (McBride et al., J. Nucl. Med. 2006, 47:1678-1688).

IMP 326 The hydrazine peptide (IMP 319) was made on Sieber amide resin using Fmoc-D-Lys(Aloc)-OH, Fmoc-D-Glu(OBut)-OH, Fmoc-D-Lys(Aloc)-OH, Fmoc-D-Tyr(But)-OH and 4-(Boc-NH—NH—)C$_6$H$_4$—CO$_2$H in that order. The 4-(Boc-NH—NH—)C$_6$H$_4$—CO$_2$H was made by adding Boc dicarbonate to 4-hydrazinobenzoic acid in a dioxane sodium hydroxide solution.

After the addition of the Boc-hydrazide the side chain Aloc groups were removed and the Trityl-HSG-OH groups were added to the side chains of the lysines. The peptide was then cleaved from the resin with TFA and purified by HPLC to obtain the desired hydrazine bis-HSG peptide IMP 319 (MH$^+$ 1201). The hydrazide peptide (0.0914 g) was then mixed with 0.0650 g of ITC-Benzyl DTPA in 3 mL of 0.1 M sodium phosphate pH 8.2. The pH of the solution was adjusted with 1 M NaOH to keep the pH at pH 8.2. After the reaction between the peptide and the ITC-Benzyl DTPA was complete the peptide conjugate was purified by HPLC.

IMP 329 The deferoxamine isothiocyanate was prepared by mixing 1.0422 g of deferoxamine mesylate (1.59×10$^{-3}$ mol) with 0.2835 g (1.59×10$^{-3}$ mol) of thiocarbonyldiimidazole in 10 mL of 1:1 methanol/water. Triethylamine, 0.23 mL was added and the reaction was purified by reverse phase HPLC after 2.5 hr to obtain the deferoxamine isothiocyanate MNa$^+$ 625.

The hydrazine peptide, IMP 319, (0.0533 g, 4.4×10$^{-5}$ mol, MH$^+$ 1201) was mixed with 0.0291 g of deferoxamine isothiocyanate in a sodium phosphate buffer at pH 8.1 for two hours then purified by HPLC to afford the desired product MH+ 1804.

IMP 331 The following amino acids were attached to Sieber amide resin (0.58 mmol/g) in the order shown; Fmoc-D-Lys(Aloc)-OH, Fmoc-D-Tyr(But)-OH and Fmoc-D-Lys(Aloc)-OH. The Aloc groups were removed and Trt-HSG-OH was added to the side chains of the lysines. The Fmoc was removed, then Fmoc-D-Ala-OH and Fmoc-Asp-OBut were added in that order (0.5 g of resin). The Fmoc was removed and the nitrogen of the Asp was alkylated overnight with 3 mL t-butyl bromoacetate and 3.6 mL diisopropylethylamine in 3.4 mL of NMP. The peptide was cleaved from the resin with TFA and purified by reverse phase HPLC to obtain the desired peptide MH$^+$ 1240.

IMP 332 The peptide was made on 3 g of Sieber amide resin (0.58 mmol/g). The following amino acids were added to the resin in the order shown: Fmoc-D-Lys(Aloc)-OH, Fmoc-D-Tyr(But)-OH, Fmoc-D-Lys(Aloc)-OH, Fmoc-D-Ala-OH, and Fmoc-Dpr(Fmoc)-OH. The resin was split into portions for subsequent syntheses. One gram of the resin was removed and the Fmoc groups were removed from the diaminopropionic acid. The peptide was alkylated overnight with 3 mL t-butyl bromoacetate, 3.6 mL diisopropylethyl amine and 3.4 mL NMP. The side chain Aloc groups were then removed and the Trt-HSG-OH groups were added. The peptide was then cleaved from the resin and purified by HPLC to obtain the product MH$^+$ 1327.

IMP 333 The peptide was made with 1 g of the same resin that was used to make IMP 332. The DTPA tetra-t-butyl ester (U.S. Publ. No. 20050002945) was added to both of the amines of the Dpr group. The Aloc groups were then removed and the Trt-HSG-OH was added. The peptide was then cleaved and purified by HPLC to obtain the desired product MH$^+$ 1845.

IMP 334 The peptide was made on 1 g Rink amide resin (0.7 mmol/g) with the following amino acids added in the order shown: Fmoc-D-Lys(Aloc)-OH, Fmoc-D-Glu(But)-OH, Fmoc-D-Lys(Aloc)-OH, Boc-Ser(But)-OH, The Aloc groups were removed and the Trityl-HSG-OH was added. The peptide was cleaved from the resin with TFA. The crude peptide was collected by precipitation from ether and dried. Sodium periodate, 0.33 g, was dissolved in 15 mL water. The crude peptide was dissolved in 1 mL 0.5 M sodium phosphate pH 7.6, 3 mL water and 1 mL of the periodate solution. 3 mL more periodate in one milliliter increments was added over ~2 hr. The mixture was then purified by reverse phase HPLC and lyophilized to obtain the aldehyde IMP 289 HCO—CO-D-Lys(HSG)-D-Glu-D-Lys(HSG)-NH$_2$MH$^+$ 959. Alendronate (0.0295 g, CALBIOCHEM®) was dissolved in 150 µL 0.1 M NaOAc pH 4. The peptide, IMP 289, (0.0500 g) was dissolved in 100 µL of 13% isopropanol in water. Sodium cyanoborohydride was added and the mixture was purified by HPLC to afford the desired product MH$^+$ 1192.

IMP 337 & IMP 338 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, Fmoc-D-Ser(PO(OBzl)OH)—OH, and Ac$_2$O. The Aloc groups were removed and the Trt-HSG-OH groups were added to the side chains of the lysines. The peptide was cleaved from the resin and purified by HPLC to afford the desired products: IMP 337 MH$^+$ 1291 and IMP 338 MH$^+$ 1126.

IMP 345 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, and tetra-t-butyl DTPA. The Aloc groups were removed and the Trt-HSG-OH groups were added to the side chains of the lysines. The peptide was cleaved from the resin and purified by HPLC to afford the desired product: IMP 345 MH$^+$ 1459.

IMP 349 The peptide IMP 347 DTPA-D-Cys-D-Ala-D-Lys(HSG)-D-Tyr-D-Lys(HSG)-NH$_2$ was made on Sieber amide resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved Fmoc-D-Ala-OH, Fmoc-D-Cys(Trt)-OH and tetra-t-butyl DTPA were added. The peptide was cleaved from the resin and purified by HPLC to afford the desired product: IMP 347 MH$^+$ 1395. The peptide, IMP 347, 0.0446 g (3.2×10$^{-5}$ mol) was mixed with 0.4605 g (2.4×10$^{-3}$ mol) of ethenylidenebis (phosphonic acid) (Degenhardt et al., J. Org. Chem. 1986, 51:3488-3490) in 3 mL of water and the solution was adjusted to pH 6.5 with 1 M NaOH added dropwise. The reaction was stirred overnight and the reaction solution was adjusted to pH 1.49 by the addition of excess ethenylidenebis(phosphonic acid). The mixture was stirred overnight at room temperature and then purified by HPLC to obtain the desired peptide IMP 349 MH$^+$ 1583.

IMP 361 The peptide was made on Sieber amide resin using the following amino acids added in the order shown: Aloc-D-Lys(Fmoc)-OH, Trt-HSG-OH, the Aloc was cleaved, Fmoc-D-Ala-OH, Aloc-D-Lys(Fmoc)-OH, Trt-HSG-OH were added, the Aloc was cleaved, Fmoc-D-Ala-OH, Fmoc-Dap(Aloc)-OH and tetra-t-butyl DTPA were added. The Aloc on the side chain of the Dap was removed and bromo acetyl was added with bromo acetic anhydride. The crude product was purified by HPLC to obtain the desired peptide IMP 361 (MH$^+$ 1498).

IMP 366 The peptide was made by the same method as IMP 361 with phenylthioacetic acid added last. The crude product was purified by HPLC to afford the product IMP 366 MH$^+$ 1528.

IMP 368 The peptide was as described for IMP 349 except the cysteine residue was not added and symmetrical tetra-t-butylDTPA (MACROCYCLICS®) was used in place of the unsymmetrical DTPA to obtain the desired product after purification, IMP 368 MH$^+$ 1292.

IMP 369 The peptide was made as described for IMP 349 with Fmoc-R-3-amino-3-(2-bromophenyl)propionic acid added in place of the D-Cys and symmetrical tetra-t-butylDTPA added in place of the unsymmetrical version to the DTPA tetra-t-butyl ester. The crude peptide was purified to obtain the desired product, MH$^+$ 1517.

IMP 370 The peptide was made as described for IMP 369 except Fmoc-R-3-amino-3-(2-nitrophenyl) propionic acid was used instead of the bromo. The desired product was obtained after purification by HPLC MH$^+$ 1484.

IMP 371 The peptide was made as described for IMP 370 except the unsymmetrical tetra-t-butyl DTPA was used in place of the of the symmetrical version. The desired product was obtained after purification by HPLC MH$^+$ 1484.

IMP 372 The peptide was made as described for IMP 361 with Fmoc-Ser(But)-OH used to attach the Ser to the Dap side chain. The Fmoc was removed and the peptide was cleaved from the resin and purified to obtain the desired product MH$^+$ 1465.

IMP 373 The peptide was made as described for IMP 361 with symmetrical-tetra-t-butylester DTPA used to attach the Sym-DTPA to the Dap side chain. The peptide was cleaved from the resin and purified to obtain the desired product MH$^+$ 1753.

IMP 374 The peptide was made as described for IMP 361 with Fmoc-5-ethyl cysteine added to the Dap side chain followed by chloro acetyl (on the cysteine nitrogen) added via chloroacetic anhydride. The peptide was cleaved from the resin and purified to obtain the desired product MH$^+$ 1585.

IMP 375 The peptide was made as described for IMP 361 with Fmoc-R-3-amino-3-(2-bromophenyl)propionic acid added to the Dap side chain followed by cleavage of the Fmoc group. The peptide was cleaved from the resin and purified to obtain the desired product MH$^+$ 1603.

IMP 376 The peptide was made as described for IMP 361 with Fmoc-D-Tyr(But)-OH added after the second alanine followed by Fmoc-Cys(SO$_3$H) and tetra-t-butylDTPA. The peptide was cleaved from the resin and purified to obtain the desired product MH$^+$ 1558.

IMP 379 The peptide was made as described for IMP 361 with Boc-2-Abz-OH added to the side chain of the Dap. The peptide was cleaved from the resin and purified to obtain the desired product MH$^+$ 1497.

IMP 382 The peptide was made as described for IMP 361 with the Aloc removed from the side chain of the Dap. The peptide was cleaved from the resin and purified to obtain the desired product MH$^+$ 1378.

IMP 383 The peptide was made as described for IMP 361 with Fmoc-Gla(OBut)$_2$-OH added to the side chain of the Dap. The peptide was cleaved from the resin and purified to obtain the desired product MH$^+$—CO$_2$ 1507

IMP 384 The peptide was made as described for IMP 361 with Fmoc-Boc-S-3-amino-3-(2-hydroxyphenyl)propionic acid added to the side chain of the Dap. The peptide was cleaved from the resin and purified to obtain the desired product MH$^+$ 1541.

IMP 385 The peptide was made as described for IMP 361 with Fmoc-Dpr(Fmoc)-OH added to the side chain of the Dap. The peptide was cleaved from the resin and purified to obtain the desired product MH$^+$ 1464.

IMP 386 The peptide was made as described for IMP 361 with Boc-D-2-pyridylalanine-OH added to the side chain of the Dap. The peptide was cleaved from the resin and purified to obtain the desired product MH$^+$ 1526.

IMP 387 The peptide was made as described for IMP 361 with Fmoc-D-9-anthrylalanine-OH added to the side chain of the Dap. The peptide was cleaved from the resin and purified to obtain the desired product MH$^+$ 1625.

IMP 389 The peptide was made as described for IMP 361 with bis-Boc-piperazine-2-carboxylate added to the side chain of the Dap. The peptide was cleaved from the resin and purified to obtain the desired product MH$^+$ 1664.

Example 5

Alternative Methods for Preparing and Separating $^{18}$F-Labeled Peptides

In certain embodiments, heating was used to get the Al$^{18}$F complex into the NOTA chelating group. Alternatively, ITC benzyl NOTA (MACROCYCLICS®) could be labeled with Al$^{18}$F and then conjugated to other heat sensitive molecules, such as proteins, after labeling. If high specific activity is needed the ITC Benzyl NOTA complex can be purified away from the cold ligand.

Al$^{3+}$ as added to the peptide [IMP-449] and its HPLC profile compared to the uncomplexed NOTA peptide and the Al$^{18}$F peptide. With IMP 449 the Al peptide and the Al$^{18}$F peptides have virtually the same retention time ($t_R$) by HPLC, with ~1 min longer $t_R$ for the unlabeled peptide. The peptide was purified on a PHENOMENEX™ ONYX® monolithic C-18 100×4.5 mm column using a 3 mL/min flow rate. Buffer A was 0.1% TFA in water and Buffer B was 90% CH$_3$CN 10% water and 0.1% TFA. The linear gradient went from 100% buffer A to 75:25 A/B over 15 min. Since the Al complex co-elutes with the Al$^{18}$F complex, the amount of Al$^{3+}$ and $^{18}$F added will determine the specific activity.

IMP 449 was prepared according to Example 6 below and labeled as follows. The $^{18}$F was received in a 2.0 mL FISHER® microcentrifuge vial (02-681-374) containing 15 mCi of $^{18}$F in ~325 µL water. 3 µL of 2 mM AlCl$_3$ in 0.1 M pH 4 NaOAc was added to the $^{18}$F solution and then vortexed. After about 4 min, 10 µL of 0.05 M IMP 449 in pH 4 0.5 M NaOAc was added. The sample was vortexed again and heated in a 102° C. heating block for 17 min. The reaction was then cooled briefly and then the vial contents were removed and purified by HPLC as described above.

Separately, elution conditions were determined on the WATERS® ALLIANCE™ analytical system and the labeled peptide eluted between 7.5 and 8.5 min. The analytical HPLC showed that the labeled peptide contained the [AlF]IMP 449 (UV 220 nm) and did not contain the uncomplexed peptide, resulting in an increased specific activity.

The peptide was diluted in water and then pushed through a WATERS® OASIS PLUS HLB™ extraction column. The labeled peptide was eluted with 3 mL of 1:1 EtOH/$H_2O$. HPLC analysis of the eluents confirmed that the column efficiently trapped the labeled peptide, which allowed the acetonitrile and TFA to be washed away from the peptide. The HPLC also showed that 1:1 EtOH/$H_2O$ eluent contained the desired product free of loose $^{18}F$ in a solvent suitable for injection after dilution. Labeling yields were between 5-20% after HPLC purification. The specific activity of the HPLC purified peptide was estimated to be in the range of about 500 to 1300 Ci/mmol (not shown). We found subsequently that radiolabeling yields with this derivative could be improved 2- to 4-fold to 44% by reducing the reaction volume by one third.

Example 6

Production and Use of a Serum-Stable $^{18}F$-Labeled Peptide IMP 449

The peptide, IMP 448 D-Ala-D-Lys(HSG)-D-Tyr-D-Lys (HSG)-$NH_2$ $MH^+$ 1009 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757 g ($7.5 \times 10^{-5}$ mol) was mixed with 0.0509 g ($9.09 \times 10^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449.

$^{18}F$ Labeling of IMP 449

The peptide IMP 449 (0.002 g, $1.37 \times 10^{-6}$ mol) was dissolved in 686 μL (2 mM peptide solution) 0.1 M NaOAc pH 4.02. Three microliters of a 2 mM solution of Al in a pH 4 acetate buffer was mixed with 15 μL, 1.3 mCi of $^{18}F$. The solution was then mixed with 20 μL of the 2 mM IMP 449 solution and heated at 105° C. for 15 min. Reverse Phase HPLC analysis showed 35% ($t_R$~10 min) of the activity was attached to the peptide and 65% of the activity was eluted at the void volume of the column (3.1 min, not shown) indicating that the majority of activity was not associated with the peptide. The crude labeled mixture (5 μL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose $^{18}F$ Labeling

Further studies with purified IMP 449 demonstrated that the $^{18}F$-labeled peptide was highly stable (91%, not shown) in human serum at 37° C. for at least one hour and was partially stable (76%, not shown) in human serum at 37° C. for at least four hours. Additional studies were performed in which the IMP 449 was prepared in the presence of ascorbic acid as a stabilizing agent. In those studies (not shown), the metal-$^{18}F$-peptide complex showed no detectable decomposition in serum after 4 hr at 37° C. The mouse urine 30 min after injection of $^{18}F$-labeled peptide was found to contain $^{18}F$ bound to the peptide (not shown). These results demonstrate that the $^{18}F$-labeled peptides disclosed herein exhibit sufficient stability under approximated in vivo conditions to be used for $^{18}F$ imaging studies.

For studies in the absence of ascorbic acid, $^{18}F$~21 mCi in ~400 μL of water was mixed with 9 μL of 2 mM $AlCl_3$ in 0.1 M pH 4 NaOAc. The peptide, IMP 449, 60 μL (0.01 M, $6 \times 10^{-7}$ mol in 0.5 NaOH pH 4.13) was added and the solution was heated to 110° C. for 15 min. The crude labeled peptide was then purified by placing the reaction solution in the barrel of a 1 cc WATERS® HLB column and eluting with water to remove unbound $^{18}F$ followed by 1:1 EtOH/$H_2O$ to elute the $^{18}F$-labeled peptide. The crude reaction solution was pulled through the column into a waste vial and the column was washed with 3×1 mL fractions of water (18.97 mCi). The HLB column was then placed on a new vial and eluted with 2×200 μL 1:1 EtOH/$H_2O$ to collect the labeled peptide (1.83 mCi). The column retained 0.1 mCi of activity after all of the elutions were complete. An aliquot of the purified $^{18}F$-labeled peptide (20 μL) was mixed with 200 μL of pooled human serum and heated at 37° C. Aliquots were analyzed by reverse phase HPLC (as described above). The results showed the relative stability of $^{18}F$-labeled purified IMP 449 at 37° C. at time zero, one hour (91% labeled peptide), two hours (77% labeled peptide) and four hours (76% labeled peptide) of incubation in human serum (not shown). It was also observed that $^{18}F$-labeled IMP 449 was stable in TFA solution, which is occasionally used during reverse phase HPLC chromatography. There appears to be a general correlation between stability in TFA and stability in human serum observed for the exemplary $^{18}F$-labeled molecules described herein. These results demonstrate that $^{18}F$-labeled peptide, produced according to the methods disclosed herein, shows sufficient stability in human serum to be successfully used for in vivo labeling and imaging studies, for example using PET scanning to detect labeled cells or tissues. Finally, since IMP 449 peptide contains a thiourea linkage, which is sensitive to radiolysis, several products are observed by RP-HPLC. However, when ascorbic acid is added to the reaction mixture, the side products generated are markedly reduced.

Mass Spectroscopy

The Al and $Al^{19}F$ complexes of the peptide were prepared so that the complexes could be analyzed by HPLC and by mass spectroscopy to help determine the nature of the complexes formed. Two $Al^{19}F$ complexes were formed with retention times that matched the F complexes when examined under similar conditions. The mass of the [$Al^{19}F$] IMP 449 $MH^+$ 1502.6588 ($C_{66}H_{93}N_{19}O_{17}S_1Al_1F_1$ theoretical 1502.6589) is consistent with a complex, where the $Al^{19}F$ binds to two of the NOTA carboxyl groups and the third carboxyl is still protonated. Aluminum is known to bind NOTA to form hexadentate bonds to the three nitrogens and three carboxyls (Andre et al., 2002, J Inorg Biochem 88:1-6). Thus, it appears that the $Al^{19}F$ complex has pentadentate binding to NOTA with the sixth binding site of the aluminum filled with the fluoride ion.

Example 7

In Vivo Biodistribution of $^{18}$F-Labeled IMP 449 in SCID Mice $^{18}$F-labeled IMP 449 was prepared as described above. The material was purified on an OASIS® HLB column (WATERS®, Milford, Mass.). The unbound material was washed out with water and the labeled peptide that was bound to the column was eluted with 1:1 EtOH/H$_2$O mixture. Both fractions were analyzed by reverse phase C$_{18}$ HPLC. The purified peptide eluted as several peaks on the reverse HPLC column (not shown). The unbound fraction collected from the OASIS® column showed poor recovery, 7%, from the C$_{18}$ column (not shown).

TABLE 5

$^{18}$F "unbound" fraction at 20 min post injection: % ID/g mean and the individual animals.

| Tissue | n | Mean | SD | Animal 1 | Animal 2 | Animal 3 |
|---|---|---|---|---|---|---|
| Tumor | 1 | — | — | 0.902 | — | — |
| Liver | 3 | 2.056 | 0.244 | 1.895 | 2.338 | 1.937 |
| Spleen | 3 | 1.869 | 0.434 | 1.677 | 2.366 | 1.564 |
| Kidney | 3 | 4.326 | 0.536 | 3.931 | 4.936 | 4.111 |
| Lung | 3 | 2.021 | 0.149 | 1.903 | 2.188 | 1.972 |
| Blood | 3 | 2.421 | 0.248 | 2.355 | 2.696 | 2.212 |
| Stomach | 3 | 0.777 | 0.409 | 0.421 | 1.224 | 0.687 |
| Small Int. | 3 | 2.185 | 0.142 | 2.042 | 2.325 | 2.187 |
| Large Int. | 3 | 1.403 | 0.069 | 1.482 | 1.356 | 1.372 |
| Femur | 3 | 11.688 | 1.519 | 11.502 | 13.292 | 10.270 |
| Spine | 3 | 14.343 | 2.757 | 17.506 | 13.072 | 12.452 |
| Muscle | 3 | 1.375 | 0.160 | 1.191 | 1.457 | 1.478 |

TABLE 6

[Al$^{18}$F] IMP 449 purified, 80 µCi, 1 × 10$^{-8}$ mol at 20 min post injection: % ID/g mean and the individual animals

| Tissue | n | Mean | SD | Animal 1 | Animal 2 | Animal 3 | Animal 4 | Animal 5 |
|---|---|---|---|---|---|---|---|---|
| Tumor | 1 | — | — | 0.891 | — | — | — | — |
| Liver | 5 | 2.050 | 0.312 | 1.672 | 1.801 | 2.211 | 2.129 | 2.440 |
| Spleen | 5 | 1.297 | 0.259 | 0.948 | 1.348 | 1.144 | 1.621 | 1.425 |
| Kidney | 5 | 12.120 | 4.128 | 8.354 | 7.518 | 12.492 | 15.535 | 16.702 |
| Lung | 5 | 2.580 | 0.518 | 2.034 | 2.103 | 2.804 | 2.678 | 3.278 |
| Blood | 5 | 3.230 | 0.638 | 2.608 | 2.524 | 3.516 | 3.512 | 3.992 |
| Stomach | 5 | 1.017 | 0.907 | 0.805 | 0.775 | 0.344 | 0.557 | 2.605 |
| Small Int. | 5 | 1.212 | 0.636 | 0.896 | 0.921 | 0.927 | 0.967 | 2.349 |
| Large Int. | 5 | 0.709 | 0.220 | 0.526 | 0.568 | 0.599 | 0.793 | 1.057 |
| Femur | 5 | 0.804 | 0.389 | 0.314 | 0.560 | 1.280 | 0.776 | 1.087 |
| Spine | 5 | 3.915 | 6.384 | 0.819 | 0.923 | 1.325 | 1.177 | 15.330# |
| Muscle | 5 | 0.668 | 0.226 | 0.457 | 0.439 | 0.960 | 0.673 | 0.814 |

High spine uptake in Animal #5 was confirmed by recounting.

The "unbound" fraction and the purified [Al$^{18}$F] IMP 449 were injected into SCID mice that were previously injected with sc SU-DHL6 lymphoma cells. Only a few of the mice had visible tumors. Biodistribution data showed a significant difference between the "unbound" $^{18}$F fraction and the purified [Al$^{18}$F] IMP 449. Data are shown in Tables 5-7 below. Note that in this study, no pretargeting bispecific antibodies were administered to the animals before the labeled peptide. These results demonstrate the distribution of labeled peptide vs free $^{18}$F in vivo.

Unconjugated $^{18}$F shows a high level of distribution to bone tissue in vivo. Uptake 20 minutes after injection was, as expected, seen primarily in the bone (spine), with about 12-15% injected dose per gram (ID/g), followed by the kidneys with about 4% ID/g. Localization of the $^{18}$F label to bone tissue was substantially decreased by conjugation to a targeting peptide. When bound to IMP 449, uptake in the bone is reduced to ~1% ID/g at 20 min and 0.3% at 1 h after injection, with renal uptake of 11% at 20 min and 3.3% ID/g at 1 hr. Renal uptake of the peptide alone was similar to that of the pretargeted [Al$^{18}$F] IMP 449 peptide (see following Example), suggesting its uptake was a function of the peptide rather than a consequence of the animals having been give the bsMAb 18 h earlier. Relatively low non-specific uptake was observed in the spine and femur with the $^{18}$F-labeled peptide compared with unbound $^{18}$F.

TABLE 7

[Al$^{18}$F] IMP 449 purified, 80 µCi, 1 × 10$^{-8}$ mol at 1 h post injection: % ID/g mean and the individual animals

| Tissue | n | Mean | SD | Animal 1 | Animal 2 | Animal 3 | Animal 4 |
|---|---|---|---|---|---|---|---|
| Tumor | 1 | 0.032 | 0.064 | 0.000 | 0.127 | 0.000 | 0.000 |
| Liver | 4 | 0.883 | 0.308 | 1.103 | 0.632 | 0.604 | 1.191 |
| Spleen | 4 | 1.061 | 0.702 | 1.598 | 0.631 | 0.301 | 1.713 |
| Kidney | 4 | 3.256 | 0.591 | 3.606 | 2.392 | 3.362 | 3.666 |
| Lung | 4 | 0.324 | 0.094 | 0.411 | 0.232 | 0.256 | 0.399 |
| Blood | 4 | 0.285 | 0.104 | 0.378 | 0.153 | 0.250 | 0.358 |
| Stomach | 4 | 0.152 | 0.082 | 0.225 | 0.041 | 0.199 | 0.142 |
| Small Int. | 4 | 1.290 | 0.228 | 1.124 | 1.247 | 1.166 | 1.624 |
| Large Int. | 4 | 0.115 | 0.035 | 0.167 | 0.091 | 0.094 | 0.109 |
| Femur | 4 | 1.006 | 0.876 | 2.266 | 0.448 | 0.939 | 0.374 |
| Spine | 4 | 0.314 | 0.076 | 0.423 | 0.257 | 0.268 | 0.306 |
| Muscle | 4 | 0.591 | 0.946 | 0.205 | 0.077 | 2.008 | 0.075 |

These results demonstrate that the $^{18}$F-labeled peptide showed sufficient in vivo stability to perform labeling and imaging studies.

Example 8

Preparation of DNL Constructs for $^{18}$F Imaging by Pretargeting

In various forms, the DNL technique may be used to make dimers, trimers, tetramers, hexamers, etc. comprising virtually any antibodies or fragments thereof or other effector moieties. For certain preferred embodiments, IgG antibodies or Fab antibody fragments may be produced as fusion proteins containing either a DDD or AD sequence. Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. For purposes of $^{18}$F detection, an antibody or fragment containing a binding site for an antigen associated with a target tissue to be imaged, such as a tumor, may be combined with a second antibody or fragment that binds a hapten on a targetable construct, such as IMP 449, to which a metal-$^{18}$F can be attached. The bispecific antibody (DNL construct) is administered to a subject, circulating antibody is allowed to clear from the blood and localize to target tissue, and the $^{18}$F-labeled targetable construct is added and binds to the localized antibody for imaging.

Independent transgenic cell lines may be developed for each Fab or IgG fusion protein. Once produced, the modules can be purified if desired or maintained in the cell culture supernatant fluid. Following production, any DDD$_2$-fusion protein module can be combined with any AD-fusion protein module to generate a bispecific DNL construct. For different types of constructs, different AD or DDD sequences may be utilized.

```
DDD1:
SHIQIPPGLTELLQGYTVEVLRQQPPDLVEFAVEYF    (SEQ ID NO: 3)
TRLREARA

DDD2:
CGHIQIPPGLTELLQGYTVEVLRQQPPDLVEFAVEY    (SEQ ID NO: 4)
FTRLREARA

AD1:
QIEYLAKQIVDNAIQQA                        (SEQ ID NO: 5)

AD2:
CGQIEYLAKQIVDNAIQQAGC                    (SEQ ID NO: 6)
```

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC) followed by four glycines and a serine, with the final two codons (GS) comprising a Bam HI restriction site. The 410 bp PCR amplimer was cloned into the pGemT PCR cloning vector (Promega, Inc.) and clones were screened for inserts in the T7 (5') orientation.

Construction of (G$_4$S)$_2$DDD1 ((G$_4$S)$_2$ disclosed as SEQ ID NO: 22)

A duplex oligonucleotide, designated (G$_4$S)$_2$DDD1 ((G$_4$S)$_2$ disclosed as SEQ ID NO: 22), was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

```
GSGGGGSGGGGSHIQIPPGLTELLQGYTVEVLRQQP    (SEQ ID NO: 7)
PDLVEFAVEYFTRLREARA
```

Two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into pGemT and screened for inserts in the T7 (5') orientation.

Construction of (G$_4$S)-2-AD1 ((G$_4$S)$_2$ disclosed as SEQ ID NO: 22)

A duplex oligonucleotide, designated (G$_4$S)$_2$-AD1 ((G$_4$S)$_2$ disclosed as SEQ ID NO: 22), was synthesized (Sigma Genosys) to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

```
GSGGGGSGGGGSQIEYLAKQIVDNAIQQA    (SEQ ID NO: 8)
```

Two complimentary overlapping oligonucleotides encoding the above peptide sequence, designated AKAP-IS Top and AKAP-IS Bottom, were synthesized and annealed. The duplex was amplified by PCR. The amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD I coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide (GGGGSGGGCG, SEQ ID NO:9) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

H679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions (not shown). Reducing SDS-PAGE shows that any additional bands apparent in the non-reducing gel are product-related (not shown), as only bands representing the constituent polypeptides of TF2 are evident. However, the relative mobilities of each of the four polypeptides are too close to be resolved. MALDI-TOF mass spectrometry (not shown) revealed a single peak of 156,434 Da, which is within 99.5% of the calculated mass (157,319 Da) of TF2.

The functionality of TF2 was determined by BIACORE assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Production of TF10 Bispecific Antibody

A similar protocol was used to generate a trimeric TF10 DNL construct, comprising two copies of a C-DDD2-Fab-hPAM4 and one copy of C-AD2-Fab-679. The cancer-targeting antibody component in TF10 is derived from hPAM4, a humanized anti-pancreatic cancer mucin MAb that has been studied in detail as a radiolabeled MAb (e.g., Gold et al., *Clin. Cancer Res.* 13: 7380-7387, 2007). The hapten-binding component is derived from h679, a humanized anti-histaminyl-succinyl-glycine (HSG) MAb discussed above. The TF10 bispecific ([hPAM4]$_2$×h679) antibody was produced using the method disclosed for production of the (anti CEA)$_2$× anti HSG bsAb TF2, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

A full tissue histology and blood cell binding panel has already been examined for hPAM4 IgG and for an anti-CEA× anti-HSG bsMAb that is entering clinical trials. hPAM4 binding was restricted to very weak binding to the urinary bladder and stomach in 1/3 specimens (no binding was seen in vivo), and no binding to normal tissues was attributed to the anti-CEA×anti-HSG bsMAb. Furthermore, in vitro studies against cell lines bearing the H1 and H2 histamine receptors showed no antagonistic or agonistic activity with the IMP 288 di-HSG peptide, and animal studies in 2 different species showed no pharmacologic activity of the peptide related to the histamine component at doses 20,000 times higher than that used for imaging. Thus, the HSG-histamine derivative does not have pharmacologic activity.

Example 9

Sequence Variants for DNL

In certain preferred embodiments, the AD and DDD sequences incorporated into the cytokine-MAb DNL complex comprise the amino acid sequences of AD2 and DDD2, as indicated below.

```
DDD2
CGHIQIPPGLTELLQGYTVEVLRQQPPDLVEFAVEY    (SEQ ID NO: 4)
FTRLREARA

AD2
CGQIEYLAKQIVDNAIQQAGC                   (SEQ ID NO: 6)
```

However, in alternative embodiments sequence variants of AD and/or DDD moieties may be utilized in construction of the DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:3 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

Human DDD Sequence from Protein Kinase A

```
SHIQIPPGLTELLQGYTVEVLRQQPPDLVEFAVEYF    (SEQ ID NO: 3)
TRLREAPA
```

Alto et al. (2003) performed a bioinformatic analysis of the AD sequence of various AKAP proteins to design an RII selective AD sequence called AKAP-IS (SEQ ID NO:5), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:5. The skilled artisan will realize that in designing sequence variants of the AD sequence, one would desirably avoid changing any of the underlined residues, while conservative amino acid substitutions might be made for residues that are less critical for DDD binding.

```
AKAP-IS sequence
QIEYLAKQIVDNAIQQA                       (SEQ ID NO: 5)
```

Gold (2006) utilized crystallography and peptide screening to develop a SuperAKAP-IS sequence (SEQ ID NO:10), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:11-13. Substitutions relative to the AKAP-IS sequence are underlined. It is anticipated that, as with the AD2 sequence shown in SEQ ID NO:6, the AD moiety may also include the additional N-terminal residues cysteine and glycine and C-terminal residues glycine and cysteine, as shown in SEQ ID NO:6.

```
SuperAKAP-IS
QIEYVAKQIVDYAIHQA            (SEQ ID NO: 10)

Alternative AKAP sequences
QIEYKAKQIVDHAIHQA            (SEQ ID NO: 11)

QIEYHAKQIVDHAIHQA            (SEQ ID NO: 12)

QIEYVAKQIVDHAIHQA            (SEQ ID NO: 13)
```

Stokka et al. (2006) also developed peptide competitors of AKAP binding to PKA, shown in SEQ ID NO:14-16. The peptide antagonists were designated as Ht31 (SEQ ID NO:14), RIAD (SEQ ID NO:15) and PV-38 (SEQ ID NO:16). The Ht-31 peptide exhibited a greater affinity for the RII isoform of PKA, while the RIAD and PV-38 showed higher affinity for RI.

```
Ht31
DLIEEAASRIVDAVIEQVKAAGAY     (SEQ ID NO: 14)

RIAD
LEQYANQLADQIIKEATE           (SEQ ID NO: 15)

PV-38
FEELAWKIAKMIWSDVFQQC         (SEQ ID NO: 16)
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:5). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:17-19.

```
AKAP-IS
QIEYLAKQIVDNAIQQA            (SEQ ID NO: 5)

AKAP7δ-wt-pep
PEDAELVRLSKRLVENAVLKAVQQY    (SEQ ID NO: 17)

AKAP7δ-L304T-pep
PEDAELVRTSKRLVENAVLKAVQQY    (SEQ ID NO: 18)

AKAP7δ-L308D-pep
PEDAELVRLSKRDVENAVLKAVQQY    (SEQ ID NO: 19)
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:3. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
SHIQIPPGLTELLQGYTVEVLRQQPPDLVEFAVEYF (SEQ ID NO: 3)
TRLREARA
```

Example 10

In Vivo Studies With Pretargeting Antibody and $^{18}$F-Labeled Peptide $^{18}$F-labeled IMP 449 was prepared as follows. The $^{18}$F, 54.7 mCi in ~0.5 mL was mixed with 3 µL 2 mM Al in 0.1 M NaOAc pH 4 buffer. After 3 min 10 µL of 0.05 M IMP 449 in 0.5 M pH 4 NaOAc buffer was added and the reaction was heated in a 96° C. heating block for 15 min. The contents of the reaction were removed with a syringe. The crude labeled peptide was then purified by HPLC on a $C_{18}$ column. The flow rate was 3 mL/min. Buffer A was 0.1% TFA in water and Buffer B was 90% acetonitrile in water with 0.1% TFA. The gradient went from 100% A to 75/25 A:B over 15 min. There was about 1 min difference in retention time ($t_R$) between the labeled peptide, which eluted first and the unlabeled peptide. The HPLC eluent was collected in 0.5 min (mL) fractions. The labeled peptide had a $t_R$ between 6 to 9 min depending on the column used. The HPLC purified peptide sample was further processed by diluting the fractions of interest two fold in water and placing the solution in the barrel of a 1 cc WATERS® HLB column. The cartridge was eluted with 3×1 mL water to remove acetonitrile and TFA followed by 400 µL 1:1 EtOH/H$_2$O to elute the $^{18}$F-labeled peptide. The purified [Al$^{18}$F] IMP 449 eluted as a single peak on an analytical HPLC $C_{18}$ column (not shown).

Taconic nude mice bearing the four slow-growing sc CaPan1 xenografts were used for in vivo studies. Three of the mice were injected with TF10 (162 µg) followed with [Al$^{18}$F] IMP 449 18 h later. TF10 is a humanized bispecific antibody of use for tumor imaging studies, with divalent binding to the PAM-4 defined tumor antigen and monovalent binding to HSG (see, e.g., Gold et al., 2007, J. Clin. Oncol. 25(18S): 4564). One mouse was injected with peptide alone. All of the mice were necropsied at 1 h post peptide injection. Tissues were counted immediately. Animal #2 showed high counts in the femur. The femur was transferred into a new vial and was recounted along with the old empty vial. Recounting indicated that the counts were on the tissue. This femur was broken and had a large piece of muscle attached to it. Comparison of mean distributions showed substantially higher levels of $^{18}$F-labeled peptide localized in the tumor than in any normal tissues in the presence of tumor-targeting bispecific antibody.

Tissue uptake was similar in animals given the [Al$^{18}$F] IMP 449 alone or in a pretargeting setting (Table 8). Uptake in the human pancreatic cancer xenograft, CaPan1, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

TABLE 8

Tissue uptake at 1 h post peptide injection, mean and the individual animals:

| Tissue | | TF10 (162 μg) -→ 18 h → [Al$^{18}$F] IMP 449 (10:1) | | | | [Al$^{18}$F] IMP 449 alone |
|---|---|---|---|---|---|---|
| | n | Mean | SD | Animal 1 | Animal 2 | Animal 3 | Animal 1 |

| Tissue | n | Mean | SD | Animal 1 | Animal 2 | Animal 3 | [Al$^{18}$F] IMP 449 alone Animal 1 |
|---|---|---|---|---|---|---|---|
| Tumor (mass) | 3 | 4.591 | 0.854 | 4.330 (0.675 g) | 5.546 (0.306 g) | 3.898 (0.353 g) | 0.893 (0.721 g) |
| Liver | 3 | 0.197 | 0.041 | 0.163 | 0.242 | 0.186 | 0.253 |
| Spleen | 3 | 0.202 | 0.022 | 0.180 | 0.224 | 0.200 | 0.226 |
| Kidney | 3 | 5.624 | 0.531 | 5.513 | 6.202 | 5.158 | 5.744 |
| Lung | 3 | 0.421 | 0.197 | 0.352 | 0.643 | 0.268 | 0.474 |
| Blood | 3 | 0.196 | 0.028 | 0.204 | 0.219 | 0.165 | 0.360 |
| Stomach | 3 | 0.123 | 0.046 | 0.080 | 0.172 | 0.118 | 0.329 |
| Small Int. | 3 | 0.248 | 0.042 | 0.218 | 0.295 | 0.230 | 0.392 |
| Large Int. | 3 | 0.141 | 0.094 | 0.065 | 0.247 | 0.112 | 0.113 |
| Pancreas | 3 | 0.185 | 0.078 | 0.259 | 0.194 | 0.103 | 0.174 |
| Spine | 3 | 0.394 | 0.427 | 0.140 | 0.888 | 0.155 | 0.239 |
| Femur | 3 | 3.899 | 4.098 | 2.577 | 8.494 | 0.625 | 0.237 |
| Brain | 3 | 0.064 | 0.041 | 0.020 | 0.072 | 0.100 | 0.075 |
| Muscle | 3 | 0.696 | 0.761 | 0.077 | 1.545 | 0.465 | 0.162 |

Example 11

Comparison of Biodistribution of $^{111}$In-IMP 449 Vs [Al$^{18}$F] IMP 449 with Pretargeting Antibody The goal of the study was to compare biodistribution of $^{111}$In-IMP 449 and [Al$^{18}$F] IMP 449 in nude mice bearing sc LS174 T xenografts after pretargeting with bispecific antibody TF2. TF2 antibody was made by the dock-and-lock method and contains binding sites for the CEA tumor antigen and the HSG hapten (see, e.g., Sharkey et al., Radiology 2008, 246:497-507; Rossi et al., PNAS USA 2006, 103:6841-46). Since there were insufficient numbers of mice with tumors at one time, the study was performed during 2 different weeks.

$^{111}$In-IMP 449: $^{111}$In labeling was performed using a procedure similar to the one used for labeling IMP 288, except at lower specific activity. ITLC and C-$_{18}$ RP-HPLC showed ~30% unbound (not shown). The labeled peptide was purified on an HLB column (1 mL, 30 mg). The analyses of the purified product again showed 33% unbound by ITLC developed in saturated sodium chloride (not shown). RP-HPLC showed multiple peaks before and after purification (not shown). SE-HPLC after purification showed 47% of the activity shift to high MW when mixed with 20× molar excess of TF2 (not shown).

[Al$^{18}$F] IMP 449: Labeling was performed as described above except the $^{18}$F was purified on a QMA cartridge before labeling as described by Kim et. al. (Applied Radiation and Isotopes 61, 2004, 1241-46). Briefly, the SEP-PAK® LIGHT WATERS® ACCELL™ Plus QMA Cartridge was prepared flushed with 10 mL 0.4 M KHCO$_3$ and then washed with 10 mL DI water. The $^{18}$F (42 mCi) in 2 mL water was loaded onto the QMA cartridge. The cartridge was eluted with 10 mL DI water to remove impurities. The column was then eluted with 1 mL 0.4 M KHCO$_3$ in 200 μL fractions. Fraction number two contained the bulk of the activity, 33 mCi. The pH of the $^{18}$F solution was then adjusted with 10 μL of glacial acetic acid. The $^{18}$F from fraction #2 was then mixed with 3 μL of 2 mM Al in 0.1 M pH 4 NaOAc buffer. The sample was then mixed with 10 μL of 0.05 M IMP 449 in 0.5 M NaOAc buffer at pH 4 and the reaction solution was heated at 94° C. for 15 min. The [Al$^{18}$F] IMP 449 was purified by RP-HPLC. The fraction containing the product was put through an HLB column to exchange the buffer. The column was washed with water after loading the sample. The product was eluted with 400 μL 1:1 EtOH:H$_2$O. RP-HPLC of the product showed one major peak with a shoulder (not shown). Since the yield was low, the specific activity was low and more peptide was injected into mice, resulting in a bsMAb:peptide ratio of 6.9:1 instead of 10:1.

Results

The labeling of IMP 449 with In-111 resulted in multiple products. Possibly some might be binuclear complexes. The $^{111}$In-IMP 449 showed high kidney uptake and high blood concentration. However, even as multiple species, $^{111}$In-IMP 449 showed localization to the tumor when pretargeted with TF2 (FIG. 1).

FIG. 1 shows the comparative biodistribution of $^{111}$In and $^{18}$F labeled IMP 449 in mice. Both labeled peptides showed similarly high levels of localization to tumor tissues in the presence of the bispecific TF2 antibody. The $^{111}$In-labeled species showed higher concentration in kidney than the $^{18}$F-labeled species in the presence or absence of TF2 antibody. The data are summarized in Tables 9-12 below.

TABLE 9

Mice were injected with TF2 (163.2 μg, 1.035 × 10$^{-9}$ mol) i.v. followed by $^{111}$In IMP 449 (1.035 × 10$^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 9.18 | 1.02 | 9.22 | 8.47 | 8.04 | 9.45 | 10.70 |
| Liver | 5 | 1.15 | 0.09 | 1.03 | 1.25 | 1.20 | 1.21 | 1.08 |
| Spleen | 5 | 0.48 | 0.06 | 0.43 | 0.49 | 0.58 | 0.50 | 0.42 |
| Kidney | 5 | 6.63 | 1.38 | 8.81 | 6.21 | 7.03 | 5.85 | 5.23 |
| Lung | 5 | 1.03 | 0.14 | 0.92 | 1.14 | 1.18 | 1.04 | 0.86 |
| Blood | 5 | 0.99 | 0.15 | 1.04 | 1.13 | 1.12 | 0.83 | 0.83 |
| Stomach | 5 | 0.16 | 0.05 | 0.25 | 0.17 | 0.16 | 0.13 | 0.12 |
| Small Int. | 5 | 2.33 | 0.65 | 2.21 | 2.51 | 2.01 | 3.33 | 1.59 |
| Large Int. | 5 | 0.20 | 0.04 | 0.21 | 0.25 | 0.18 | 0.21 | 0.14 |
| Femur | 5 | 1.45 | 0.87 | 0.59 | 1.30 | 0.71 | 2.02 | 2.62 |
| Spine | 5 | 1.18 | 1.23 | 0.89 | 3.35 | 0.76 | 0.47 | 0.43 |
| Brain | 5 | 0.14 | 0.16 | 0.05 | 0.06 | 0.13 | 0.04 | 0.43 |
| Muscle | 5 | 0.83 | 0.66 | 0.25 | 1.30 | 0.23 | 0.65 | 1.73 |
| Body Wt. | 5 | 25.49 | 1.41 | 27.89 | 24.14 | 25.27 | 25.10 | 25.06 |

TABLE 10

A group of 2 mice were injected with $^{111}$In IMP 449 (1.035 × 10$^{-10}$ mol) without pretargeting antibody. Peptide tissue uptake (% ID/g) at 1 h post peptide injection is shown below.

| Tissue | n | Mean | SD | Animal 1 | Animal 2 |
|---|---|---|---|---|---|
| Tumor | 2 | 0.922 | 0.195 | 0.784 | 1.060 |
| Liver | 2 | 1.033 | 0.048 | 0.999 | 1.067 |
| Spleen | 2 | 0.409 | 0.067 | 0.362 | 0.456 |
| Kidney | 2 | 6.046 | 0.449 | 5.729 | 6.364 |
| Lung | 2 | 0.695 | 0.032 | 0.672 | 0.717 |
| Blood | 2 | 0.805 | 0.182 | 0.934 | 0.676 |
| Stomach | 2 | 0.290 | 0.055 | 0.251 | 0.329 |
| Small Int. | 2 | 2.234 | 0.594 | 1.814 | 2.654 |
| Large Int. | 2 | 0.237 | 0.022 | 0.253 | 0.222 |
| Femur | 2 | 1.210 | 1.072 | 1.968 | 0.453 |
| Spine | 2 | 1.463 | 1.213 | 2.320 | 0.605 |
| Brain | 2 | 0.133 | 0.091 | 0.068 | 0.197 |
| Muscle | 2 | 1.005 | 1.148 | 1.817 | 0.193 |
| Body Wt. | 2 | 26.65 | 3.19 | 28.90 | 24.39 |

TABLE 11

Mice were injected with TF2 (163.2 µg, 1.035 × 10$^{-9}$ mol) i.v. followed by [Al$^{18}$F] IMP 449 (1.5 × 10$^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 7.624 | 3.080 | 5.298 | 7.848 | 12.719 | 5.118 | 7.136 |
| Liver | 5 | 0.172 | 0.033 | 0.208 | 0.143 | 0.196 | 0.131 | 0.180 |
| Spleen | 5 | 0.142 | 0.059 | 0.239 | 0.081 | 0.132 | 0.118 | 0.140 |
| Kidney | 5 | 2.191 | 0.125 | 2.313 | 2.141 | 2.154 | 2.319 | 2.027 |
| Lung | 5 | 0.315 | 0.094 | 0.474 | 0.230 | 0.300 | 0.305 | 0.265 |
| Blood | 5 | 0.269 | 0.143 | 0.431 | 0.395 | 0.132 | 0.126 | 0.260 |
| Stomach | 5 | 0.218 | 0.341 | 0.827 | 0.041 | 0.098 | 0.054 | 0.070 |
| Small Int. | 5 | 0.351 | 0.313 | 0.903 | 0.185 | 0.297 | 0.170 | 0.198 |
| Large Int. | 5 | 0.069 | 0.028 | 0.076 | 0.043 | 0.111 | 0.073 | 0.042 |
| Femur | 5 | 0.625 | 0.358 | 0.869 | 0.146 | 0.811 | 0.957 | 0.344 |
| Spine | 5 | 0.585 | 0.569 | 0.159 | 0.119 | 0.493 | 1.526 | 0.626 |
| Brain | 5 | 0.029 | 0.005 | 0.033 | 0.021 | 0.035 | 0.026 | 0.028 |
| Muscle | 5 | 0.736 | 0.970 | 0.190 | 0.064 | 0.494 | 2.438 | 0.496 |
| Body Wt. | 5 | 24.69 | 1.20 | 23.05 | 26.36 | 24.45 | 24.48 | 25.11 |

TABLE 12

Mice were injected with [Al$^{18}$F] IMP 449 (1.5 × 10$^{-10}$ mol) without pretargeting antibody. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 0.472 | 0.201 | 0.256 | 0.344 | 0.533 | 0.447 | 0.779 |
| Liver | 5 | 0.177 | 0.035 | 0.141 | 0.200 | 0.141 | 0.185 | 0.217 |
| Spleen | 5 | 0.118 | 0.027 | 0.098 | 0.094 | 0.101 | 0.144 | 0.151 |
| Kidney | 5 | 2.727 | 0.367 | 2.430 | 2.452 | 2.500 | 3.080 | 3.173 |
| Lung | 5 | 0.246 | 0.082 | 0.206 | 0.209 | 0.156 | 0.301 | 0.358 |
| Blood | 5 | 0.167 | 0.072 | 0.110 | 0.135 | 0.104 | 0.217 | 0.267 |
| Stomach | 5 | 0.114 | 0.083 | 0.149 | 0.241 | 0.037 | 0.067 | 0.074 |
| Small Int. | 5 | 0.277 | 0.081 | 0.407 | 0.286 | 0.206 | 0.213 | 0.271 |
| Large Int. | 5 | 0.072 | 0.029 | 0.061 | 0.052 | 0.047 | 0.083 | 0.118 |
| Femur | 5 | 0.100 | 0.032 | 0.080 | 0.144 | 0.110 | 0.109 | 0.059 |
| Spine | 5 | 0.305 | 0.268 | 0.104 | 0.647 | 0.099 | 0.132 | 0.545 |
| Brain | 5 | 0.034 | 0.025 | 0.018 | 0.018 | 0.022 | 0.034 | 0.077 |
| Muscle | 5 | 0.088 | 0.022 | 0.087 | 0.069 | 0.069 | 0.122 | 0.092 |
| Body Wt. | 5 | 25.34 | 1.72 | 25.05 | 26.88 | 26.40 | 25.88 | 22.51 |

This study shows that the simple, reproducible methods and compositions described herein produce $^{18}$F-labeled targeting peptides suitable for use in in vivo imaging of a variety of disease states. The skilled artisan will realize that the bispecific antibodies disclosed above are not limiting, but may comprise any known antibodies against a wide variety of disease or pathogen target antigens. Nor is the method limited to pretargeting with bispecific antibodies. In other embodiments, molecules or complexes that directly bind to target cells, tissues or organisms to be imaged may be labeled with $^{18}$F using the methods disclosed herein and administered to a subject for PET imaging (see Examples below).

The Al$^{18}$F-labeled peptides, exemplified by IMP 449, are sufficiently stable under in vivo conditions to be utilized in known imaging protocols, such as PET scanning. Further, the claimed methods result in preparation of $^{18}$F-labeled targeting peptides that are ready for injection within 1 hour of preparation time, well within the decay time of $^{18}$F to allow suitable imaging procedures to be performed. Finally, the described and claimed methods result in minimal exposure of the operator to radioisotope exposure, compared with known methods of preparing $^{18}$F-labeled compounds for imaging studies.

Example 12

$^{18}$F Labeling Kit

An $^{18}$F labeling kit was made by mixing 8.0 mg of IMP 449 with 0.1549 g of ascorbic acid. The two reagents were dissolved in 10.5 mL water and the solution was dispensed in 1.0 mL aliquots into 10 vials. The pH was not adjusted. The solutions were frozen, lyophilized and sealed under vacuum. The frozen lyophilized vials were rehydrated and used for studies with IMP 449 peptide.

Example 13

In Vivo Imaging Using $^{18}$F-Labeled Peptides and Comparison with $^{18}$F[FDG] Methods In vivo imaging techniques using pretargeting with bispecific antibodies and labeled targeting peptides were used to successfully detect tumors of relatively small size.

The $^{18}$F was purified on a WATERS® ACCELL™ Plus QMA Light cartridge according to the literature procedure, wherein the cartridge was washed with 10 mL 0.4 M KHCO$_3$ followed by a 10 mL wash with DI water. The $^{18}$F in 2 mL of water was pushed through the cartridge and then washed with 10 mL of water. The $^{18}$F was then eluted from the cartridge in 5×200 µL aliquots with 0.4 M $KHCO_3$. Most of the activity was eluted in the second fraction. The activity in the second fraction was mixed with 3 µL 2 mM $Al^{3+}$ in a pH 4 acetate buffer. The $Al^{18}F$ solution was then injected into the ascorbic acid IMP 449 labeling vial and heated to 105° C. for 15 min. The reaction solution was cooled and mixed with 0.8 mL DI water. The reaction contents were placed on a WATERS® OASIS® 1 cc HLB Column and eluted into a waste vial. The column was washed with 3×1 mL DI water. The column was transferred to a formulation vial containing ascorbic acid. The column was washed with 2×200 µL 1:1 $EtOH/H_2O$ to elute the labeled peptide.

The recombinant, humanized, tri-Fab bsMAb, TF2, was prepared as described above. TF2 binds divalently to carcinoembryonic antigen (CEA) and monovalently to the synthetic hapten, HSG (histamine-succinyl-glycine). The bsMAb was >95% immunoreactive against CEA and the divalent-HSG NOTA-peptide IMP 449 using a size-exclusion HPLC method (not shown).

Biodistribution and MicroPET Imaging.

Six-week-old NCr nu-m female nude mice were implanted s.c. with the human colonic cancer cell line, LS174T (ATCC, Manassas, Va.). When tumors were visibly established, pretargeted animals were injected intravenously with 162 µg (~1 nmole/0.1 mL) TF2 or TF10 (control non-targeting tri-Fab bsMAb), and then 16-18 h later, ~0.1 nmole of $[Al^{18}F]$ IMP 449 (84 µCi, 3.11 MBq/0.1 mL) was injected intravenously. The concentration of the $[Al^{18}F]$ IMP 449 was determined by assuming 100% recovery of added aluminum. Other non-pretargeted control animals received $^{18}F$ alone (150 µCi, 5.5 MBq), $Al^{18}F$ complex alone (150 µCi, 5.55 MBq), the $[Al^{18}F]$ IMP 449 peptide alone (84 µCi, 3.11 MBq), or $[^{18}F]FDG$ (150 µCi, 5.55 MBq). $^{18}F$ and $[^{18}F]FDG$ were obtained on the day of use from IBA Molecular (Somerset, N.J.). Animals receiving $[^{18}F]FDG$ were fasted overnight, but water was given ad libitum.

At 1.5 h after the radiotracer injection, animals were anesthetized, bled intracardially, and necropsied. Tissues were weighed and counted together with a standard dilution prepared from each of the respective products. Due to the short physical half-life of $^{18}F$, standards were interjected between each group of tissues from each animal. Uptake in the tissues is expressed as the counts per gram divided by the total injected activity to derive the percent-injected dose per gram (% ID/g).

Two types of imaging studies were performed. In one set, 3 nude mice bearing small LS174T subcutaneous tumors received either the pretargeted $[Al^{18}F]$ IMP 449, $[Al^{18}F]$ IMP 449 alone (not pretargeted), both at 135 µCi (5 MBq; 0.1 nmol), or $[^{18}F]FDG$ (135 µCi, 5 MBq). At 2 h after the intravenous radiotracer injection, the animals were anesthetized with a mixture of $O_2/N_2O$ and isoflurane (2%) and kept warm during the scan. Mice were placed in a supine position on the scan bed of an INVEON® animal PET scanner (Siemens Preclinical Solutions, Knoxville, Tenn.). This scanner has an intrinsic spatial resolution of 1.5 mm. Emission scans were acquired over 15 min $[^{18}F]FDG$ or 30 min $([Al^{18}F]$ IMP 449). Scans were reconstructed using INVEON® Acquisition Workplace software (IAW, version 1.2) using an ordered set expectation maximization3D/maximum aposteriori (OSEM3D/MAP) algorithm with the following parameters: matrix 256×256×159, pixel size 0.43×0.43×0.8 mm3 and MAP prior of 0.5 mm.

Representative coronal cross-sections (0.8 mm thick) in a plane located approximately in the center of the tumor were displayed, with intensities adjusted until pixel saturation occurred in any region of the body (excluding the bladder) and without background adjustment.

In a separate dynamic imaging study, a single LS174T-bearing nude mouse that was given the TF2 bsMAb 16 h earlier was anesthetized with a mixture of $O_2/N_2O$ and isoflurane (2%), placed supine on the camera bed, and then injected intravenously with 219 µCi (8.1 MBq) $[Al^{18}F]$ IMP 449 (0.16 nmol). Data acquisition was immediately initiated over a period of 120 minutes. Data were histogrammed in 24 frames of 5 min each. The scans were reconstructed using OSEM3D/MAP with the same parameters as described above. Each of the 24-image time frames was examined. For presentation, time-frames ending at 5, 15, 30, 60, 90, and 120 min (ie, the 5-min image is for the period from time-zero to 5 min) were displayed for each cross-section (coronal, sagittal, and transverse). For sections containing tumor, at each interval the image intensity was adjusted until pixel saturation first occurred in the tumor. Image intensity was increased as required over time to maintain pixel saturation within the tumor. Coronal and sagittal cross-sections without tumor taken at the same interval were adjusted to the same intensity as the transverse section containing the tumor. Background activity was not adjusted.

Results

While $^{18}F$ alone and $[Al^{18}F]$ complexes had similar uptake in all tissues, considerable differences were found when the complex was chelated to IMP 449 (Table 13). The most striking differences were found in the uptake in the bone, where the non-chelated $^{18}F$ was 60- to nearly 100-fold higher in the scapula and ~200-fold higher in the spine. This distribution is expected since $^{18}F$, or even a metal-fluoride complex, is known to accrete in bone (Franke et al. 1972, Radiobiol. Radiother. (Berlin) 13:533). Higher uptake was also observed in the tumor and intestines as well as in muscle and blood. The chelated $[Al^{18}F]$ IMP 449 had significantly lower uptake in all the tissues except the kidneys, illustrating the ability of the chelate-complex to be removed efficiently from the body by urinary excretion. Pretargeting the $[Al^{18}F]$ IMP 449 using the TF2 anti-CEA bsMAb shifted uptake to the tumor, increasing it from 0.20±0.05 to 6.01±1.72% injected dose per gram at 1.5 h, while uptake in the normal tissues was similar to the $[Al^{18}F]$ IMP 449 alone. Tumor/nontumor ratios were 146±63, 59±24, 38±15, and 2.0±1.0 for the blood, liver, lung, and kidneys, respectively, with other tumor/tissue ratios >100:1 at this time. Although both $^{18}F$ alone and $[Al^{18}F]$ alone had higher uptake in the tumor than the chelated $[Al^{18}F]$ IMP 449, yielding tumor/blood ratios of 6.7±2.7 and 11.0±4.6 vs. 5.1±1.5, respectively, tumor uptake and tumor/blood ratios were significantly increased with pretargeting (all P values <0.001).

Biodistribution was also compared to the most commonly used tumor imaging agent, $[^{18}F]FDG$, which targets tissues with high glucose consumption and metabolic activity. Its uptake was appreciably higher than the $[Al^{18}F]$ IMP 449 in all normal tissues, except the kidney. Tumor uptake was similar for both the pretargeted $[Al^{18}F]$ IMP 449 and $[^{18}F]FDG$, but because of the higher accretion of $[^{18}F]FDG$ in most normal tissues, tumor/nontumor ratios with $[^{18}F]FDG$ were significantly lower than those in the pretargeted animals (all P values <0.001).

TABLE 13

Biodistribution of TF2-pretargeted [Al$^{18}$F] IMP 449 and other control $^{18}$F-labeled agents in nude mice bearing LS174T human colonic xenografts. For pretargeting, animals were given TF2 16 h before the injection of the [Al$^{18}$F] IMP 449. All injections were administered intravenously.

| | Percent Injected Dose Per Gram (Mean ± SD) at 1.5 hr Post-Injection | | | | |
|---|---|---|---|---|---|
| | $^{18}$F alone | [Al$^{18}$F] alone | [Al$^{18}$F] IMP 449 alone | TF2-pretargeted [Al$^{18}$F] IMP 449 | [$^{18}$F]FDG |
| Tumor | 1.02 ± 0.45 | 1.38 ± 0.39 | 0.20 ± 0.05 | 6.01 ± 1.72 | 7.25 ± 2.54 |
| Liver | 0.11 ± 0.02 | 0.12 ± 0.02 | 0.08 ± 0.03 | 0.11 ± 0.03 | 1.34 ± 0.36 |
| Spleen | 0.13 ± 0.06 | 0.10 ± 0.03 | 0.08 ± 0.02 | 0.08 ± 0.02 | 2.62 ± 0.73 |
| Kidney | 0.29 ± 0.07 | 0.25 ± 0.07 | 3.51 ± 0.56 | 3.44 ± 0.99 | 1.50 ± 0.61 |
| Lung | 0.26 ± 0.08 | 0.38 ± 0.19 | 0.11 ± 0.03 | 0.17 ± 0.04 | 3.72 ± 1.48 |
| Blood | 0.15 ± 0.03 | 0.13 ± 0.03 | 0.04 ± 0.01 | 0.04 ± 0.02 | 0.66 ± 0.19 |
| Stomach | 0.21 ± 0.13 | 0.15 ± 0.05 | 0.20 ± 0.32 | 0.12 ± 0.18 | 2.11 ± 1.04 |
| Small Int. | 1.53 ± 0.33 | 1.39 ± 0.34 | 0.36 ± 0.23 | 0.27 ± 0.10 | 1.77 ± 0.61 |
| Large Int. | 1.21 ± 0.13 | 1.78 ± 0.70 | 0.05 ± 0.04 | 0.03 ± 0.01 | 2.90 ± 0.79 |
| Scapula | 6.13 ± 1.33 | 9.83 ± 2.31 | 0.08 ± 0.06 | 0.04 ± 0.02 | 10.63 ± 5.88 |
| Spine | 19.88 ± 2.12 | 19.03 ± 2.70 | 0.13 ± 0.14 | 0.08 ± 0.03 | 4.21 ± 1.79 |
| Muscle | 0.16 ± 0.05 | 0.58 ± 0.36 | 0.06 ± 0.05 | 0.10 ± 0.20 | 4.35 ± 3.01 |
| Brain | 0.15 ± 0.06 | 0.13 ± 0.03 | 0.01 ± 0.01 | 0.01 ± 0.00 | 10.71 ± 4.53 |
| Tumor wt (g) | 0.29 ± 0.07 | 0.27 ± 0.10 | 0.27 ± 0.08 | 0.33 ± 0.11 | 0.25 ± 0.21 |
| N | 6 | 7 | 8 | 7 | 5 |

Figure 2:
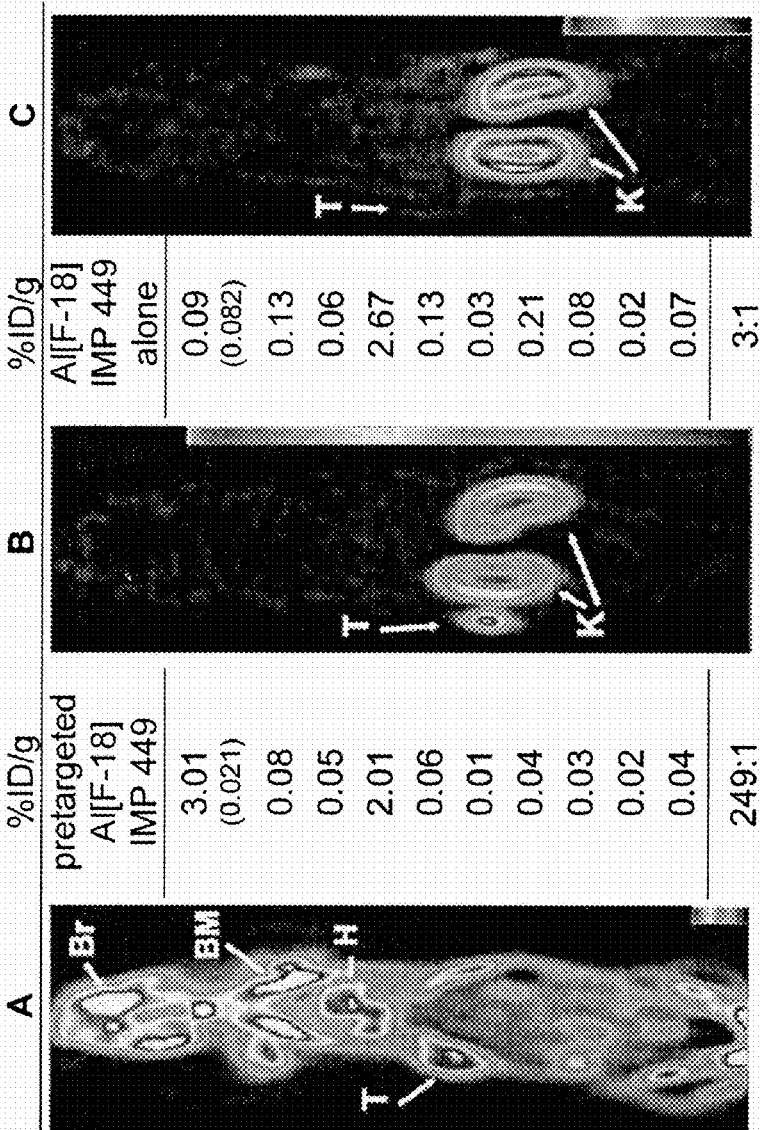
FIG. 2. Biodistribution of $^{18}$F-labeled agents in tumor-bearing nude mice by microPET imaging. Coronal slices of 3 nude mice bearing a small, subcutaneous LS174T tumor on each left flank after being injected with either (A) [$^{18}$F]FDG, (B) Al[$^{18}$F] IMP 449 pretargeted with the anti-CEA x anti-HSG bsMAb, (C) Al[$^{18}$F] IMP 449 alone (not pretargeted with the bsMAb). Biodistribution data expressed as percent-injected dose per gram (% ID/g) are given for the tissues removed from the animals at the conclusion of the imaging session. Abbreviations: B, bone marrow; H, heart; K, kidney; T, tumor.
Figure 3:
FIG. 3. Dynamic imaging study of pretargeted Al[$^{18}$F] IMP 449 given to a nude mouse bearing a 35-mg LS174T human colorectal cancer xenograft in the upper flank. The top 3 panels show coronal, sagittal, and transverse sections, respectively, taken of a region of the body centering on the tumor's peripheral location at 6 different 5-min intervals over the 120-min imaging session. The first image on the left in each sectional view shows the positioning of the tumor at the intersection of the crosshairs, which is highlighted by arrows. The animal was partially tilted to its right side during the imaging session. The bottom 2 panels show additional coronal and sagittal sections that focus on a more anterior plane in the coronal section to highlight distribution in the liver and intestines, while the sagittal view crosses more centrally in the body. Abbreviations: Cor, coronal; FA, forearms; H, heart; K, kidney; Lv, liver; Sag, sagittal; Tr, transverse; UB, urinary bladder.

Several animals were imaged to further analyze the biodistribution of [Al$^{18}$F] IMP 449 alone or [Al$^{18}$F] IMP 449 pretargeted with TF2, as well [$^{18}$F]FDG. Static images initiated at 2.0 h after the radioactivity was injected corroborated the previous tissue distribution data showing uptake almost exclusively in the kidneys (FIG. 2). A 21-mg tumor was easily visualized in the pretargeted animal, while the animal given the [Al$^{18}$F] IMP 449 alone failed to localize the tumor, having only renal uptake. No evidence of bone accretion was observed, suggesting that the Al$^{18}$F was bound firmly to IMP 449. This was confirmed in another pretargeted animal that underwent a dynamic imaging study that monitored the distribution of the [Al$^{18}$F] IMP 449 in 5-min intervals over 120 minutes (FIG. 3). Coronal and sagittal slices showed primarily cardiac, renal, and some hepatic uptake over the first 5 min, but heart and liver activity decreased substantially over the next 10 min, while the kidneys remained prominent throughout the study. There was no evidence of activity in the intestines or bone over the full 120-min scan. Uptake in a 35-mg LS174T tumor was first observed at 15 min, and by 30 min, the signal was very clearly delineated from background, with intense tumor activity being prominent during the entire 120-min scanning.

In comparison, static images from an animal given [$^{18}$F]FDG showed the expected pattern of radioactivity in the bone, heart muscle, and brain observed previously (McBride et al., 2006, J. Nucl. Med. 47:1678; Sharkey et al., 2008, Radiology 246:497), with considerably more background activity in the body (FIG. 2). Tissue uptake measured in the 3 animals necropsied at the conclusion of the static imaging study confirmed much higher tissue $^{18}$F radioactivity in all tissues. While tumor uptake with [$^{18}$F]FDG was higher in this animal than in the pretargeted one, tumor/blood ratios were more favorable for pretargeting; and with much less residual activity in the body, tumor visualization was enhanced by pretargeting.

These studies demonstrate that a biomolecule, in this case a hapten-peptide used in pretargeted imaging, can be rapidly labeled (60 min total preparation time) with $^{18}$F by simply forming an aluminum-fluoride complex that can then be bound by a suitable chelate and incorporated into the hapten-peptide. This can be made more general by simply coupling the [Al$^{18}$F]-chelate to any molecule that can be attached to the chelating moiety and be subsequently purified. In preferred embodiments, the percentage incorporation of label and specific activity of the labeled compound are sufficient that purification of the labeled molecule is not necessary. We were also able to bind $^{18}$F to Al that was already bound to the chelator (data not shown).

This is the first report describing a direct, facile, and rapid method of binding $^{18}$F to various compounds via an aluminum conjugate. The stability of such products, such as [Al$^{18}$F], depends on the properties of the chelate used to link $^{18}$F to the molecule of interest. A chelate may be selected with the right configuration to optimize metal incorporation and subsequent stability. The [Al$^{18}$F] peptide was stable in vitro and in vivo when bound by a NOTA-based chelate. Yields were within the range found with conventional $^{18}$F labeling procedures. These results further demonstrate the feasibility of PET imaging using metal$^{18}$F chelated to a wide variety of targeting molecules.

Example 14

Preparation and Labeling of IMP 460 with Al—$^{18}$F

IMP 460 NODA-Ga-D-Ala-D-Lys(HSG)-D-Tyr-D-Lys(HSG)-NH$_2$ was synthesized in a similar manner as described above for IMP 361. The NODA-Ga ligand was purchased from CHEMATECH® and attached on the peptide synthesizer like the other amino acids. The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and NODA-GA(tBu)$_3$. The peptide was then cleaved and purified by HPLC to afford the product. HRMS C61H92N18O18MH$^+$ Calc 1365.6909 Found 1365.6912.

Radiolabeling of IMP 460

IMP 460 (0.0020 g) was dissolved in 732 µL, pH 4, 0.1 M NaOAc. The $^{18}$F was purified as described above, neutralized with glacial acetic acid and mixed with the Al solution. The peptide solution, 20 µL was then added and the solution was heated at 99° C. for 25 min. The crude product was then purified on a WATERS® HLB column. The [Al$^{18}$F] labeled peptide was in the 1:1 EtOH/H$_2$O column eluent. The reverse phase HPLC trace in 0.1% TFA buffers showed a clean single HPLC peak at the expected location for the labeled peptide (not shown).

Example 15

Synthesis and Labeling of IMP 461 and IMP 462 NOTA-Conjugated Peptides

The simplest possible NOTA ligand (protected for peptide synthesis) was prepared and incorporated into two peptides for pretargeting—IMP 461 and IMP 462.

Figure 6:
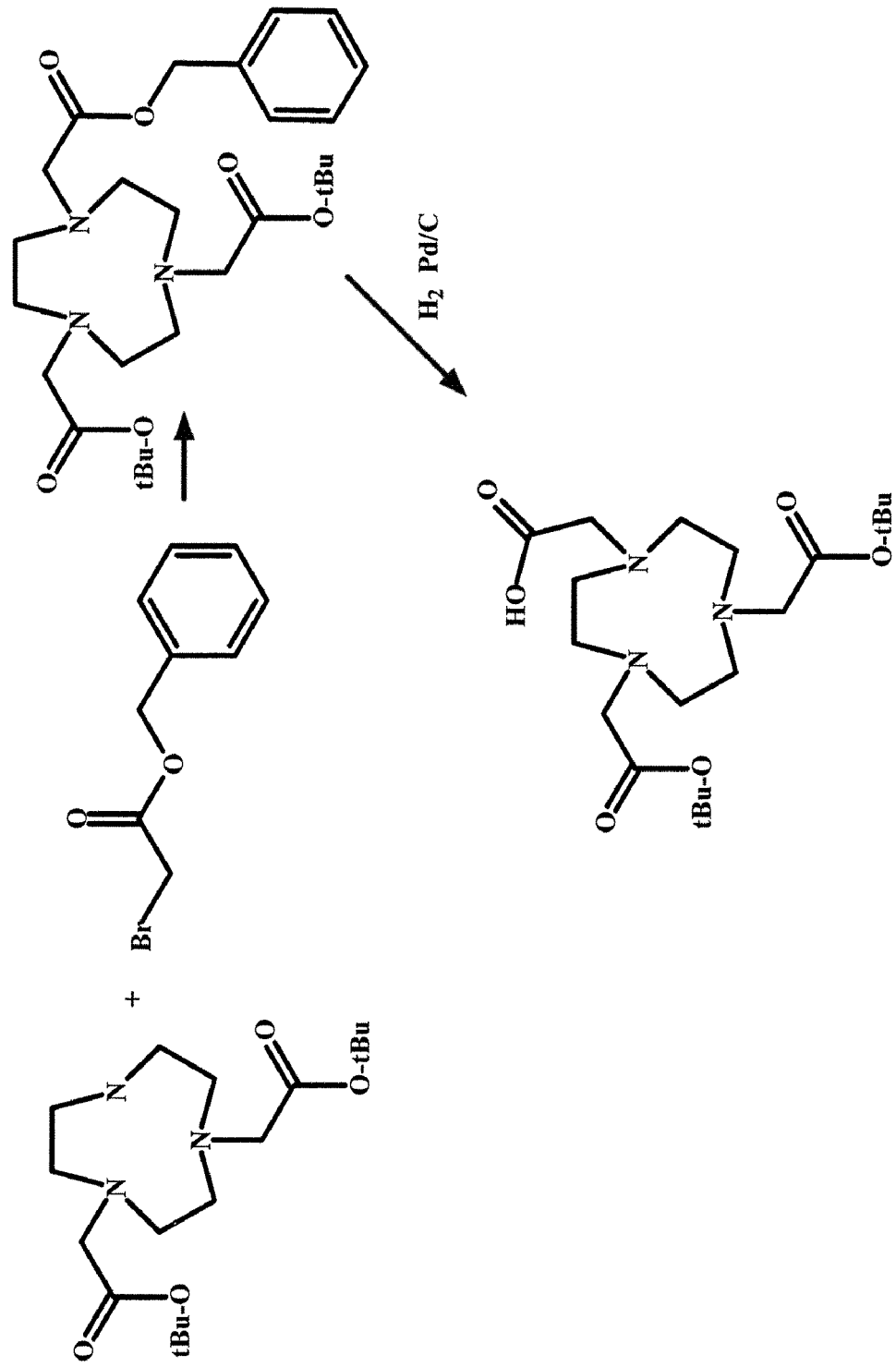
FIG. 6. Synthesis of di-tert-butyl NOTA.

Synthesis of Di-t-butyl-NOTA (FIG. 6)

NO2AtBu (0.501 g 1.4×10$^{-3}$ mol) was dissolved in 5 mL anhydrous acetonitrile. Benzyl-2-bromoacetate (0.222 mL, 1.4×10$^{-3}$ mol) was added to the solution followed by 0.387 g of anhydrous K$_2$CO$_3$. The reaction was allowed to stir at room temperature overnight. The reaction mixture was filtered and concentrated to obtain 0.605 g (86% yield) of the benzyl ester conjugate. The crude product was then dissolved in 50 mL of isopropanol, mixed with 0.2 g of 10% Pd/C (under Ar) and placed under 50 psi H$_2$ for 3 days. The product was then filtered and concentrated under vacuum to obtain 0.462 g of the desired product ESMS MH$^-$ 415.

Synthesis of IMP 461

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and Bis-t-butylNOTA-OH. The peptide was then cleaved and purified by HPLC to afford the product IMP 461 ESMS MH$^+$ 1294 (NOTA-D-Ala-D-Lys(HSG)-D-Tyr-D-Lys(HSG)-NH$_2$).

Synthesis of IMP 462

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Asp(But)-OH, and Bis-t-butyl-NOTA-OH. The peptide was then cleaved and purified by HPLC to afford the product IMP 462 ESMS MH$^+$ 1338 (NOTA-D-Asp-D-Lys(HSG)-D-Tyr-D-Lys(HSG)-NH$_2$). NOTA esters were added to the peptides on the peptide synthesizer.

$^{18}$F Labeling of the Peptides (IMP 461 & IMP 462)

The peptides were dissolved in pH 4.13, 0.5 M NaOAc to make a 0.05 M peptide solution, which was stored in the freezer until needed. The F-18 was received in 2 mL of water and trapped on a SEP-PAK® Light, WATERS® ACCELL™ Plus QMA Cartridge, which had been previously washed with 5 mL of 0.4 M KHCO$_3$ followed by a 5 mL water wash. The column was washed with 5 mL of DI water to removed undesired contaminants from the $^{18}$F. The $^{18}$F was then eluted from the column with 200 µL aliquots of 0.4 M KHCO$_3$ with most of the activity in the second aliquot. The bicarbonate in the aliquots was neutralized to ~pH 4 by the addition of 10 µL of glacial acetic acid to the vials before the addition of the activity. A 100 µL aliquot of the purified $^{18}$F solution was removed and mixed with 3 µL, 2 mM Al in pH 4, 0.1 M NaOAc. The peptide, 10 µL (0.05 M) was added and the solution was heated at ~100° C. for 15 min. The crude reaction mixture was diluted with 700 µL DI water and placed on an HLB column and the liquid was then drawn through the column into a waste vial. The reaction vial was rinsed with an additional 1 mL of DI water and pulled (under vacuum) through the HLB column. The HLB column was washed with additional 2×1 mL portions of DI water. The column was moved to an empty vial and eluted with 2×100 µL of 1:1 EtOH/H$_2$O to obtain the purified $^{18}$F-labeled peptide.

Example 16

Preparation and $^{18}$F Labeling of IMP 467

Synthesis

IMP 467 C-NETA-succinyl-D-Lys(HSG)-D-Tyr-D-Lys(HSG)-NH$_2$, MW 1528.7

Figure 4:
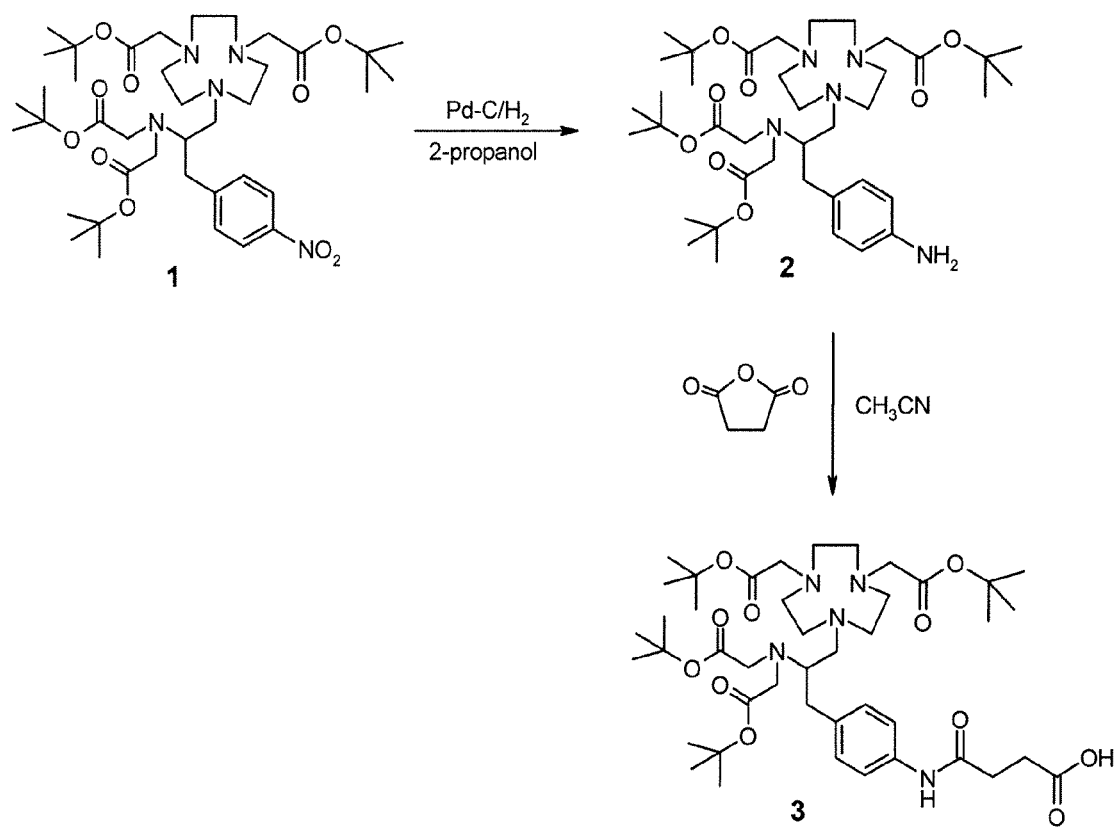
FIG. 4. Synthesis of tetra tert-butyl C-NETA-succinyl.
Figure 5:
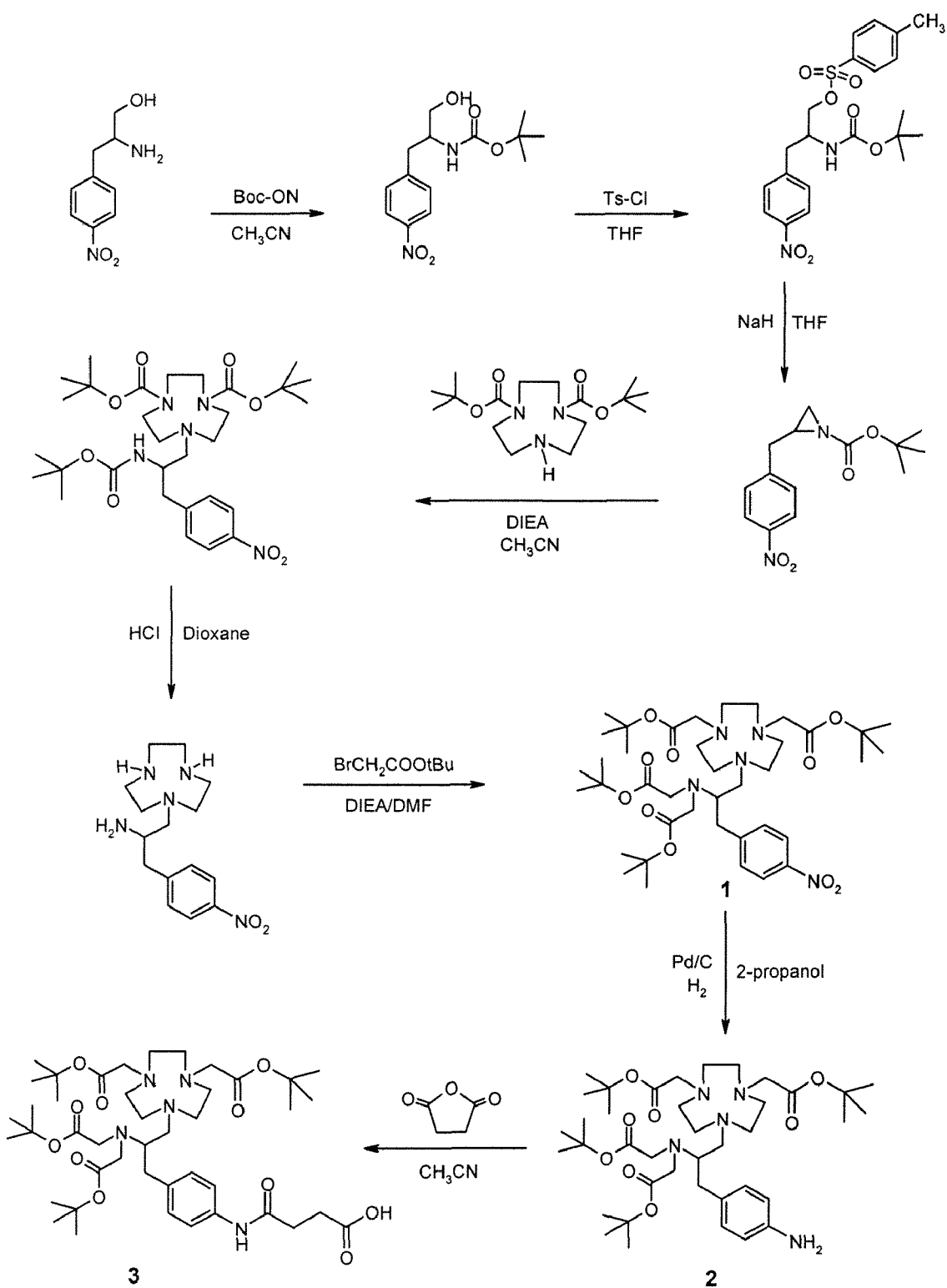
FIG. 5. Detailed synthesis of tetra tert-butyl C-NETA-succinyl.

Tetra tert-butyl C-NETA-succinyl was produced according to FIG. 4. The tert-Butyl {4-[2-(Bis-(tert-butyoxycarbonyl)methyl-3-(4-nitrophenyl)propyl]-7-tert-butyoxycarbonyl[1,4,7]triazanonan-1-yl} was prepared as described in Chong et al. (J. Med. Chem. 2008, 51:118-125). A more extensive synthetic scheme is shown in FIG. 5. The ligand 3 was purified by high performance liquid chromatography (HPLC) using a WATERS® PrepLC 4000 system equipped with a SUNFIRE® Prep C$_{18}$ reverse-phase column (30×150 mm, 5 µm). Chromatographic separations were achieved using a linear gradient of 100% A (0.1% TFA) to 100% B (90% acetonitrile, 10% water, 0.1% TFA) over 50 min at a flow rate of 45 mL/min, absorbance was detected at 220 nm.

The peptide, IMP 467 C-NETA-succinyl-D-Lys(HSG)-D-Tyr-D-Lys(HSG)-NH$_2$ MH$^+$ 1527.87 was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys(Fmoc)-OH, Trt-HSG-OH, the Aloc was cleaved, tert-Butyl{4-[Bis-(tert-butoxycarbonylmethyl)amino)-3-(4-succinylamidophenyl)propyl]-7-tert-butoxycarbonylmethyl[1,4,7]triazanonan-1-yl}acetate 3. The peptide was then cleaved from the resin and purified by RP-HPLC to yield 6.3 mg of IMP 467. About 30.6 mg of a product with molecular mass 1034.84 and retention time 8.470 min was also obtained (TFA amide).

The crude peptide was purified by high performance liquid chromatography (HPLC) using a C18 column. Chromatographic separations were achieved using a linear gradient of 100% A (0.1% TFA) to 80% A: 20% B (90% acetonitrile, 10% water, 0.1% TFA) over 80 min at a flow rate of 45 mL/min, absorbance was detected at 220 nm.

Radiolabeling

A 2 mM solution of IMP 467 was prepared in pH 4, 0.1 M NaOAc. The $^{18}$F, 139 mCi, was received in 2 mL in a syringe. The activity was eluted through a WATERS® ACCELL™ Plus SEP-PAK® Light QMA cartridge and washed with 5 mL water to remove any metal ion contaminants. The $^{18}$F was then eluted with 1 mL of 0.4 M KHCO$_3$ in the following fractions:

TABLE 14

$^{18}$F elution fractions from SEP-PAK ® QMA

| Fraction | Volume µL | Activity mCi |
| --- | --- | --- |
| 1 | 200 | 19.7 |
| 2 | 50 | 38.0 |
| 3 | 50 | 31.5 |
| 4 | 50 | 15.1 |
| 5 | 50 | 6.81 |
| 6 | 200 | 8.67 |
| 7 | 400 | 2.69 |

The labeled IMP 467 was purified by HLB RP-HPLC analysis, according to Paragraph 0325. The RP-HPLC showed two peaks eluting (not shown), which are believed to be diastereomers of Al$^{18}$F IMP 467. Supporting this hypothesis, there appeared to be some interconversion between the two HLB peaks when IMP 467 was incubated at 37° C. (not shown). In pretargeting techniques as discussed below, since the Al$^{18}$F-chelator complex is not part of the hapten site for antibody binding, the presence of diastereomers does not appear to affect targeting of the $^{18}$F-labeled peptide to diseased tissues.

Comparison of Yield of Radiolabeled Peptides

In an attempt to improve labeling yields while maintaining in vivo stability, 3 new NOTA derivatives of pretargeting peptide were synthesized (IMP 460, IMP 461 and IMP 467). Of these, IMP 467 nearly doubled the labeling yields of the other peptides (Table 15). All of the labeling studies in Table 15 were performed with the same number of moles of peptide and aluminum. The results shown in Table 15 represent an exemplary labeling experiment with each peptide.

To generate the data of Table 15, three microliters of 2 mM Al$^{3+}$ stock solution was added to 60 µL of $^{18}$F (44 MBq) followed by the addition of 10 µL of 0.05 M peptide solution in pH 4.1, 0.5 M NaOAc. The four reaction mixtures were formulated and placed in a 103° C. heating block for 19 min. The reaction mixtures were purified by HLB column as described in Paragraph 0325 to determine the radiochemical reaction yield.

The $^{18}$F-labeling yield of IMP 467 was ~70% when only 40 nmol (~13-fold less than IMP 449) was used with 1.3 GBq (35 mCi) of $^{18}$F, indicating this ligand has improved binding properties for the Al$^{18}$F complex. By enhancing the kinetics of ligand binding, yields were substantially improved (average 65-75% yield), while using fewer moles of IMP 467 (40 nmol), relative to IMP 449 (520 nmol, 44% yield).

TABLE 15

Comparison of yields of different NOTA containing peptides

| Peptide | Yield |
|---|---|
| IMP 449 | 44% |
| IMP 460 | 5.8% |
| IMP 461 | 31% |
| IMP 467 | 87% |

Example 17

Pretargeted Biodistribution With $^{18}$F-Labeled IMP 467 in LS174T Tumor Bearing Nude Mice The $^{18}$F-labeled IMP 467 peptide, prepared in the same manner as described in Paragraph 0328, was diluted for injection into LS174T tumor bearing nude mice. Al$^{18}$F-IMP 467 was prepared and injected in nude mice that were necropsied 1.5 h later. Tables 16 and 17 compare the biodistribution of $^{18}$F-labeled IMP 467 using a TF2 pretargeting protocol (Table 16), compared to peptide alone (Table 17). As shown in Table 17, the peptide cleared quickly from the blood and body, similar to IMP 449. The low uptake in the bone compared to $^{18}$F or Al$^{18}$F illustrates the stability of the Al$^{18}$F chelate and its suitability for pretargeting. As with IMP 449, using the TF2 bispecific antibody and pretargeting the distribution of labeled IMP 467 was mainly limited to tumor and kidney, with very little distribution to bone or other normal tissues. Imaging studies with $^{18}$F-labeled IMP 467 are reported below. The data indicate that AlF-18 IMP 467 was stable in-vivo and the peptide targeted the antibody on the tumor surface.

TABLE 16

TF2 Pretargeted Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.741 | 0.522 | 3.415 | 1.265 | 2.742 | 2.112 | 1.0 | 0.0 |
| Liver | 6 | 1.510 | 0.475 | 0.175 | 0.086 | 0.247 | 0.087 | 22.6 | 12.9 |
| Spleen | 6 | 0.131 | 0.075 | 0.326 | 0.261 | 0.036 | 0.020 | 16.3 | 13.3 |
| Kidney | 6 | 0.160 | 0.027 | 3.098 | 0.647 | 0.484 | 0.076 | 1.1 | 0.3 |
| Lung | 6 | 0.178 | 0.032 | 0.204 | 0.059 | 0.035 | 0.011 | 17.0 | 5.0 |
| Blood | 6 | 0.207 | 0.006 | 0.153 | 0.100 | 0.252 | 0.145 | 28.2 | 13.8 |
| Stomach | 6 | 0.443 | 0.089 | 0.186 | 0.148 | 0.079 | 0.053 | 23.3 | 9.4 |
| Small Int. | 6 | 1.086 | 0.121 | 0.338 | 0.125 | 0.359 | 0.117 | 10.5 | 2.9 |
| Large Int. | 6 | 0.804 | 0.116 | 0.115 | 0.047 | 0.093 | 0.045 | 34.5 | 21.1 |
| Scapula | 6 | 0.154 | 0.040 | 0.123 | 0.020 | 0.019 | 0.005 | 28.0 | 10.9 |
| Spine | 6 | 0.199 | 0.022 | 0.503 | 0.372 | 0.101 | 0.082 | 9.4 | 6.5 |
| Muscle | 6 | 0.088 | 0.021 | 0.200 | 0.237 | 0.014 | 0.014 | 56.3 | 64.3 |
| Brain | 6 | 0.329 | 0.049 | 0.013 | 0.002 | 0.004 | 0.000 | 260.4 | 104.0 |

TABLE 17

Peptide Alone Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Tumor | 4 | 1.235 | 0.612 | 0.287 | 0.055 | 0.330 | 0.138 | 1.00 | 0.00 |
| Liver | 4 | 1.199 | 0.172 | 0.086 | 0.018 | 0.101 | 0.009 | 3.35 | 0.37 |
| Spleen | 4 | 0.105 | 0.026 | 0.075 | 0.017 | 0.008 | 0.001 | 3.87 | 0.17 |
| Kidney | 4 | 0.140 | 0.019 | 2.034 | 0.517 | 0.290 | 0.095 | 0.16 | 0.08 |
| Lung | 4 | 0.126 | 0.023 | 0.129 | 0.034 | 0.016 | 0.001 | 2.24 | 0.17 |

TABLE 17-continued

Peptide Alone Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Blood | 4 | 0.212 | 0.004 | 0.043 | 0.007 | 0.067 | 0.014 | 6.91 | 1.89 |
| Stomach | 4 | 0.590 | 0.125 | 0.023 | 0.009 | 0.013 | 0.003 | 13.43 | 3.26 |
| Small Int. | 4 | 1.021 | 0.122 | 0.235 | 0.082 | 0.246 | 0.117 | 1.34 | 0.50 |
| Large Int. | 4 | 0.564 | 0.056 | 0.073 | 0.023 | 0.041 | 0.015 | 4.04 | 0.53 |
| Scapula | 4 | 0.120 | 0.025 | 0.144 | 0.025 | 0.017 | 0.004 | 2.04 | 0.51 |
| Spine | 4 | 0.151 | 0.020 | 0.284 | 0.058 | 0.042 | 0.006 | 1.03 | 0.18 |
| Muscle | 4 | 0.098 | 0.019 | 0.064 | 0.022 | 0.006 | 0.003 | 4.80 | 1.49 |
| Brain | 4 | 0.287 | 0.029 | 0.013 | 0.003 | 0.004 | 0.001 | 22.19 | 5.06 |

Example 18

Factors Affecting Yield and Stability of IMP 467 Labeling

Peptide Concentration

To examine the effect of varying peptide concentration on yield, the amount of binding of $Al^{18}F$ to peptide was determined in a constant volume (63 µL) with a constant amount of $Al^{3+}$ (6 nmol) and $^{18}F$, but varying the amount of peptide added. Three microliters of 2 mM $Al^{3+}$ stock solution was added to 40 µL of $^{18}F$ (24 MBq) followed by the addition of 5, 10, 15 or 20 µL of 2 mM IMP 467 in 0.1 mM, pH 4.1 acetate buffer and 15, 10, 5 or 0 µL of water respectively. The reaction solutions were heated to 99° C. for 15 min, then purified by HLB column as described above to determine the isolated radiochemical yield. The yield of labeled peptide IMP 467 decreased with a decreasing concentration of peptide as follows: 40 nmol peptide (82% yield); 30 nmol (79% yield); 20 nmol (75% yield); 10 nmol (49% yield). Thus, varying the amount of peptide between 20 and 40 nmol had little effect on yield with IMP 467. However, a decreased yield was observed starting at 10 nmol of peptide in the labeling mix.

Aluminum Concentration

When IMP 467 was labeled in the presence of increasing amounts of $Al^{3+}$ 0, 5, 10, 15, 20 µL of 2 mM Al in pH 4 acetate buffer and keeping the total volume constant), yields of 3.5%, 80%, 77%, 78% and 74%, respectively, were achieved. These results indicated that (a) non-specific binding of $^{18}F$ to this peptide in the absence of $Al^{3+}$ is minimal, (b) 10 nmol of $Al^{3+}$ as sufficient to allow for maximum $^{18}F$-binding, and (c) higher amounts of $Al^{3+}$ did not reduce binding substantially, indicating that there was sufficient chelation capacity at this peptide concentration.

Kinetics of $Al^{18}F$ IMP 467 Radiolabeling

Three microliters of 2 mM $Al^{3+}$ tock solution were mixed with 40 µL of $^{18}F$ followed by the addition of 20 µL of 2 mM IMP 467 in 0.1 mM, pH 4 acetate buffer. Four reaction mixtures were formulated and placed in a 107° C. heating block for 5, 10, 15 and 30 min. The crude products were each purified on a Waters Oasis® HLB 1 cc (30 mg) Flangeless Cartridge. Briefly, 200 µL of water was added to the reaction solution, which was then removed via pipette and applied to the HLB column. The reaction solution was pulled into the column. The reaction vessel was rinsed with 1 mL of water, which was then transferred and pulled into the column. The column was eluted with 2×200 µL portions of 1:1 EtOH/H$_2$O, with the product being isolated in a 3-mL vial that contained 15 mg of ascorbic acid that was adjusted to pH 6 and previously lyophilized. The yield was determined by measuring the activity left in the reaction vessel, remaining on the HLB column, in the water wash, and in the 1:1 EtOH/H$_2$O. The amount of activity in the 1:1 EtOH/H$_2$O fraction divided by the total activity from the other fractions gave the isolated radiochemical yield. The radiolabeled peptides were then analyzed by RP-HPLC, which showed that the unbound $^{18}F$ was removed in all cases.

Kinetic studies showed that binding was complete within 5 min at 107° C. (5 min, 68%; 10 min, 61%; 15 min, 71%; and 30 min, 75%) with only moderate increases in isolated yield with reaction times as long as 30 min.

A radiolabeling reaction of IMP 467 performed at 50° C. showed that no binding was achieved at the lower temperature.

High-Dose Radiolabeling of IMP 467

Five microliters of 2 mM $Al^{3+}$ stock solution were mixed with 50 µL of $^{18}F$ 1.3 GBq (35 mCi) followed by the addition of 20 µL of 2 mM IMP 467 in 0.1 mM, pH 4.1 acetate buffer. The reaction solution was heated to 104° C. for 15 min and then purified on an HLB column (~10 min) as described above, isolating 0.68 GBq (18.4 mCi) of the purified peptide in 69% radiochemical yield with a specific activity of 17 GBq/µmol (460 Ci/mmol). The reaction time was 15 min and the purification time was 12 min. The reaction was started 10 min after the 1.3 GBq (35 mCi) $^{18}F$ was purified, so the total time from the isolation of the $^{18}F$ to the purified final product was 37 min with a 52% yield without correcting for decay.

Human Serum Stability Test

An aliquot of the HLB purified peptide (~30 µL) was diluted with 200 µL human serum (previously frozen) and placed in the 37° C. HPLC sample chamber. Aliquots were removed at various time points and analyzed by HPLC. The HPLC analysis showed very high stability of the $^{18}F$-labeled peptides in serum at 37° C. for at least five hours (not shown). There was no detectable breakdown of the $^{18}F$-labeled peptide after a five hour incubation in serum (not shown).

The IMP 461 and IMP 462 ligands have two carboxyl groups available to bind the aluminum whereas the NOTA ligand in IMP 467 had four carboxyl groups. The serum stability study showed that the complexes with IMP 467 were stable in serum under conditions replicating in vivo use. Further, the in vivo biodistribution studies with labeled IMP 467 show that the $^{18}F$—Al labeled peptide is stable under actual in vivo conditions.

Peptides can be labeled with $^{18}F$ rapidly (30 min) and in high yield by forming $Al^{18}F$ complexes that can be bound to a NOTA ligand on a peptide and at a specific activity of at least 17 GBq/µmol, without requiring HPLC purification. The $Al^{18}F$ NOTA-peptides are stable in serum and in vivo. Modifications of the NOTA ligand can lead to improvements in yield and specific activity, while still maintaining the desired in vivo stability of the $Al^{18}F$-NOTA complex, and being attached to a hydrophilic linker aids in the renal clearance of the peptide. Further, this method avoids the dry-down step commonly used to label peptides with $^{18}F$. As shown in the following Examples, this new $^{18}F$-labeling method is applicable to labeling of a broad spectrum of targeting peptides.

Example 19

Synthesis and Labeling of IMP 470

Figure 7:
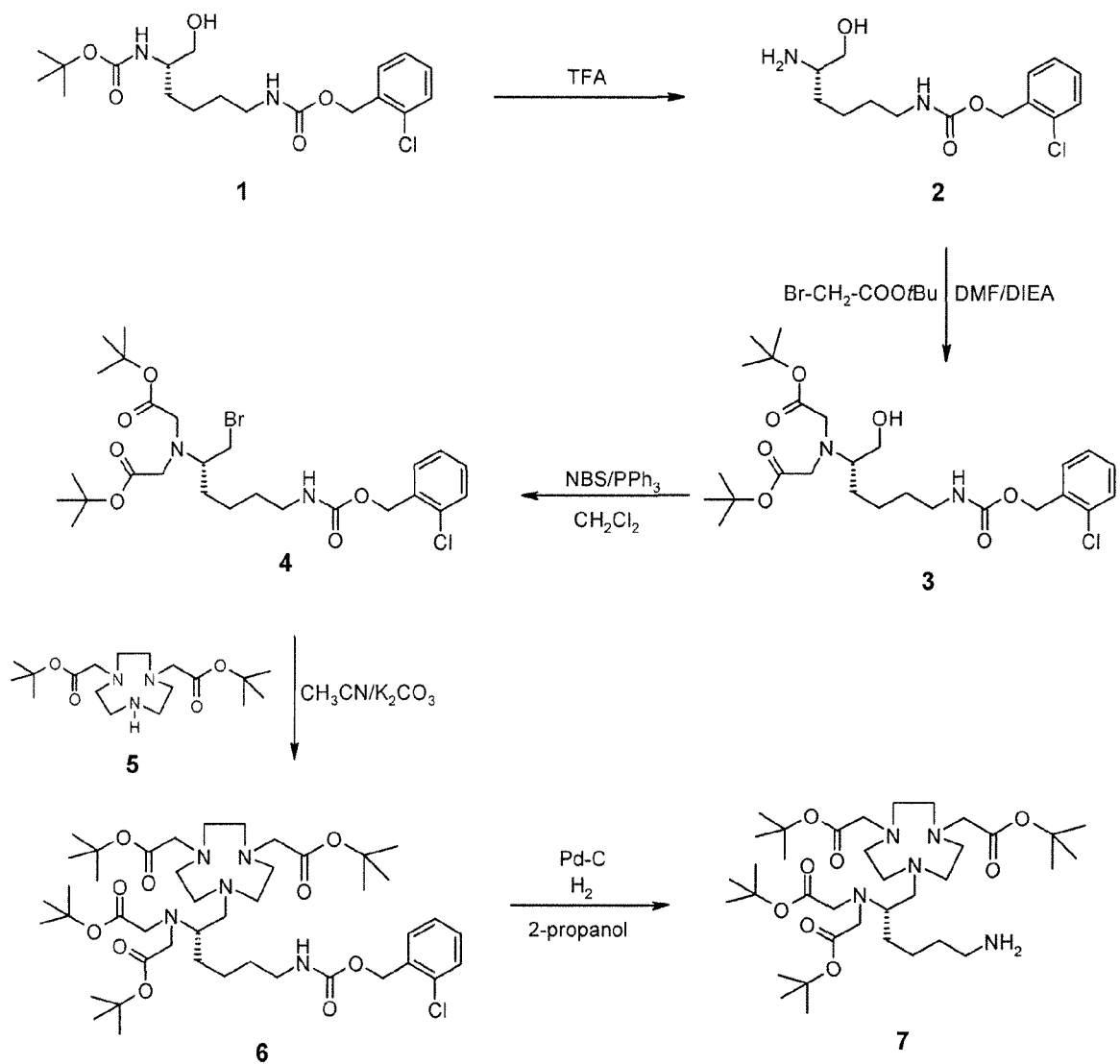
FIG. 7. Synthesis of tetra-tert-butyl L-NETA.
Figure 8:
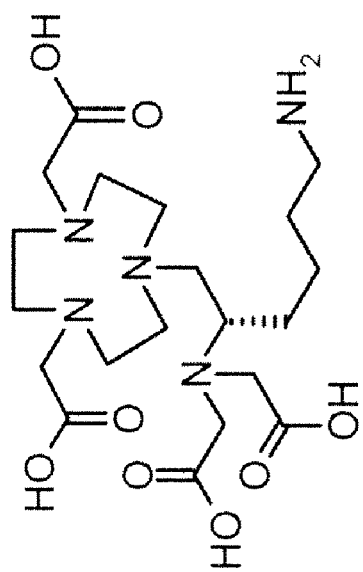
FIG. 8. Difference in structure between C-NETA and L-NETA.
Figure 8:
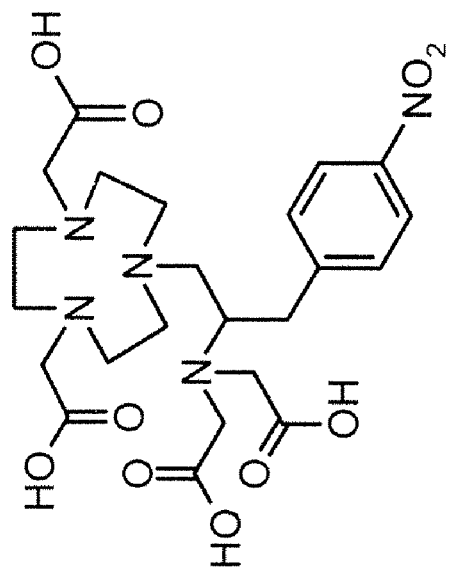

The results with IMP 467 prompted us to evaluate a more easily accessible bifunctional version of C-NETA (FIG. 8). The synthetic route to tetra tert-butyl L-NETA 7 (shown in FIG. 7) starts with Boc deprotection of 1 using TFA, followed by a double alkylation of 2 with t-butyl bromoacetate to yield alcohol 3. Reaction of 3 with $PPh_3$/NBS generates the bromide 4. Coupling of the bisubstituted TACN 5 in $CH_3CN$ with 4 using $K_2CO_3$ provided the macrocycle 6. tert-butyl protected L-NETA 7 is obtained by 2-Cl—Z deprotection using hydrogenation over Pd/C in near quantitative yield.

This free amine in 7 can be further converted to isothiocyanate, maleimide, bromo acetyl, or succinyl, making it a suitable group for conjugation to a tumor targeting peptide or antibody or a variety of other potential targeting moieties.

IMP 470 L-NETA-succinyl-D-Lys(HSG)-D-Tyr-D-Lys(HSG)-$NH_2$ $MH^+$ 1494.68

The peptide, IMP 470 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH. The free amine obtained after the removal of Aloc was reacted with succinic anhydride, to generate a carboxylic acid group at the N-terminus, which is activated using DIC in DMF and subsequently coupled with tert-butyl protected L-NETA 7. The peptide was then cleaved from the resin and purified by RP-HPLC to yield 16.4 mg of IMP 470. A product with molecular mass 1037.15 corresponding to the peptide without L-NETA and with retention time 9.001 min was also obtained.

For RP-HPLC analysis, a WATERS® 2695 HPLC system equipped with a PHENOMENEX® GEMINI™ $C_{18}$ reverse-phase column (4.6×250 mm), using a linear gradient of 100% A (0.1% TFA) to 100% B (90% acetonitrile, 10% water, 0.1% TFA) over 30 min at a flow rate of 1 mL/min, absorbance was detected at 220 nm. Radioactivity was measured by a PERKIN ELMER® 610TR Radiomatic Flow Scintillation Analyzer.

To prepare a 2 mM solution of IMP 470, 2.5 mg (1.67 μmol) IMP 470 (F.W. 1494.68) GG23-116-13 was dissolved in 836 μL 0.1 M NaOAc, pH 4.02

For $^{18}F$ labeling, to 3 μL 2 mM $AlCl_3$ solution was added 40 μL F-18 solution [1.736 mCi of $^{18}F$] followed by 20 μL (40 nmol) 2 mM IMP 470 solution and heated to 101° C. for 15 minutes. Reverse Phase HPLC analysis showed two radiolabeled peptide peaks at 26.10% (RT 8.90 min) and 47.29% (RT 9.30 min) and 26.61% of the activity eluted at the void volume of the column (2.70 min) (not shown).

TABLE 18

[$Al^{18}F$] IMP 470

| Name | Retention (mins) | Height (CPM) | Area (CPM) | % ROI (%) |
|---|---|---|---|---|
| Region 1 | 2.70 | 30060.0 | 74431.3 | 26.61 |
| Region 2 | 8.90 | 40620.0 | 73021.9 | 26.10 |
| Region 3 | 9.30 | 73150.0 | 132278.4 | 47.29 |
| 3 Peaks | | | 279731.6 | 100.00 |

The crude labeled peptide was purified by transferring the reaction solution into a 1 cc WATERS® HLB column and eluting with water to remove unbound $^{18}F$ followed by 1:1 EtOH/$H_2O$ to elute the $^{18}F$-labeled peptide. The crude reaction solution was pulled through the HLB column into a 5 mL vial and the column was washed with 3×1 mL fractions of water (365 μCi). The HLB column was then placed on a new 3 mL vial and eluted with 2×200 μL 1:1 EtOH/$H_2O$ to collect the labeled peptide (790 μCi). The reaction vessel retained 11.93 μCi, while the column retained 33.2 μCi of activity. The 790 μCi collected represents a recovery of 65.83% of labeled peptide.

An aliquot of the HLB purified $^{18}F$-labeled peptide was analyzed by RP-HPLC. Two products were detected—8.90 min 44.93%, 9.20 min 55.07% ($^{18}F$ was not detected in the void volume).

TABLE 19

HLB Purified AlF-18 IMP 470

| Name | Retention (mins) | Height (CPM) | Area (CPM) | % ROI (%) |
|---|---|---|---|---|
| Region 1 | 8.90 | 1670.0 | 3716.5 | 44.93 |
| Region 2 | 9.20 | 2070.0 | 4555.2 | 55.07 |
| 2 Peaks | | | 8271.7 | 100.00 |

Serum Stability of $^{18}F$— Labeled IMP 470 at 37° C.:

Sixty μL of the HLB column purified $^{18}F$-labeled peptide were mixed with 100 μL human serum and the sample was maintained at 37° C. during the entire RP-HPLC analysis.

TABLE 20

Serum Stability of AlF-18 IMP 470, t = 0

| Name | Retention (mins) | Height (CPM) | Area (CPM) | % ROI (%) |
|---|---|---|---|---|
| Region 1 | 8.90 | 6480.0 | 10402.5 | 36.33 |
| Region 2 | 9.30 | 8500.0 | 18234.3 | 63.67 |
| 2 Peaks | | | 28636.8 | 100.00 |

TABLE 21

Serum Stability of AlF-18 IMP 470, t = 4 hours at 37° C.

| Name | Retention (mins) | Height (CPM) | Area (CPM) | % ROI (%) |
|---|---|---|---|---|
| Region 1 | 8.90 | 5770.0 | 9756.9 | 22.97 |
| Region 2 | 9.30 | 17020.0 | 32719.0 | 77.03 |
| 2 Peaks | | | 42475.9 | 100.00 |

TABLE 22

Serum Stability of AlF-18 IMP 470, t = 4 hour at 37° C.

| Name | Retention (mins) | Height (CPM) | Area (CPM) | % ROI (%) |
|---|---|---|---|---|
| Region 1 | 8.90 | 3800.0 | 7857.0 | 21.07 |
| Region 2 | 9.20 | 12110.0 | 29429.3 | 78.93 |
| 2 Peaks | | | 37286.4 | 100.00 |

TABLE 23

Summary of Serum Stability of AlF-18 IMP 470

| IncubationTime/R.T. | 8.90 mins | 9.30 min |
|---|---|---|
| 0 | 36.33% | 63.67% |
| 1 h | 22.97% | 77.03% |
| 4 h | 21.07% | 78.93% |

In summary, an HSG containing peptide (IMP 470) linked to the bifunctional ligand L-NETA which has the macrocyclic NOTA and a neighboring bis(carboxymethyl) amine was successfully labeled with Al$^{18}$F. $^{18}$F incorporation using 40 nmol of IMP 470 was 65.83% and the HLB column purified peptide was stable in human serum for 4 h at 37° C. Under similar labeling conditions the radiochemical yield with 40 nmol of IMP 467 was 75.34%.

Example 20

Synthesis of IMP 469

Figure 9:
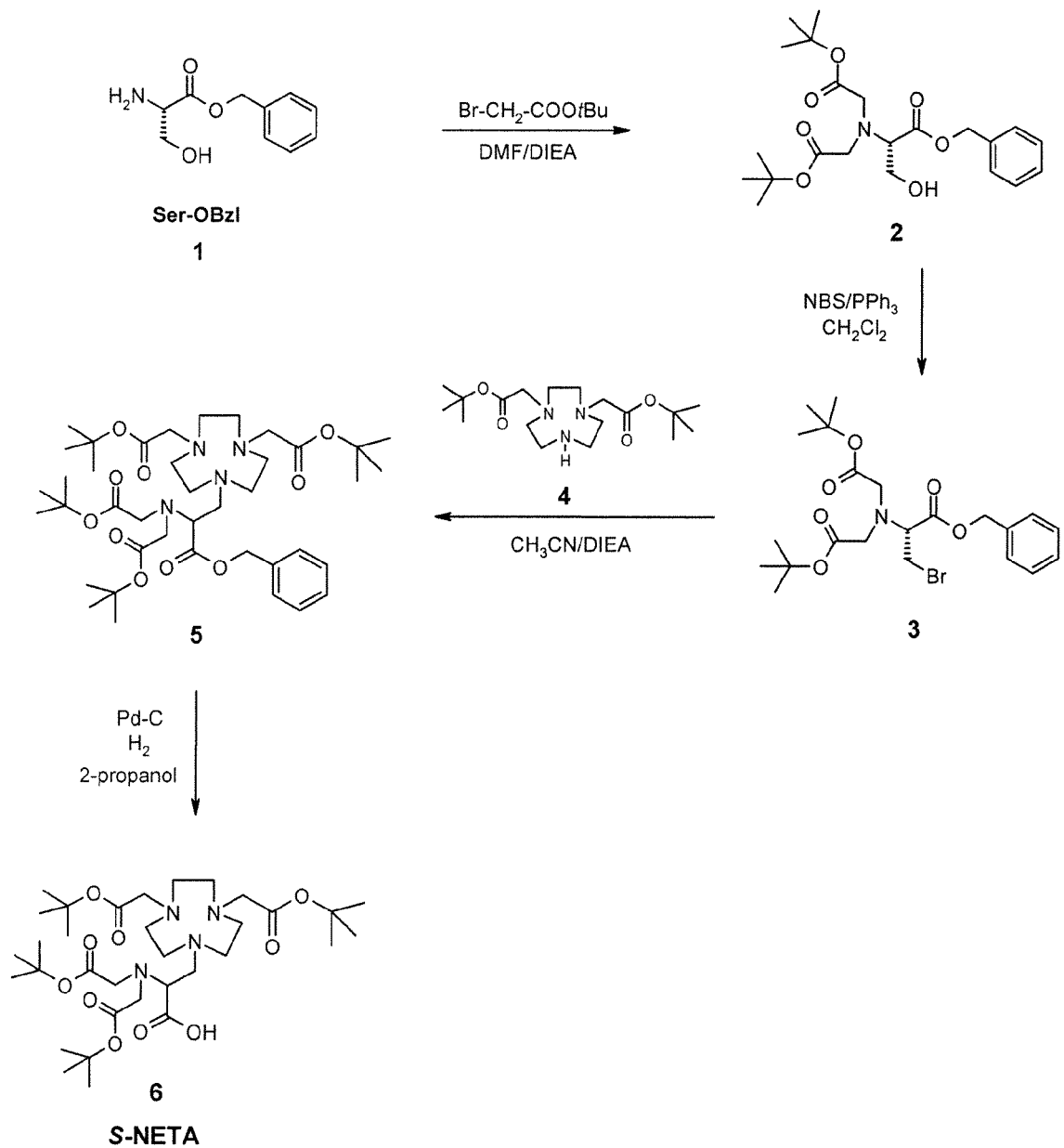
FIG. 9. Synthetic scheme for S-NETA.

An S-NETA conjugated targeting peptide, IMP 469, has been prepared, using the synthetic scheme shown in FIG. 9. The synthetic route starts with a double alkylation of 1 with t-butyl bromoacetate to yield alcohol 2. Reaction of 2 with PPh$_3$/NBS generates the bromide 3. Coupling of the bisubstituted TACN 4 in CH$_3$CN with 3 using DIEA provided the macrocycle 5. tert-butyl protected S-NETA 6 is obtained by benzyl deprotection using hydrogenation over Pd/C in near quantitative yield.

(t-BuO-CO—CH$_2$)$^2$-Ser-OBzl:

To a solution of 4.7945 g (20.70) H-Ser-OBzl.HCl in DMF (100 mL) at 0° C. were added diisopropylethylamine (50 mL) and tert-Butyl bromoacetate (9 mL, 90.90 mmol) dropwise over 2 h. The resultant mixture was stirred for 2 h at 0° C. and for 4 days at room temperature. The solvents were evaporated and the crude was dissolved in EtOAc. The EtOAc extract was washed with ABS pH 5.3, NaHCO$_3$ solution, brine, dried over anhydrous Na$_2$SO$_4$, filtered, and the filtrate concentrated under vacuum to provide 8.962 g of a yellow oil.

(t-BuO-CO—CH$_2$)$^2$-β-bromo-Ala-OBzl:

To a solution of 6.493 g (15.33 mmol) (t-BuO-CO—CH$_2$)-Ser-OBzl in anhydrous CH$_2$Cl$_2$ (100 mL) at 0° C. were added triphenylphosphine (4.0319 g, 15.37 mmol) and N-bromosuccinimide (2.7694 g, 15.56 mmol) in small portions over 1 h. The reaction mixture was stirred at for 30 min at 0° C. and 3 h at room temperature. The solvent was evaporated and the brown oil was purified using column chromatography (silica gel, 230-400 mesh) eluted with 10% EtOAc in hexanes to provide 4.778 g of a brown oil.

(t-BuO-CO—CH$_2$)$^2$-Ala(NOTA)-OBzl:

To a solution of 85.8 mg (0.240 mmol) of NO$_2$AtBu in CH$_3$CN (3 mL) were added 100 μL diisopropylethylamine and 154 mg (0.317 mmol) (t-BuO-CO—CH$_2$)$^2$-β-bromo-Ala-OBzl and the resultant solution stirred at room temperature. After 31 h solvent was evaporated and the crude was purified by preparative RP-HPLC to yield 167.8 mg of the desired product.

t-BuO-CO—CH$_2$)$^2$-Ala(NOTA):

To a solution of 167.9 mg (0.220 mmol) of (t-BuO-CO—CH$_2$)-Ala(NOTA)-OBzl in 2-propanol (50 mL) was added 10% Pd/C catalyst (146.8 mg). The resultant solution was subjected to hydrogenolysis by agitation with H$_2$ (g) at 50 psi in a Parr hydrogenator apparatus at room temperature for 5 h. The reaction mixture was filtered through celite, and the filtrate concentrated to yield dark brown oil (115.4 mg).

Example 21

Alternative NOTA Derivative Chelating Moieties

Figure 11:
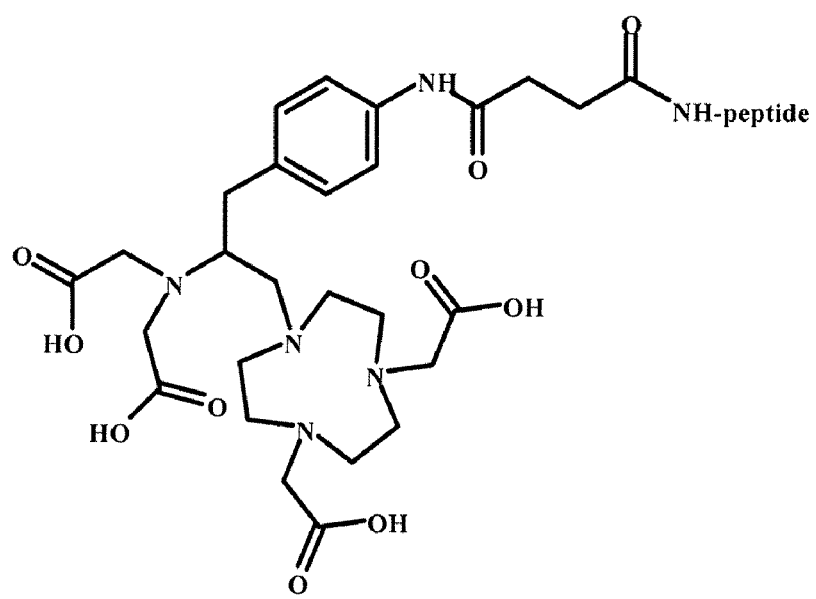
FIG. 11. NOTA derivatives. (A) NOTA ligand for IMP 467, (B) iminodiacetic acid derivatives of NOTA.
Figure 11:
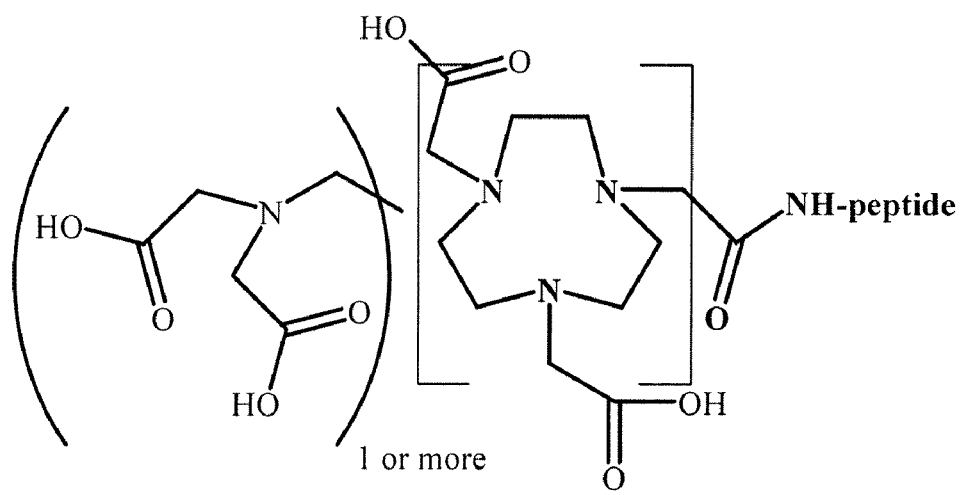
Figure 12:
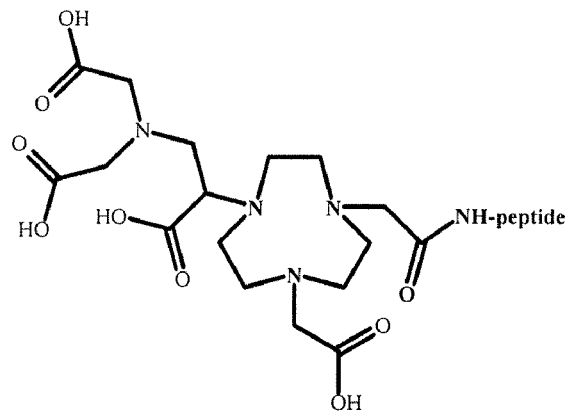
FIG. 12. Exemplary iminodiacetic acid derivatives of NOTA. (A) With one iminodiacetic acid off of a ring nitrogen. (B) With one iminodiacetic acid off of nitrogen and one attached to carbon. (C) With two iminodiacetic acid groups off of carbon.
Figure 12:
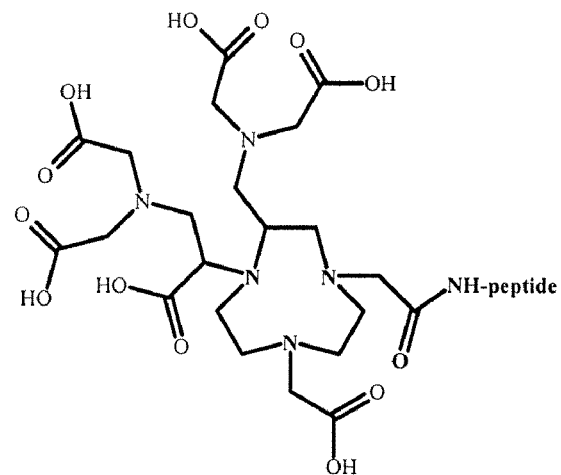
Figure 12:
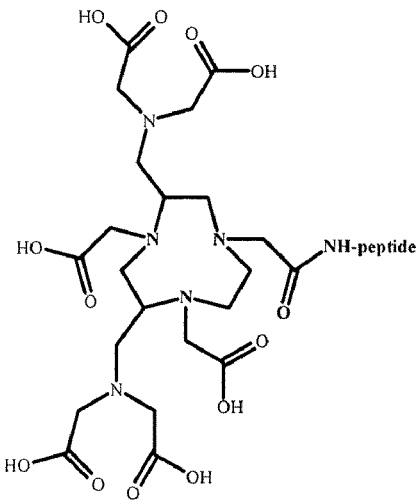

IMP 467 contains a NOTA derivative chelating moiety similar to that disclosed in Chong et al. (2002, J Med Chem 45:3458-64; 2008a, J Med Chem 51:118-25; 2008b, J Med Chem 51:2208-15), which has an iminodiacetic acid group off of a nitrogen (FIG. 11A). Since IMP 467 appears to display improved binding kinetics for Al$^{18}$F compared to other peptides examined above, additional NOTA derivatives are synthesized and examined for their Al$^{18}$F binding properties. The presence of multiple iminodiacetic acid groups or iminodiacetic acid groups in alternative locations is examined (FIG. 11B). Exemplary derivatives are shown in FIG. 12, containing one iminodiacetic acid group off of nitrogen (FIG. 12A), two iminodiacetic acid groups—one off of nitrogen and one attached to carbon (FIG. 12B) and two iminodiacetic acid groups off of carbon (FIG. 12C). When the groups are off of carbon, D or L versions of the amino acids could be used to adjust to make the groups syn or anti relative to each other. In addition the carboxyl group used to attach the NOTA to the peptide could be replaced by other linking agents known in the art. The linker could be attached through the nitrogen as shown (FIG. 11B) or attached through a carbon atom on the NOTA like IMP 449. Other binding enhancing groups (other than iminodiacetic acid) could be attached to a ligand to improve the binding of the metal-fluoride complex or to enhance the bind of fluoride to a metal that is already in the ligand. Some examples of other metal binding enhancing groups for ligands have been published by Kimura et al. (1987, J. Chem. Soc., Chem. Commun. 1712-14; 1986, Pure & Appl. Chem. 58(11), 1461-66; 1990, Inorg. Chem. 29, 4991-96; 1987, J. Am. Chem. Soc. 109, 5528-29; 1984, Inorg. Chem. 23, 4181-88; 1989, Pure & Appl. Chem. 61(5), 823-8.

Example 22

Labeling by Addition of $^{18}$F to a Peptide Pre-Incubated with Aluminum

An HSG containing peptide (IMP 465, NOTA-D-Ala-D-Lys(HSG)-D-Tyr-D-Lys(HSG)-NH$_2$) linked to macrocyclic NOTA complexed with aluminum, was successfully labeled with F-18. $^{18}$F incorporation using 40 nmol of IMP 465 was 13.20%. An intermediate peptide, IMP 461, was made as described above. Then 25.7 mg of IMP 461 was dissolved in 2 mL DI water to which was added 10.2 mg AlCl$_3$.3H$_2$O and the resultant solution heated to 100° C. for 1 h. The crude reaction mixture was purified by RP-HPLC to yield 19.6 mg of IMP 465. RP-HPLC analysis was performed as described above.

To prepare a 2 mM solution of IMP 465, 1.5 mg (1.14 μmol) IMP 465 (F.W. 1318.44) GG23-026-8 was dissolved in 569 μL 0.1 M NaOAc, pH 4.18

For $^{18}$F labeling, 50 µL $^{18}$F solution [0.702 mCi of $^{18}$F] and 20 µL (40 nmol) 2 mM IMP 465 solution was heated to 101° C. for 17 minutes. Reverse Phase HPLC analysis showed 15.38% (RT about 8.60 min) of the activity was attached to the peptide and 84.62% of the activity eluted at the void volume of the column (2.60 min).

TABLE 24

[Al$^{18}$F] IMP 465

| Name | Retention (mins) | Height (CPM) | Area (CPM) | % ROI (%) |
|---|---|---|---|---|
| Region 1 | 2.60 | 11380.0 | 25250.0 | 84.62 |
| Region 2 | 8.60 | 1880.0 | 4590.0 | 15.38 |
| 2 Peaks | | | 29840.0 | 100.00 |

The crude labeled peptide (377 µCi) was purified by transferring the reaction solution into a 1 cc Waters HLB column and eluting with water to remove unbound $^{18}$F followed by 1:1 EtOH/H$_2$O to elute the $^{18}$F-labeled peptide. The crude reaction solution was pulled through the HLB column into a 5 mL vial and the column was washed with 3×1 mL fractions of water (284 µCi). The HLB column was then placed on a new 3 mL vial and eluted with 2×200 µL 1:1 EtOH/H$_2$O to collect the labeled peptide (44.4 µCi, 13.2% of labeled peptide). The reaction vessel retained 4.54 µCi, while the column retained 3.39 µCi of activity after all of the elutions were performed.

In a separate experiment, the percent yield of $^{18}$F-labeled peptide could be improved by varying the amount of peptide added. In this experiment the reactions were all done in 63 µL total volume with the same amount of $^{18}$F. The percent yield observed for IMP 465 was 0.27% at 10 nmol peptide, 1.8% at 20 nmol of peptide and 49% at 40 nmol of peptide.

IMP 467 showed higher yield than IMP 461 when peptide was pre-incubated with aluminum before exposure to $^{18}$F. IMP 467 was incubated with aluminum at room temperature and then frozen and lyophilized. The amount of aluminum added for the pre-incubation was varied.

TABLE 25

Labeling of IMP 467 Pre-Incubated with Aluminum Before $^{18}$F is Added

| IMP 467 + Al Premixed, Frozen and Lyophilized | Isolated Labeling Yield |
|---|---|
| 40 nmol IMP 467 + 10 nmol Al Premix | 82% |
| 40 nmol IMP 467 + 20 nmol Al Premix* | 64% |
| 40 nmol IMP 467 + 30 nmol Al Premix | 74% |
| 40 nmol IMP 467 + 6 nmol Al Normal Labeling (Mix Al + $^{18}$F first) | 77% |

The yields were comparable to those obtained when IMP 467 is labeled by addition of an Al$^{18}$F complex. Thus, $^{18}$F labeling by addition of $^{18}$F to a peptide with aluminum already bound to the chelating moiety is a feasible alternative approach to pre-incubating the metal with $^{18}$F prior to addition to the chelating moiety.

Example 23

Synthesis and Labeling of IMP 468 Bombesin Peptide

As discussed above, the $^{18}$F labeled targeting moieties are not limited to antibodies or antibody fragments, but rather can include any molecule that binds specifically or selectively to a cellular target that is associated with or diagnostic of a disease state or other condition that may be imaged by $^{18}$F PET. Bombesin is a 14 amino acid peptide that is homologous to neuromedin B and gastrin releasing peptide, as well as a tumor marker for cancers such as lung and gastric cancer and neuroblastoma. IMP 468 (NOTA-NH—(CH$_2$)$_7$CO-Gln-Trp-Val-Trp-Ala-Val-Gly-His-Leu-Met-NH$_2$; SEQ ID NO:20) was synthesized as a bombesin analogue and labeled with $^{18}$F to target the gastrin-releasing peptide receptor.

The peptide was synthesized by Fmoc based solid phase peptide synthesis on Sieber amide resin, using a variation of a synthetic scheme reported in the literature (Prasanphanich et al., 2007, PNAS USA 104:12463-467). The synthesis was different in that a bis-t-butyl NOTA ligand was add to the peptide during peptide synthesis on the resin. In contrast, the 2007 report of Prasanphanich stated that the peptide was made first and then conjugated to unprotected NOTA in aqueous solution.

IMP 468 (0.0139 g, 1.02×10$^{-5}$ mol) was dissolved in 203 µL of 0.5 M pH 4.13 NaOAc buffer. The peptide dissolved but formed a gel on standing so the peptide gel was diluted with 609 µL of 0.5 M pH 4.13 NaOAc buffer and 406 µL of ethanol to produce an 8.35×10$^{-3}$ M solution of the peptide. The $^{18}$F was purified on a QMA cartridge and eluted with 0.4 M KHCO$_3$ in 200 µL fractions. Each of the $^{18}$F bicarbonate fractions was neutralized with 10 µL of glacial acetic acid. The purified $^{18}$F, 40 µL, 1.13 mCi was mixed with 3 µL of 2 mM AlCl$_3$ in pH 4, 0.1 M NaOAc buffer. IMP 468 (59.2 µL, 4.94×10$^{-7}$ mol) was added to the Al$^{18}$F solution and placed in a 108° C. heating block for 15 min. The crude product was diluted with water and placed on a WATERS® 30 mg, 1 cc syringe barrel, HLB column. The solution was eluted into a crimp sealed vial, which was under vacuum. The reaction vial was rinsed with 1 mL water, which was added to the HLB column. The column was then rinsed with 3×1 mL water. The column was moved to an empty vial and eluted with 2×200 µL of 1:1 EtOH/H$_2$O to obtain the purified $^{18}$F-labeled peptide in 34% yield.

TABLE 26

[Al$^{18}$F] IMP 468 after HLB purification

| Name | Start (mins) | End (mins) | Retention (mins) | Height (CPM) | Area (CPM) | % ROI (%) | % Total (%) |
|---|---|---|---|---|---|---|---|
| Bkg 1 | 0.00 | 1.10 | 0.50 | 130.0 | | | |
| Region 1 | 13.20 | 14.40 | 13.60 | 340.0 | 872.1 | 4.37 | 4.06 |
| Region 2 | 14.40 | 16.50 | 14.80 | 10100.0 | 19067.9 | 95.63 | 88.83 |
| Bkg 2 | 16.50 | 17.60 | 17.20 | 120.0 | | | |
| | | | | | 19940.0 | 100.00 | 92.89 |

| Total Area: | 21465.5 CPM |
|---|---|
| Average Background: | 59.0 CPM |
| Unallocated Area: | −16179.1 CPM |

The labeled peptide may be purified by HPLC for in-vivo targeting studies to increase the specific activity by separating the excess cold peptide from the [Al$^{18}$F] labeled peptide.

The cold [Al$^{19}$F] labeled peptide was also prepared for receptor binding competition studies. An 0.02 M AlCl$_3$ solution (604 µL, 1.208×10$^{-5}$ mol, in 0.5 M NaOAc, pH 4) was mixed with 130 µL, 0.1 M NaF (1.30×10$^{-5}$ mol) in 0.5 M NaOAc pH 4. The Al$^{19}$F solution was incubated at room temperature for 12 min and then added to 0.0165 g, 1.21×10$^{-5}$ mol of IMP 468. The solution was heated in a 103° C. heating block for 16 min. Analytical HPLC of the crude product showed two main products one, 0.0034 g at 13.8 min (Al-IMP 468 MH⁺ 1391) and another, 0.0060 g at 14.8 min ([Al$^{19}$F] IMP 468 MH⁺ 1411, data not shown).

Example 24

Imaging of Tumors Using $^{18}$F Labeled Bombesin

A NOTA-conjugated bombesin derivative (IMP 468) was prepared as described above. We began testing its ability to block radiolabeled bombesin from binding to PC-3 cells as was done by Prasanphanich et al. (PNAS 104:12462-12467, 2007). Our initial experiment was to determine if IMP 468 could specifically block bombesin from binding to PC-3 cells. We used IMP 333 as a non-specific control. In this experiment, 3×10⁶ PC-3 cells were exposed to a constant amount (~50,000 cpms) of $^{125}$I-Bombesin (Perkin-Elmer) to which increasing amounts of either IMP 468 or IMP 333 was added. A range of 56 to 0.44 nM was used as our inhibitory concentrations.

The results showed that we could block the binding of $^{125}$I-BBN with IMP 468 but not with the control peptide (IMP 333) (not shown), thus demonstrating the specificity of IMP 468. Prasanphanich indicated an IC$_{50}$ for their peptide at 3.2 nM, which is approximately 7-fold lower than what we found with IMP 468 (21.5 nM).

This experiment was repeated using a commercially available BBN peptide. We increased the amount of inhibitory peptide to a range of 250 to 2 nM to block the $^{125}$I-BBN from binding to PC-3 cells. We observed very similar IC$_{50}$-values for IMP 468 and the BBN positive control with an IC$_{50}$-value higher (35.9 nM) than what was reported previously (3.2 nM) but close to what the BBN control achieved (24.4 nM).

To examine in vivo targeting, the distribution of Al$^{18}$F IMP 468 was examined in scPC3 prostate cancer xenograft bearing nude male mice; alone vs blocked with bombesin. For radiolabeling, aluminum chloride (10 μL, 2 mM), 51.9 mCi of $^{18}$F (from QMA cartridge), acetic acid, and 60 μL of IMP 468 (8.45 mM in ethanol/NaOAc) were heated at 100° C. for 15 min. The reaction mixture was purified on reverse phase HPLC, collecting fractions every 0.25 min. Fractions 40 and 41 (3.56, 1.91 mci) were pooled and applied to HLB column for solvent exchange. The product was eluted in 800 μL (3.98 mCi) and 910 μCi remained on the column. ITLC developed in saturated NaCl showed 0.1% unbound activity.

Figure 10:
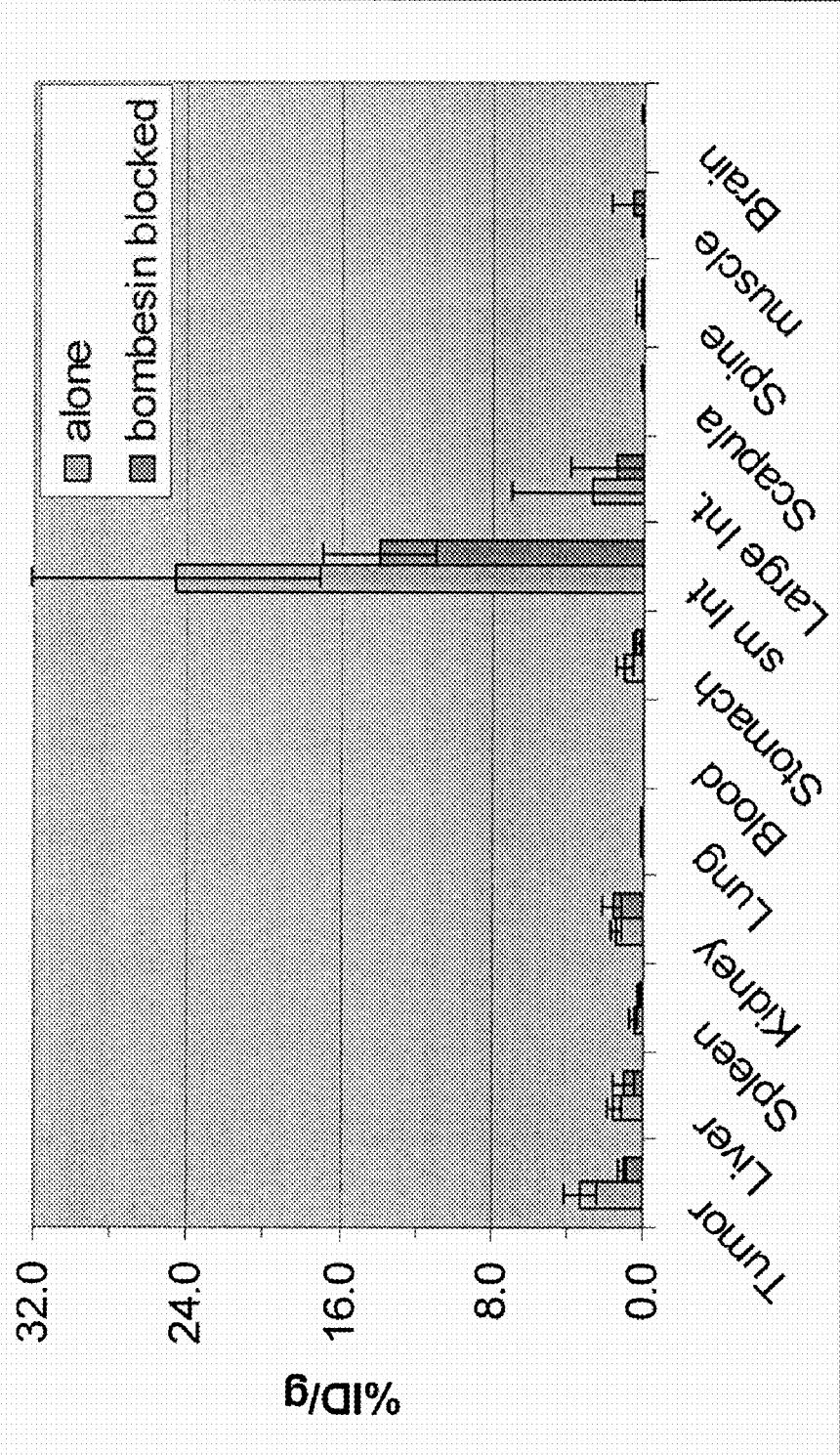
FIG. 10. In vivo tissue distribution with $^{18}$F-labeled IMP 468 bombesin analogue.

A group of six tumor-bearing mice were injected with [Al$^{18}$F] IMP 468 (167 μCi, ~9×10$^{-10}$ mol) and necropsied 1.5 h later. Another group of six mice were injected iv with 100 μg (6.2×10$^{-8}$ mol) of bombesin 18 min before administering [Al$^{18}$F] IMP 468. The second group was also necropsied 1.5 h post injection. The data shows specific targeting of the tumor with [Al$^{18}$F] IMP 468 (FIG. 10). Tumor uptake of the peptide is reduced when bombesin was given 18 min before the [Al$^{18}$F] IMP 468 (FIG. 10). Biodistribution data indicates in vivo stability of [Al$^{18}$F] IMP 468 for at least 1.5 h. Animal #1 in the peptide alone group showed slightly higher spine and muscle uptake, possibly due to contamination. Animal #2 in the bombesin blocked group showed higher peptide uptake in several tissues compared to the other mice in the group.

TABLE 27

[Al$^{18}$F] IMP 468 alone (167 μCi, ~9 × 10$^{-10}$ mol), % ID/g at 1.5 h post injection:

| Tissue | Mean | SD | Animal 1 | Animal 2 | Animal 3 | Animal 4 | Animal 5 | Animal 6 |
|---|---|---|---|---|---|---|---|---|
| Tumor | 3.216 | 0.859 | 2.356 | 4.206 | 4.111 | 3.546 | 2.802 | 2.274 |
| Tumor wt. g | 0.412 | 0.228 | 0.240 | 0.820 | 0.540 | 0.330 | 0.285 | 0.254 |
| Liver | 1.503 | 0.365 | 1.452 | 1.130 | 1.265 | 1.427 | 2.180 | 1.563 |
| Spleen | 0.446 | 0.210 | 0.251 | 0.744 | 0.285 | 0.609 | 0.525 | 0.260 |
| Kidney | 1.412 | 0.280 | 1.357 | 1.178 | 1.860 | 1.626 | 1.327 | 1.126 |
| Lung | 0.095 | 0.020 | 0.123 | 0.089 | 0.088 | 0.080 | 0.073 | 0.117 |
| Blood | 0.052 | 0.006 | 0.059 | 0.059 | 0.048 | 0.054 | 0.046 | 0.045 |
| Stomach | 1.006 | 0.452 | 1.251 | 0.772 | 0.552 | 0.505 | 1.530 | 1.424 |
| Sm. Int. | 24.587 | 7.511 | 29.629 | 20.362 | 32.347 | 13.302 | 30.816 | 21.065 |
| Large Int. | 2.765 | 4.168 | 0.579 | 0.868 | 0.635 | 11.202 | 2.035 | 1.273 |
| Scapula | 0.045 | 0.026 | 0.031 | 0.026 | 0.036 | 0.096 | 0.048 | 0.034 |
| Spine | 0.196 | 0.234 | 0.647 | 0.041 | 0.049 | 0.041 | 0.227 | 0.173 |
| muscle | 0.060 | 0.084 | 0.232 | 0.029 | 0.021 | 0.024 | 0.020 | 0.032 |
| Brain | 0.020 | 0.009 | 0.014 | 0.023 | 0.012 | 0.019 | 0.037 | 0.015 |
| Body Wt. | 28.82 | 2.31 | 28.04 | 28.74 | 28.18 | 29.61 | 25.64 | 32.68 |

Larger tumors showed higher uptake of [Al$^{18}$F] IMP 468, possibly due to higher receptor expression in larger tumors.

TABLE 28

Bombesin (100 μg, 6.2 × 10$^{-8}$ mol)→18 min → [Al$^{18}$F] IMP 468 (167 μCi, ~9 × 10$^{-10}$ mol), % ID/g at 1.5 h post injection

| Tissue | Mean | SD | Animal 1 | Animal 2 | Animal 3 | Animal 4 | Animal 5 | Animal 6 |
|---|---|---|---|---|---|---|---|---|
| Tumor | 1.053 | 0.200 | 0.842 | 0.998 | 1.220 | 1.296 | 1.147 | 0.814 |
| Tumor wt | 0.479 | 0.160 | 0.275 | 0.284 | 0.508 | 0.577 | 0.607 | 0.623 |
| Liver | 1.005 | 0.553 | 0.939 | 1.244 | 1.982 | 0.813 | 0.428 | 0.627 |
| Spleen | 0.187 | 0.101 | 0.354 | 0.086 | 0.226 | 0.085 | 0.164 | 0.207 |
| Kidney | 1.613 | 0.450 | 2.184 | 1.965 | 1.841 | 1.432 | 1.067 | 1.189 |
| Lung | 0.114 | 0.035 | 0.125 | 0.084 | 0.149 | 0.083 | 0.086 | 0.159 |
| Blood | 0.033 | 0.006 | 0.029 | 0.043 | 0.031 | 0.032 | 0.037 | 0.025 |
| Stomach | 0.413 | 0.223 | 0.356 | 0.736 | 0.387 | 0.617 | 0.159 | 0.225 |

TABLE 28-continued

Bombesin (100 μg, 6.2 × 10⁻⁸ mol)→18 min → [Al¹⁸F] IMP 468 (167 μCi, ~9 × 10⁻¹⁰ mol), % ID/g at 1.5 h post injection

| Tissue | Mean | SD | Animal 1 | Animal 2 | Animal 3 | Animal 4 | Animal 5 | Animal 6 |
|---|---|---|---|---|---|---|---|---|
| Sm Int. | 13.890 | 3.024 | 16.266 | 12.387 | 11.312 | 18.805 | 13.249 | 11.321 |
| Large Int. | 1.359 | 2.452 | 0.556 | 0.352 | 0.264 | 0.235 | 6.359 | 0.388 |
| Scapula | 0.092 | 0.077 | 0.033 | 0.228 | 0.071 | 0.059 | 0.135 | 0.025 |
| Spine | 0.208 | 0.187 | 0.296 | 0.551 | 0.073 | 0.086 | 0.153 | 0.089 |
| muscle | 0.604 | 1.081 | 0.127 | 0.546 | 0.061 | 2.777 | 0.073 | 0.040 |
| Brain | 0.063 | 0.111 | 0.019 | 0.291 | 0.012 | 0.018 | 0.023 | 0.019 |
| Body Wt. | 29.36 | 1.45 | 29.72 | 31.85 | 29.02 | 27.38 | 29.09 | 29.08 |

The biodistribution data above showed [Al¹⁸F] IMP 468 tumor targeting that was in the same range as reported for the same peptide labeled with $^{68}$Ga by Prasanphanich et. al. The results demonstrate that the $^{18}$F peptide labeling method can be used in vivo to target receptors that are upregulated in tumors, using targeting molecules besides antibodies. In this case, the IMP 468 targeting took advantage of a naturally occurring ligand-receptor interaction. The tumor targeting was significant with a P value of P=0.0013. Many such ligand-receptor pairs are known and any such targeting interaction may form the basis for $^{18}$F-imaging, using the methods described herein.

Example 25

Synthesis and Labeling of Somatostatin Analog IMP 466

Somatostatin is another non-antibody targeting peptide that is of use for imaging the distribution of somatostatin receptor protein. $^{123}$I-labeled octreotide, a somatostatin analog, has been used for imaging of somatostatin receptor expressing tumors (e.g., Kvols et al., 1993, Radiology 187: 129-33; Leitha et al., 1993, J Nucl Med 34:1397-1402). However, $^{123}$I has not been of extensive use for imaging because of its expense, short physical half-life and the difficulty of preparing the radiolabeled compounds. The $^{18}$F-labeling methods described herein would be preferred for imaging of somatostatin receptor expressing tumors.

IMP 466 NOTA-D-Phe-Cys-Phe-D-Trp-Lys-Thr-Cys-Thro1 MH⁺ 1305

A NOTA-conjugated derivative the somatostatin analog octreotide (IMP 466) was made by standard Fmoc based solid phase peptide synthesis, as described in the Examples above, to produce a linear peptide. The C-terminal Thro1 residue is threoninol. The peptide was cyclized by treatment with DMSO overnight.

The peptide, 0.0073 g, 5.59×10⁻⁶ mol was dissolved in 111.9 μL of 0.5 M pH 4 NaOAc buffer to make a 0.05 M solution of IMP 466. The solution formed a gel over time so it was diluted to 0.0125 M by the addition of more 0.5 M NaOAc buffer.

$^{18}$F was purified and concentrated with a QMA cartridge to provide 200 μL of $^{18}$F in 0.4 M KHCO$_3$. The bicarbonate solution was neutralized with 10 μL of glacial acetic acid. A 40 μL aliquot of the neutralized $^{18}$F eluent was mixed with 3 μL of 2 mM AlCl$_3$, followed by the addition of 40 μL of 0.0125 M IMP 466 solution. The mixture was heated at 105° C. for 17 min. The reaction was then purified on a Waters 1 cc (30 mg) HLB column by loading the reaction solution onto the column and washing the unbound $^{18}$F away with water (3 mL) and then eluting the radiolabeled peptide with 2×200 μL 1:1 EtOH water. The yield of the radiolabeled peptide after HLB purification was 34.6%. The radiolabeled peptide contained two radiometric peaks, which had an HPLC retention time that was close to the unlabeled IMP 466 retention time (not shown).

The cold Al¹⁹F peptide was also prepared for in-vitro competition assays. Both the radiolabeled HPLC and the cold Al¹⁹F peptide showed that two Al¹⁹F products were formed. These are possibly diastereomers.

A cold Al¹⁹F solution was prepared by mixing 356 μL of 0.02 M AlCl$_3$, 7.13×10⁻⁶ mol in 0.5 M pH 4 NaOAc with 71.3 μL 0.1 M, 7.13×10⁻⁶ mol NaF in 0.5 M pH 4 NaOAc. The Al¹⁹F solution was then mixed with the peptide, IMP 466, 0.0093 g, 7.13×10⁻⁶ mol and heated at 103° C. for 17 min. The reaction gave three main peaks by HPLC-one shorter retention time peak (13.5 min) and two longer retention time peaks (14.8 min and 14.9 min) (not shown). The retention time of IMP 466 was 14.7 min. The reaction mixture was purified by C$_{18}$ reverse phase HPLC. The shorter retention time (13.5 min) product corresponded to the peptide plus aluminum MH⁺ 1329.

The longer retention time products 14.8 and 14.9 min (0.0037 g) corresponded to the Al¹⁹F peptides with an MH⁺ 1349. Two Al¹⁸F products are formed in the radiometric trace, which correspond with the two Al ¹⁹F products for the cold peptide.

TABLE 29

[Al¹⁸F] IMP 466, HLB purified

| Name | Start (mins) | End (mins) | Retention (mins) | Height (CPM) | Area (CPM) | % ROI (%) | % Total (%) |
|---|---|---|---|---|---|---|---|
| Bkg 1 | 1.30 | 1.50 | 1.30 | 90.0 | | | |
| Region 1 | 14.40 | 15.40 | 14.80 | 4380.0 | 14737.8 | 100.00 | 79.62 |
| Bkg 2 | 22.50 | 22.60 | 22.50 | 70.0 | | | |
| Bkg 3 | 23.30 | 23.40 | 23.30 | 110.0 | | | |
| Peak | | | | | 14737.8 | 100.00 | 79.62 |

Example 26

Imaging of Neuroendocrine Tumors with an $^{18}$F— and $^{68}$Ga-Labeled IMP 466

Studies were performed to compare the PET images obtained using an $^{18}$F versus $^{68}$Ga-labeled somatostatin analogue peptide and direct targeting to somatostatin receptor expressing tumors.

Methods $^{18}$F labeling—IMP 466 was synthesized and $^{18}$F-labeled as described in the Example above, except that the amount of IMP 466 peptide was varied (100-500 μg). The distribution of $^{18}$F-labeled IMP 466 was compared with $^{68}$Ga-labeled IMP 466.

$^{68}$Ga labeling—IMP 466 was labeled with $^{68}$GaCl$_3$ eluted from a TiO$_2$-based 1,110 MBq $^{68}$Ge/$^{68}$Ga generator (Cyclotron Co. Ltd., Obninsk, Russia) using 0.1 M ultrapure HCl (J. T. Baker, Deventer, The Netherlands). Five 1 mL fractions were collected and an aliquot of the second fraction was used for labeling the peptide. IMP 466 was dissolved in 1.0 M HEPES buffer, pH 7.0. Four volumes of $^{68}$Ga eluate (120-240 MBq) were added and the mixture was heated at 95° C. for 20 min. Then 50 mM EDTA was added to a final concentration of 5 mM to complex the non-incorporated $^{68}$Ga$^{3+}$. The $^{68}$Ga-labeled IMP 466 was purified on an Oasis HLB cartridge and eluted with 50% ethanol.

HPLC analysis—The radiolabeled IMP 466 peptides were analyzed by RP-HPLC on an Agilent 1200 system (Agilent Technologies, Palo Alto, Calif., USA). A C18 column (Onyx monolithic, 4.6×100 mm, Phenomenex, Torrance, Calif., USA) was used at a flow rate of 2 mL/min using the following buffer system: Buffer A: 0.1% v/v TFA in water. Buffer B: 0.1% v/v TFA in acetonitrile. Gradient: 0-5 min 97% buffer A, 5-35 min 80% buffer B to 75% buffer A. The radioactivity of the eluate was monitored using an in-line NaI radiodetector (Raytest GmbH, Straubenhardt, Germany). Elution profiles were analyzed using Gina-star software (version 2.18, Raytest GmbH, Straubenhardt, Germany).

Octanol-water partition coefficient (log $P_{oct/water}$)—To determine the lipophilicity of the radiolabeled peptides, approximately 50,000 dpm of the radiolabeled peptide was diluted in 0.5 mL phosphate-buffered saline (PBS). An equal volume of octanol was added to obtain a binary phase system. After vortexing the system for 2 min, the two layers were separated by centrifugation (100×g, 5 min). Three 100 μL samples were taken from each layer and radioactivity was measured in a well-type gamma counter (Wallac Wizard 3", Perkin-Elmer, Waltham, Mass.).

Stability—Ten μL of the $^{18}$F-labeled IMP 466 was incubated in 500 μL of freshly collected human serum and incubated for 4 h at 37° C. Acetonitrile was added and the mixture was vortexed followed by centrifugation at 1000×g for 5 min to precipitate serum proteins. The supernatant was analyzed on RP-HPLC as described above.

Cell culture—The AR42J rat pancreatic tumor cell line was cultured in Dulbecco's Modified Eagle's Medium (DMEM) medium (Gibco Life Technologies, Gaithersburg, Md., USA) supplemented with 4500 mg/L D-glucose, 10% (v/v) fetal calf serum, 2 mmol/L glutamine, 100 U/mL penicillin and 100 μg/mL streptomycin. Cells were cultured at 37° C. in a humidified atmosphere with 5% $CO_2$.

$IC_{50}$ determination—The 50% inhibitory concentration ($IC_{50}$) of IMP 466 was determined on AR42J cells grown in DMEM medium, 4500 mg/L D-glucose, 10% fetal calf serum, 2 mmol/L glutamine, 100 U/mL penicillin and 100 μg/mL streptomycin in 6-wells plates. Cells were incubated in binding buffer (HEPES-buffered RPMI containing 1% BSA) for 10 min at 37° C., unlabeled IMP 466 was added at a final concentration ranging from 0.01-10 mmol together with $^{111}$In-DOTA-octreotate (50,000 dpm/2 ml). To prevent internalization, cells were incubated on ice for 4 h. The cell washed twice with binding buffer and cells were harvested with a cotton plug and the cell-associated activity was determined in the γ-counter.

Biodistribution studies—Male nude BALB/c mice (6-8 weeks) were injected subcutaneously in the right flank with 0.2 mL AR42J cell suspension of $10^7$ cells/mL. Approximately two weeks after tumor cell inoculation when tumors were 5-8 mm in diameter, 370 kBq $^{18}$F or $^{68}$Ga-labeled IMP 466 was administered intravenously (n=5). Separate groups (n=5) were injected with a 1.000-fold molar excess of unlabeled IMP 466. One group of three mice was injected with unchelated [Al$^{18}$F]. All mice were killed by $CO_2/O_2$ asphyxiation 2 h post-injection (p.i.). Organs of interest were collected, weighed and counted in a gamma counter. The percentage of the injected dose per gram tissue (% ID/g) was calculated for each tissue. The animal experiments were approved by the local animal welfare committee and performed according to national regulations.

PET/CT imaging—Mice with s.c. AR42J tumors were injected intravenously with 10 MBq Al $^{18}$F-IMP 466 or $^{68}$Ga-IMP 466. One and two hours after the injection of peptide, mice were scanned on an Inveon animal PET/CT scanner (Siemens Preclinical Solutions, Knoxville, Tenn.) with an intrinsic spatial resolution of 1.5 mm (Visser et al, JNM, 2009). The animals were placed in a supine position in the scanner. PET emission scans were acquired over 15 minutes, followed by a CT scan for anatomical reference (spatial resolution 113 μm, 80 kV, 500 μA). Scans were reconstructed using Inveon Acquisition Workplace software version 1.2 (Siemens Preclinical Solutions, Knoxville, Tenn.) using an ordered set expectation maximization-3D/maximum a posteriori (OSEM3D/MAP) algorithm with the following parameters: matrix 256×256×159, pixel size 0.43×0.43×0.8 mm$^3$ and MAP prior of 0.5 mm.

Statistical analysis—All mean values are given i standard deviation (S.D.). Statistical analysis was performed using a Welch's corrected unpaired t-test or one-way analysis of variance using GraphPad InStat software (version 4.00, GraphPad Software). The level of significance was set at $p<0.05$.

Results

Effect of buffer—The effect of the buffer on the labeling efficiency of IMP 466 was investigated. IMP 466 was dissolved in sodium citrate buffer, sodium acetate buffer, 2-(N-morpholino)ethanesulfonic acid (MES) or 4-(2-hydroxyethyl)-1-piperazineethanesulfonic acid (HEPES) buffer at 10 mg/mL (7.7 mM). The molarity of all buffers was 1 M and the pH was 4.1. To 200 μg (153 nmol) of IMP 466 was added 100 μL Al—F-18 (pH 4) and incubated at 100° C. for 15 min. Radiolabeling yield and specific activity was determined with RP-HPLC. When using sodium acetate, MES or HEPES, radiolabeling yield was 49%, 44% and 46%, respectively. In the presence of sodium citrate, no labeling was observed (<1%). When the labeling reaction was carried out in sodium acetate buffer, the specific activity of the preparations was 10,000 GBq/mmol, whereas in MES and HEPES buffer a specific activity of 20, 500 and 16,500 GBq/mmol was obtained, respectively.

Effect of AlCl$_3$ concentration—Three stock solutions of AlCl$_3$ in sodium acetate, pH 4.1 were prepared: 0.2, 2.0 and 20 mM. From these solutions, 3 μL was added to 200 μL of $^{18}$F to form [Al$^{18}$F]. To these samples, 153 nmol of peptide was added and incubated for 15 min at 100° C. Radiolabeling yield was 49% after incubation at a final concentration of 6 nmol AlCl$_3$. Incubation with 0.6 nmol AlCl$_3$ and 60 nmol AlCl$_3$ resulted in a strong reduction of the radiolabeling yield: 10% and 6%, respectively.

Effect of amount of peptide—The effect of the amount of peptide on the labeling efficiency was investigated. IMP 466 was dissolved in sodium acetate buffer, pH 4.1 at a concentration of 7.7 mM (10 mg/mL) and 38, 153 or 363 nmol of IMP 466 was added to 200 μL [Al$^{18}$F] (581-603 MBq). The radiolabeling yield increased with increasing amounts of peptide. At 38 mmol, radiolabeling yield ranged from 4-8%, at 153 nmol, the yield had increased to 42-49% and at the highest concentration the radiolabeling yield was 48-52%.

Octanol-water partition coefficient—To determine the lipophilicity of the $^{18}$F and $^{68}$Ga-labeled IMP 466, the octanol-water partition coefficients were determined. The log $P_{octanol/water}$ value for the Al$^{18}$F-IMP 466 was −2.44±0.12 and that of $^{68}$Ga-IMP 466 was −3.79±0.07, indicating that the $^{18}$F-labeled IMP 466 was slightly less hydrophilic.

Stability—The $^{18}$F-labeled IMP 466 did not show release of $^{18}$F after incubation in human serum at 37° C. for 4 h, indicating excellent stability of the Al$^{18}$F-NOTA complex.

Figure 13:
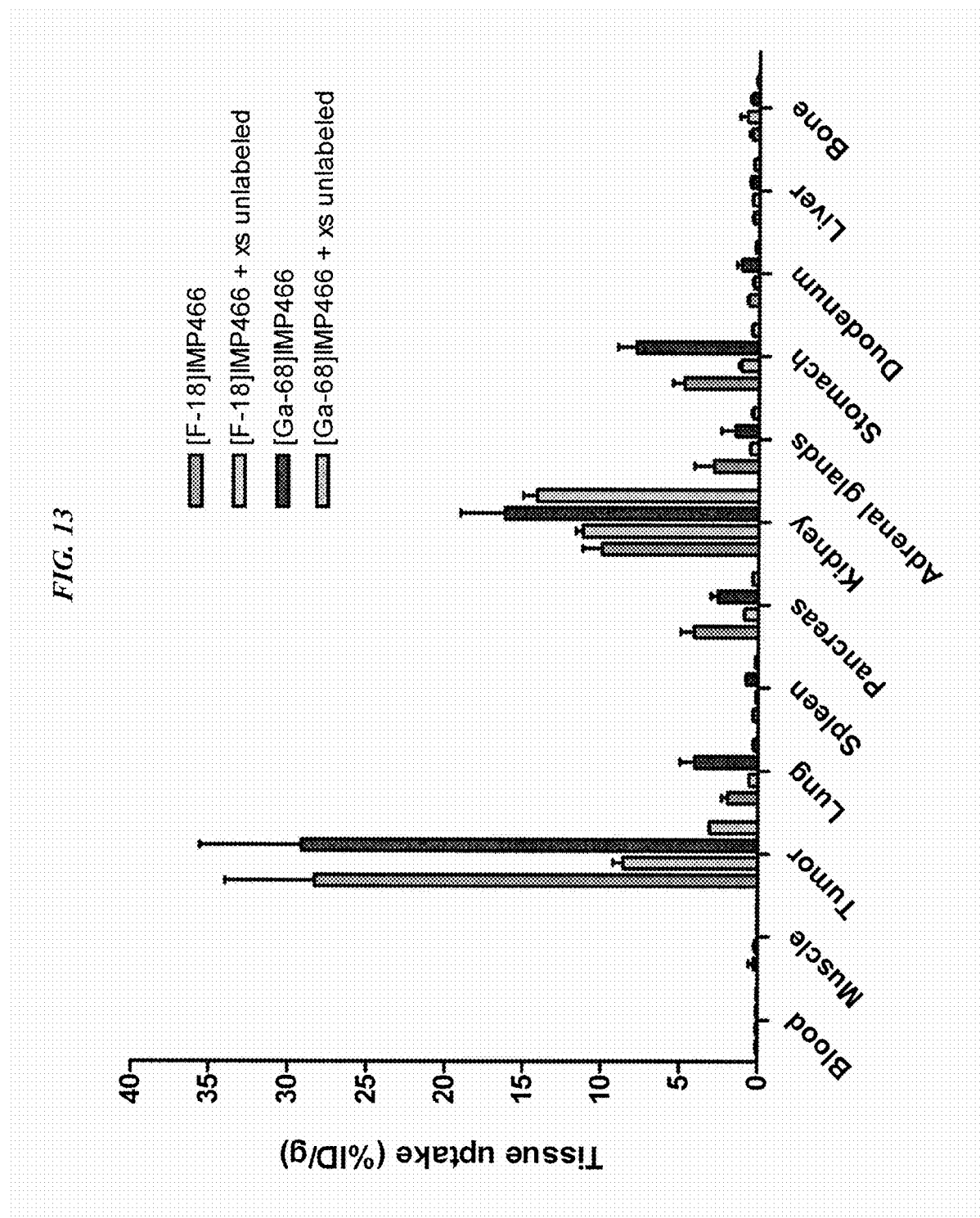
FIG. 13. Comparison of biodistribution of $^{18}$F-IMP 466 and $^{68}$Ga-IMP 466 at 2 h p.i. in AR42J tumor-bearing mice (n=5). As a control, mice in separate groups (n=5) received an excess of unlabeled octreotide to demonstrate receptor specificity.

Biodistribution studies—The biodistribution of both Al$^{18}$F-IMP 466 and $^{68}$Ga-IMP 466 was studied in nude BALB/c mice with s.c. AR42J tumors at 2 h p.i. (FIG. 13). Al$^{18}$F was included as a control. Tumor targeting of the $^{18}$F-IMP 466 was high with 28.3±5.7% ID/g accumulated at 2 h p.i. Uptake in the presence of an excess of unlabeled IMP 466 was 8.6±0.7% ID/g, indicating that tumor uptake was receptor-mediated. Blood levels were very low (0.10±0.07% ID/g, 2 h pi), resulting in a tumor-to-blood ratio of 299±88. Uptake in the organs was low, with specific uptake in receptor expressing organs such as adrenal glands, pancreas and stomach. Bone uptake of Al$^{18}$F-IMP 466 was negligible as compared to uptake of non-chelated Al$^{18}$F (0.33±0.07 vs 36.9±5.0% ID/g at 2 h p.i., respectively), indicating good in vivo stability of the $^{18}$F-labeled NOTA-peptide.

The biodistribution of Al$^{18}$F-IMP 466 was compared to that of $^{68}$Ga-IMP 466 (FIG. 13). Tumor uptake of $^{68}$Ga-IMP 466 (29.2±0.5% ID/g, 2 h pi) was similar to that of Al$^{18}$F-IMP 466 (p<0.001). Lung uptake of $^{68}$Ga-IMP 466 was two-fold higher than that of $^{18}$F-IMP 466 (4.0±0.9% ID/g vs. 1.9±0.4% ID/g, respectively). In addition, kidney retention of $^{68}$Ga-IMP 466 was slightly higher than that of Al$^{18}$F-IMP 466 (16.2±2.86% ID/g vs. 9.96±1.27% ID/g, respectively.

Figure 14:
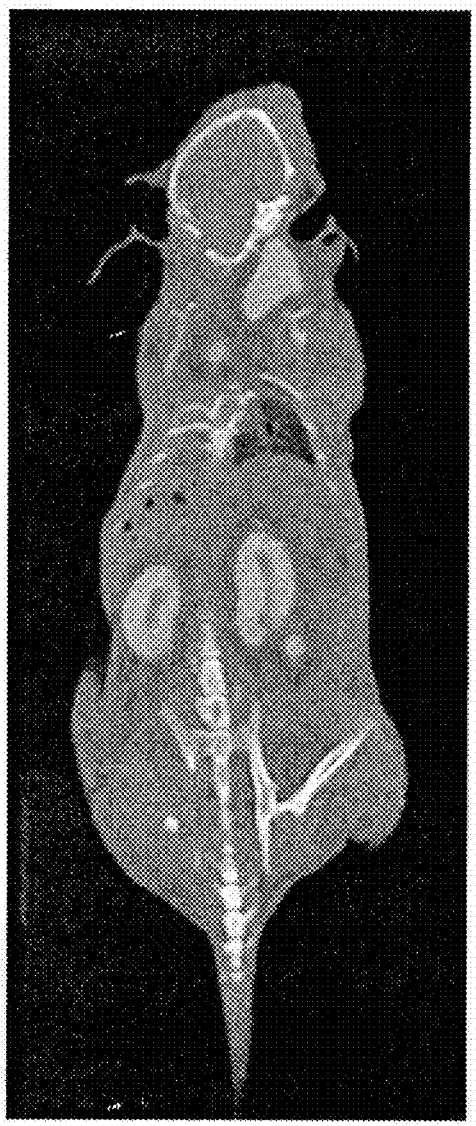
FIG. 14. Coronal slices of PET/CT scan of $^{18}$F-IMP 466 and $^{68}$Ga-IMP 466 at 2 h p.i. in mice with a s.c. AR42J tumor in the neck. Accumulation in tumor and kidneys is clearly visualized.
Figure 14:

Fused PET and CT scans are shown in FIG. 14. PET scans corroborated the biodistribution data. Both Al$^{18}$F-IMP 466 and $^{68}$Ga-IMP 466 showed high uptake in the tumor and retention in the kidneys. The activity in the kidneys was mainly localized in the renal cortex. Again, the Al$^{18}$F proved to be stably chelated by the NOTA chelator, since no bone uptake was observed.

FIG. 14 clearly shows that the distribution of an $^{18}$F-labeled analog of somatostatin (octreotide) mimics that of a $^{68}$Ga-labeled somatostatin analog. These results are significant, since $^{68}$Ga-labeled octreotide PET imaging in human subjects with neuroendocrine tumors has been shown to have a significantly higher detection rate compared with conventional somatostatin receptor scintigraphy and diagnostic CT, with a sensitivity of 97%, a specificity of 92% and an accuracy of 96% (e.g., Gabriel et al., 2007, J Nucl Med 48:508-18). PET imaging with $^{68}$Ga-labeled octreotide is reported to be superior to SPECT analysis with $^{111}$In-labeled octreotide and to be highly sensitive for detection of even small meningiomas (Henze et al., 2001, J Nucl Med 42:1053-56). Because of the higher energy of $^{68}$Ga compared with $^{18}$F, it is expected that $^{18}$F based PET imaging would show even better spatial resolution than $^{68}$Ga based PET imaging. This is illustrated in FIG. 14 by comparing the kidney images obtained with $^{18}$F-labeled IMP 466 (FIG. 14, left) vs. $^{68}$Ga-labeled IMP 466 (FIG. 14, right). The PET images obtained with $^{68}$Ga show more diffuse margins and lower resolution than the images obtained with $^{18}$F. These results demonstrate the superior images obtained with $^{18}$F-labeled targeting moieties prepared using the methods and compositions described herein and confirm the utility of the described $^{18}$F labeling techniques for non-antibody targeting peptides.

Example 27

Comparison of $^{68}$Ga and $^{18}$F PET Imaging Using Pretargeting

We compared PET images obtained using $^{68}$Ga- or $^{18}$F-labeled peptides that were pretargeted with the bispecific TF2 antibody, prepared as described above. The half-lives of $^{68}$Ga ($t_{1/2}$=68 minutes) and $^{18}$F ($t_{1/2}$=110 minutes) match with the pharmacokinetics of the radiolabeled peptide, since its maximum accretion in the tumor is reached within hours. Moreover, $^{68}$Ga is readily available from $^{68}$Ge/$^{68}$Ga generators, whereas $^{18}$F is the most commonly used and widely available radionuclide in PET.

Methods

Mice with s.c. CEA-expressing LS174T tumors received TF2 (6.0 nmol; 0.94 mg) and 5 MBq $^{68}$Ga-labeled IMP 288 (0.25 nmol) or $^{18}$F-labeled IMP 449 (0.25 nmol) intravenously, with an interval of 16 hours between the injection of the bispecific antibody and the radiolabeled peptide. One or two hours after the injection of the radiolabeled peptide, PET/CT images were acquired and the biodistribution of the radiolabeled peptide was determined. Uptake in the LS174T tumor was compared with that in a s.c. CEA-negative SK-RC 52 tumor. Pretargeted immunoPET imaging was compared with $^{18}$F-FDG-PET imaging in mice with a s.c. LS174T tumor and contralaterally an inflamed thigh muscle.

Pretargeting—The bispecific TF2 antibody was made by the DNL method, as described above. TF2 is a trivalent bispecific antibody comprising an HSG-binding Fab fragment from the h679 antibody and two CEA-binding Fab fragments from the hMN-14 antibody. The immunoreactive fraction of TF2 for binding to CEA, determined in a Lindmo assay (Lindmo et al., 1984, J Immunol Methods 72:77-89) on fixed LS174T cells, was 85%. The DOTA-conjugated, HSG-containing peptide IMP 288 was synthesized and purified as described above. The IMP 449 peptide, synthesized as described above, contains a 1,4,7-triazacyclononane-1,4,7-triacetic acid (NOTA) chelating moiety to facilitate labeling with $^{18}$F. As a tracer for the antibody component, TF2 was labeled with 125I (Perkin Elmer, Waltham, Mass.) by the iodogen method (Fraker and Speck, 1978, Biochem Biophys Res Comm 80:849-57), to a specific activity of 58 MBq/nmol. $^{125}$I-labeled TF2 was purified by eluting the reaction mixture with PBS, 0.5% w/v bovine serum albumin (BSA) (Sigma Chemicals, St. Louis, Mo., USA) on a PD-10 column (GE Healthcare Bio-sciences AB, Uppsala, Sweden).

Labeling of IMP 288—IMP 288 was labeled with $^{111}$In (Covidien, Petten, The Netherlands) for biodistribution studies at a specific activity of 32 MBq/nmol under strict metal-free conditions. After adding 11 MBq $^{111}$In to 12 µg IMP 288 dissolved in 0.25 M ammonium acetate (NH$_4$Ac) buffer, pH 5.6 in a metal-free vial, the mixture was incubated for 20 min at 95° C. in a heating block. Subsequently, 10 µL 50 mM ethylenediaminetetraacetic acid (EDTA) was added to complex the free $^{111}$In. IMP 288 was labeled with $^{68}$Ga eluted from a TiO-based 1,110 MBq $^{68}$Ge/$^{68}$Ga generator (Cyclotron Co. Ltd., Obninsk Russia) using 0.1 M ultrapure HCl. Five 1 ml fractions were collected and the second fraction was used for labeling the peptide. One volume of 1.0 M HEPES buffer, pH 7.0 was added to 3.4 mmole IMP 288. Four volumes of $^{68}$Ga eluate (380 MBq) were added and the mixture was heated to 95° C. for 20 min. Then 50 mM EDTA was added to a final concentration of 5 mM to complex the non-chelated $^{68}Ga^{3+}$. The $^{68}$Ga-labeled IMP 288 peptide was purified on a 1-mL Oasis HLB-cartridge (Waters, Milford, Mass.). After washing the cartridge with water, the peptide was eluted with 25% ethanol. The procedure to label IMP 288 with $^{68}$Ga was performed within 45 minutes, with the preparations being ready for in vivo use.

Labeling of IMP 449—IMP 449 was labeled with $^{18}$F as described above. 555-740 MBq $^{18}$F (B.V. Cyclotron VU, Amsterdam, The Netherlands) was eluted from a QMA cartridge with 0.4 M $KHCO_3$. Four 200-μL fractions were collected in vials containing 3 μL 2 mM $AlCl_3$ in 0.1 M sodium acetate buffer, pH 4. The fraction with highest activity was used. The $Al^{18}F$ activity was added to a vial containing the peptide (230 μg) and ascorbic acid (10 mg). The mixture was incubated at 100° C. for 15 min. The reaction mixture was purified by RP-HPLC on a Phenomenex Onyx monolithic $C_{18}$ column (Torrance, Calif., USA) eluted with a linear gradient of 97% A to 100% B in 30 min (Buffer A: 0.1% TFA in water; Buffer B: 0.1% TFA in acetonitrile, flow rate: 3 mL/min). After adding one volume of water, the peptide was purified on a 1-mL Oasis HLB cartridge. After washing with water, the radiolabeled peptide was eluted with 50% ethanol. $^{18}$F-IMP 449 was prepared within 60 minutes, with the preparations being ready for in vivo use.

Quality control of the radiolabeled preparations—Radiochemical purity was determined using instant thin-layer chromatography (ITLC) on silica-gel strips (Pall Life Sciences, Ann Arbor, Mich.) using 0.1 M citrate buffer, pH 6.0 as the mobile phase. The colloid content of the radiolabeled peptide was determined by ITLC-SG using a 1:1 v/v solution of 0.15 M $NH_4Ac$, pH 5.5: MeOH as the mobile phase. $^{111}$In-IMP 288, $^{68}$Ga-IMP 288 and $^{18}$F-IMP 449 were analyzed by RP-HPLC (Agilent 1100 series, Agilent Technologies, Palo Alto, Calif.) on a RP $C_{18}$ column (Alltima, 5 μm, 4.6×250 mm, Alltech, Deerfield, Ill., USA). The column was eluted at a flow rate of 1.0 ml/min with a linear gradient of 97% A and 3% to 100% B, over 15 min buffer A: 0.1% TFA in water and buffer B: 0.1% TFA in acetonitrile. Radiochemical purity of $^{125}$I-TF2, $^{111}$In- and $^{68}$Ga-IMP 288 and $Al^{18}F$-IMP 449 preparations used in the studies always exceeded 95%.

Animal experiments—Experiments were performed in male nude BALB/c mice (6-8 weeks old), weighing 20-25 grams. Mice received a subcutaneous injection with 0.2 mL of a suspension of 1×10⁶ LS174T cells, a CEA-expressing human colon carcinoma cell line (American Type Culture Collection, Rockville, Md., USA). Studies were initiated when the tumors reached a size of about 0.1-0.3 g (10-14 days after tumor inoculation).

The interval between TF2 and IMP 288 injection was 16 hours, as this period was sufficient to clear unbound TF2 from the circulation. In some studies $^{125}$I-TF2, (0.4 MBq) was co-injected with unlabeled TF2. IMP 288 was labeled with either $^{111}$In or $^{68}$Ga. IMP 449 was labeled with $^{18}$F. Mice received TF2 and IMP 288 intravenously (0.2 mL). One hour after the injection of $^{68}$Ga-labeled peptide, and two hours after injection of $^{18}$F-IMP 449, mice were euthanized by $CO_2/O_2$, and blood was obtained by cardiac puncture and tissues were dissected.

PET images were acquired with an Inveon animal PET/CT scanner (Siemens Preclinical Solutions, Knoxville, Tenn.) with an intrinsic spatial resolution of 1.5 mm (16). The animals were placed in a supine position in the scanner. PET emission scans were acquired for 15 minutes, preceded by CT scans for anatomical reference (spatial resolution 113 μm, 80 kV, 500 μA, exposure time 300 msec). Scans were reconstructed using Inveon Acquisition Workplace software (version 1.2, Siemens Preclinical Solutions, Knoxville, Tenn., USA) using a 3D ordered subset expectation maximization-/maximum a posteriori (OSEM3D/MAP) algorithm with the following parameters: matrix 256×256×159, pixel size 0.43× 0.43×0.8 $mm^3$ and MAP prior β of 0.5.

After imaging, tumor and organs of interest were dissected, weighed and counted in a gamma counter with appropriate energy windows for $^{125}$I, $^{111}$In, $^{68}$Ga or $^{18}$F. The percentage-injected dose per gram tissue (% ID/g) was calculated.

Statistic analysis—Statistical analysis was performed using a non-parametric, two-tailed Mann Whitney test using GraphPad InStat software (version 4.00, GraphPad Software). The level of significance was set at $p<0.05$.

Results

Within 1 hour, pretargeted immunoPET resulted in high and specific targeting of $^{68}$Ga-IMP 288 in the tumor (10.7±3.6% ID/g), with very low uptake in the normal tissues (e.g., tumor/blood 69.9±32.3), in a CEA-negative tumor (0.35±0.35% ID/g), and inflamed muscle (0.72±0.20% ID/g). Tumors that were not pretargeted with TF2 also had low $^{68}$Ga-IMP 288 uptake (0.20±0.03% ID/g). [$^{18}$F]FDG accreted efficiently in the tumor (7.42±0.20% ID/g), but also in the inflamed muscle (4.07±1.13% ID/g) and a number of normal tissues, and thus pretargeted $^{68}$Ga-IMP 288 provided better specificity and sensitivity. The corresponding PET/CT images of mice that received $^{68}$Ga-IMP 288 or $^{18}$F-labeled IMP 449 following pretargeting with TF2 clearly showed the efficient targeting of the radiolabeled peptide in the subcutaneous LS174T tumor, while the inflamed muscle was not visualized. In contrast, with [$^{18}$F]FDG the tumor as well as the inflammation was clearly delineated.

Dose optimization—The effect of the TF2 bsMAb dose on tumor targeting of a fixed 0.01 nmol (15 ng) dose of IMP 288 was determined. Groups of five mice were injected intravenously with 0.10, 0.25, 0.50 or 1.0 mmol TF2 (16, 40, 80 or 160 μg respectively), labeled with a trace amount of $^{125}$I (0.4 MBq). One hour after injection of $^{111}$In-IMP 288 (0.01 nmol, 0.4 MBq), the biodistribution of the radiolabels was determined.

Figure 15:
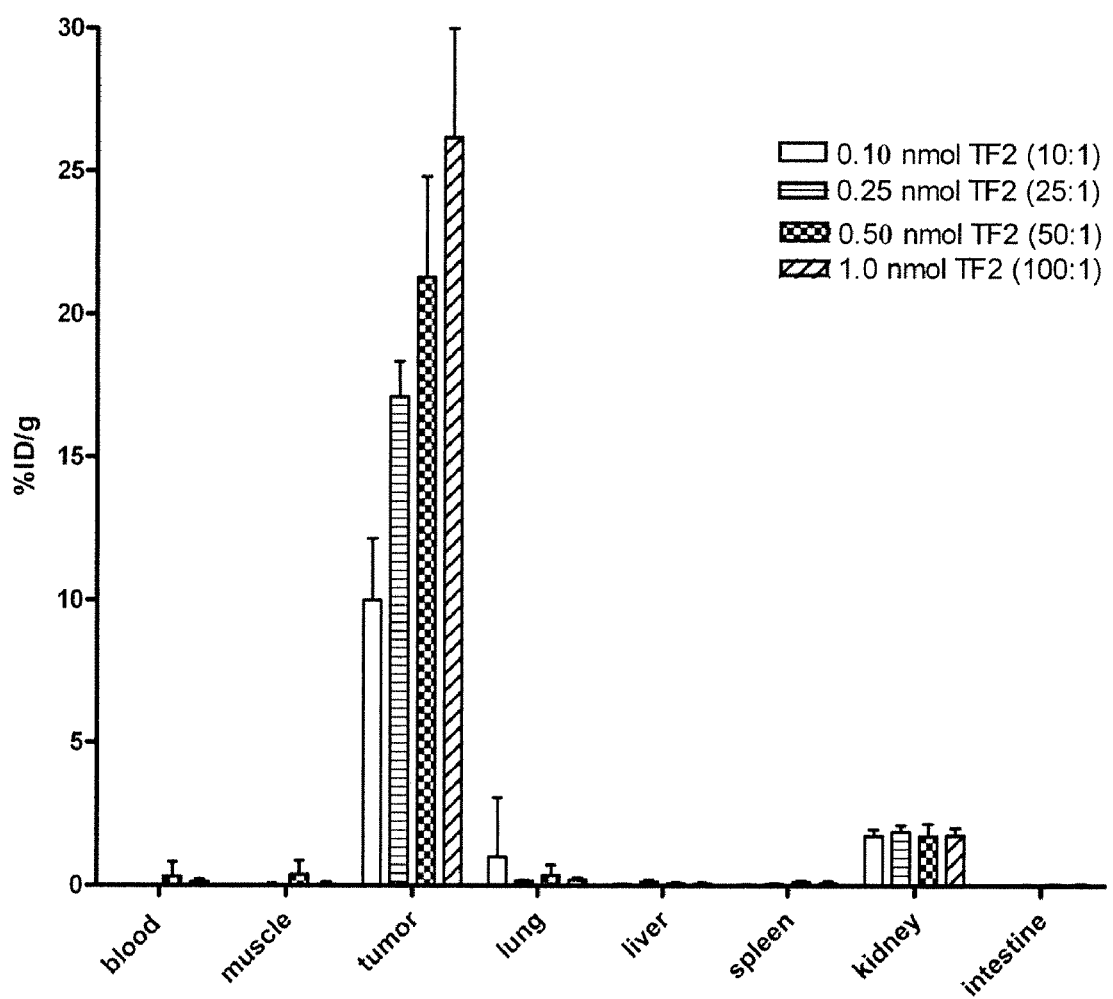
FIG. 15. Biodistribution of 0.01 nmol $^{111}$In-IMP 288 following pretargeting with escalating doses TF2. Values are given as means±standard deviation (n=5).

TF2 cleared rapidly from the blood and the normal tissues. Eighteen hours after injection the blood concentration was less than 0.45% ID/g at all TF2 doses tested. Targeting of TF2 in the tumor was 3.5% ID/g at 2 h p.i. and independent of TF2 dose (data not shown). The results of the $^{111}$In-IMP 288 uptake are summarized in FIG. 15. At all TF2 doses $^{111}$In-IMP 288 accumulated effectively in the tumor. At higher TF2 doses enhanced uptake of $^{111}$In-IMP 288 in the tumor was observed: at 1.0 nmol TF2 dose maximum targeting of IMP 288 was reached (26.2±3.8% ID/g). Thus at the 0.01 nmol peptide dose highest tumor targeting and tumor-to-blood ratios were reached at the highest TF2 dose of 1.0 nmol (TF2:IMP 288 molar ratio=100:1). Among the normal tissues, the kidneys had the highest uptake of $^{111}$In IMP 288 (1.75±0.27% ID/g) and uptake in the kidneys was not affected by the TF2 dose. All other normal tissues had very low uptake, resulting in extremely high tumor-to-nontumor ratios, exceeding 50:1 at all TF2 doses tested.

For PET imaging using $^{68}$Ga-labeled IMP 288, a higher peptide dose is required, because a minimum activity of 5-10 MBq $^{68}$Ga needs to be injected per mouse if PET imaging is performed 1 h after injection. The specific activity of the $^{68}$Ga-IMP 288 preparations was 50-125 MBq/nmol at the time of injection. Therefore, for PET imaging at least 0.1-0.25 nmol of IMP 288 had to be administered. The same TF2:IMP 288 molar ratios were tested at 0.1 nmol IMP 288 dose. LS174T tumors were pretargeted by injecting 1.0, 2.5, 5.0 or 10.0 mmol TF2 (160, 400, 800 or 1600 μg). In contrast to the results at the lower peptide dose, $^{111}$In-IMP 288 uptake in the tumor was not affected by the TF2 doses (15% ID/g at all doses tested, data not shown). TF2 targeting in the tumor in terms of % ID/g decreased at higher doses (3.21±0.61% ID/g versus 1.16±0.27% ID/g at an injected dose of 1.0 nmol and 10.0 nmol, respectively) (data not shown). Kidney uptake was also independent of the bsMAb dose (2% ID/g). Based on these data we selected a bsMAb dose of 6.0 nmol for targeting 0.1-0.25 mmol of IMP 288 to the tumor.

PET imaging—To demonstrate the effectiveness of pretargeted immunoPET imaging with TF2 and $^{68}$Ga-IMP 288 to image CEA-expressing tumors, subcutaneous tumors were induced in five mice. In the right flank a s.c. LS174T tumor was induced, while at the same time in the same mice 1×10$^6$ SK-RC 52 cells were inoculated in the left flank to induce a CEA-negative tumor. Fourteen days later, when tumors had a size of 0.1-0.2 g, the mice were pretargeted with 6.0 nmol $^{125}$I-TF2 intravenously. After 16 hours the mice received 5 MBq $^{68}$Ga-IMP 288 (0.25 nmol, specific activity of 20 MBq/nmol). A separate group of three mice received the same amount of $^{68}$Ga-IMP 288 alone, without pretargeting with TF2. PET/CT scans of the mice were acquired 1 h after injection of the $^{68}$Ga-IMP 288.

Figure 16:
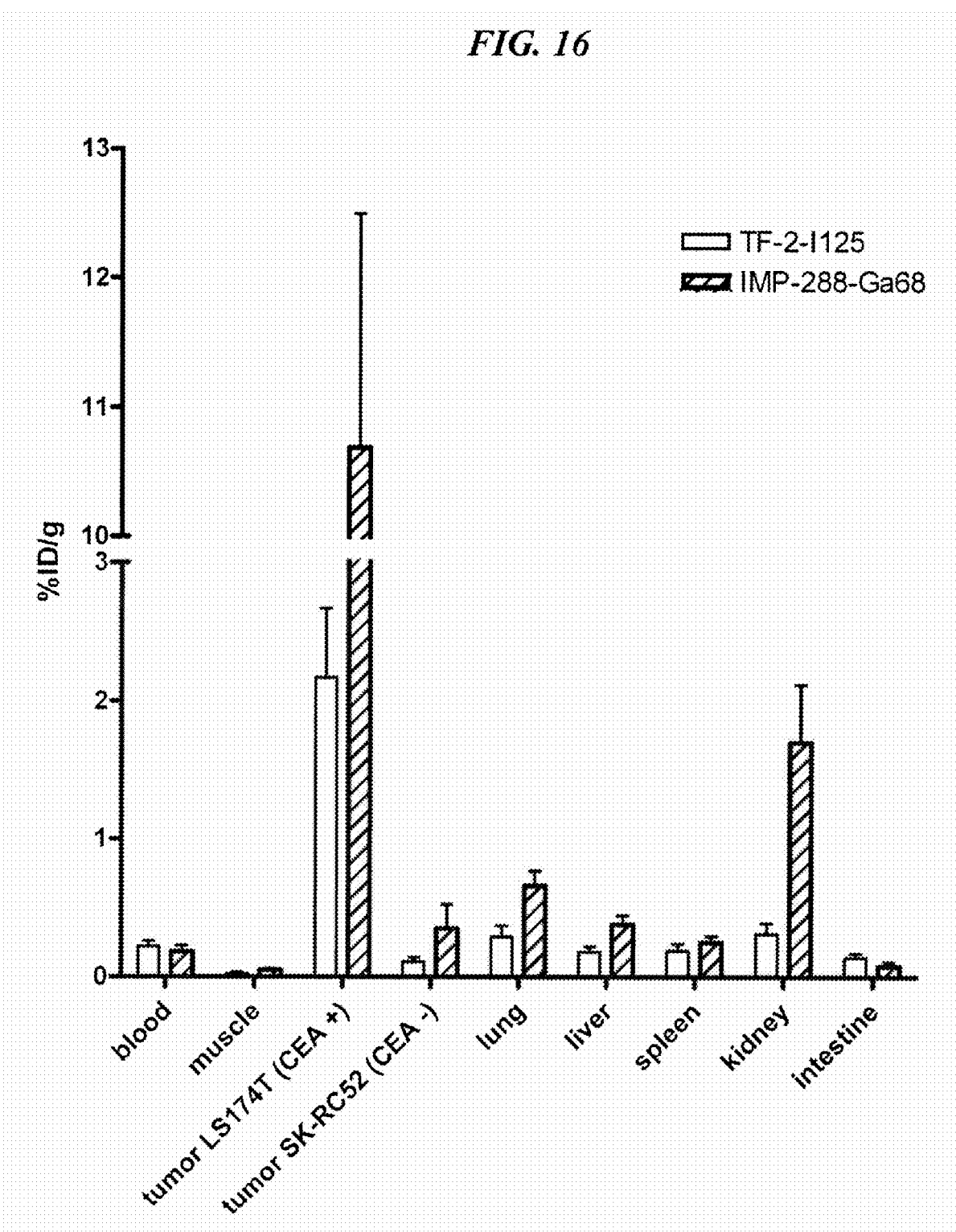
FIG. 16. Biodistribution of 6.0 nmol $^{125}$I-TF2 (0.37 MBq) and 0.25 nmol $^{68}$Ga-IMP 288 (5 MBq), 1 h after i.v. injection of $^{68}$Ga-IMP 288 in BALB/c nude mice with a subcutaneous LS174T and SK-RC52 tumor. Values are given as means±standard deviation (n=5).

The biodistribution of $^{125}$I-TF2 and $^{68}$Ga-IMP 288 in the mice are shown in FIG. 16. Again high uptake of the bsMAb (2.17±0.50% ID/g) and peptide (10.7±3.6% ID/g) in the tumor was observed, with very low uptake in the normal tissues (tumor-to-blood ratio: 64±22). Targeting of $^{68}$Ga-IMP 288 in the CEA-negative tumor SK-RC 52 was very low (0.35±0.35% ID/g). Likewise, tumors that were not pretargeted with TF2 had low uptake of $^{68}$Ga-IMP 288 (0.20±0.03% ID/g), indicating the specific accumulation of IMP 288 in the CEA-expressing LS174T tumor.

The specific uptake of $^{68}$Ga-IMP 288 in the CEA-expressing tumor pretargeted with TF2 was clearly visualized in a PET image acquired 1 h after injection of the $^{68}$Ga-labeled peptide (not shown). Uptake in the tumor was evaluated quantitatively by drawing regions of interest (ROI), using a 50% threshold of maximum intensity. A region in the abdomen was used as background region. The tumor-to-background ratio in the image of the mouse that received TF2 and $^{68}$Ga-IMP 288 was 38.2.

We then examined pretargeted immunoPET with [$^{18}$F] FDG. In two groups of five mice a s.c. LS174T tumor was induced on the right hind leg and an inflammatory focus in the left thigh muscle was induced by intramuscular injection of 50 μL turpentine (18). Three days after injection of the turpentine, one group of mice received 6.0 mmol TF2, followed 16 h later by 5 MBq $^{68}$Ga-IMP 288 (0.25 nmol). The other group received [$^{18}$F]FDG (5 MBq). Mice were fasted during 10 hours prior to the injection and anaesthetized and kept warm at 37° C. until euthanasia, 1 h post injection.

Figure 17:
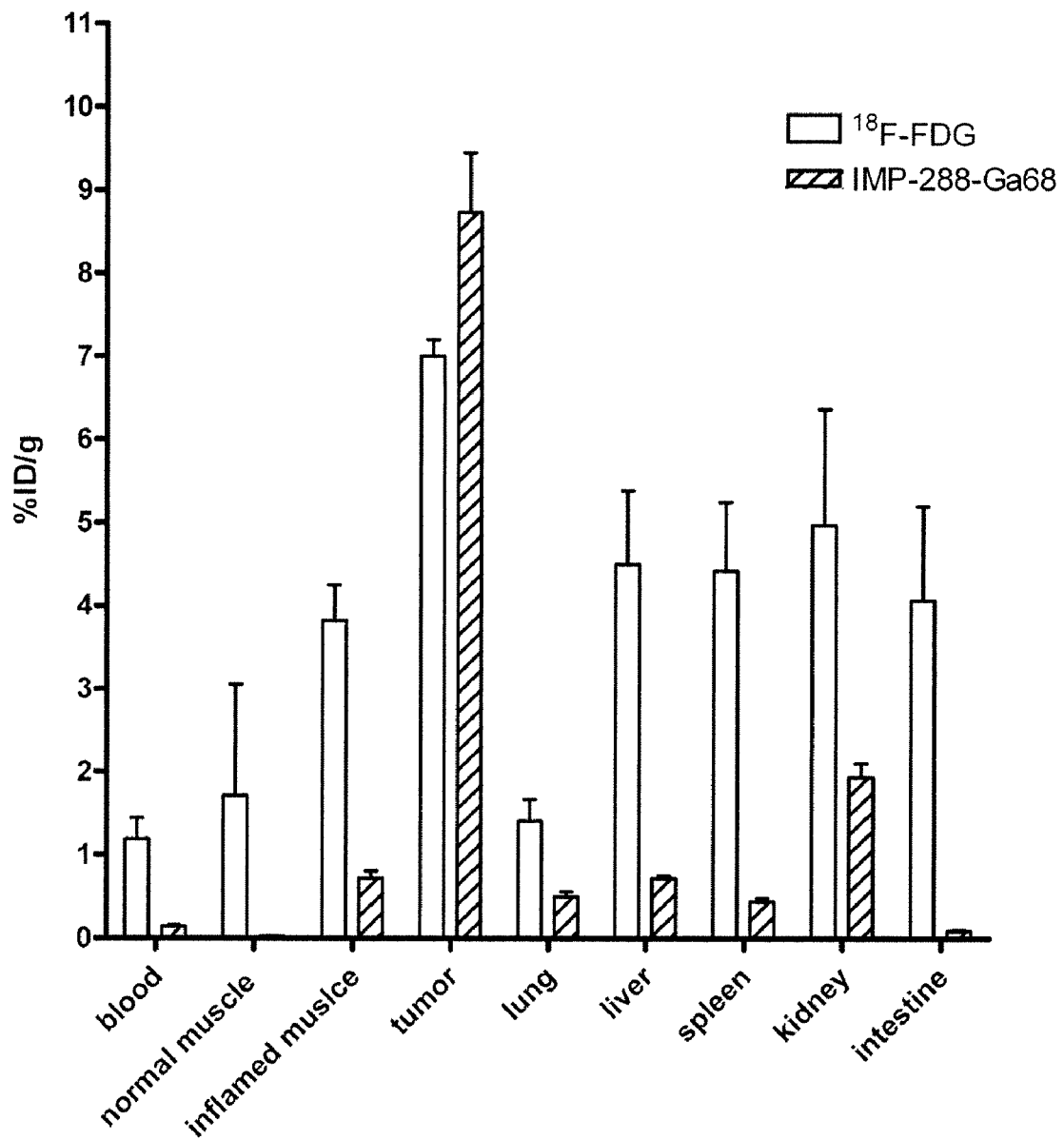
FIG. 17. Biodistribution of 5 MBq FDG and of 5 MBq $^{68}$Ga-IMP 288 (0.25 nmol) 1 hour after i.v. injection following pretargeting with 6.0 nmol TF2. Values are given as means±standard deviation (n=5).

Uptake of $^{68}$Ga-IMP 288 in the inflamed muscle was very low, while uptake in the tumor in the same animal was high (0.72±0.20% ID/g versus 8.73±1.60% ID/g, p<0.05, FIG. 17). Uptake in the inflamed muscle was in the same range as uptake in the lungs, liver and spleen (0.50±0.14% ID/g, 0.72±0.07% ID/g, 0.44±0.10% ID/g, respectively). Tumor-to-blood ratio of $^{68}$Ga-IMP 288 in these mice was 69.9±32.3; inflamed muscle-to-blood ratio was 5.9±2.9; tumor-to-inflamed muscle ratio was 12.5±2.1. In the other group of mice $^{18}$F-FDG accreted efficiently in the tumor (7.42±0.20% ID/g, tumor-to-blood ratio 6.24±1.5, FIG. 4). $^{18}$F-FDG also substantially accumulated in the inflamed muscle (4.07±1.13% ID/g), with inflamed muscle-to-blood ratio of 3.4±0.5, and tumor-to-inflamed muscle ratio of 1.97±0.71.

Figure 18:
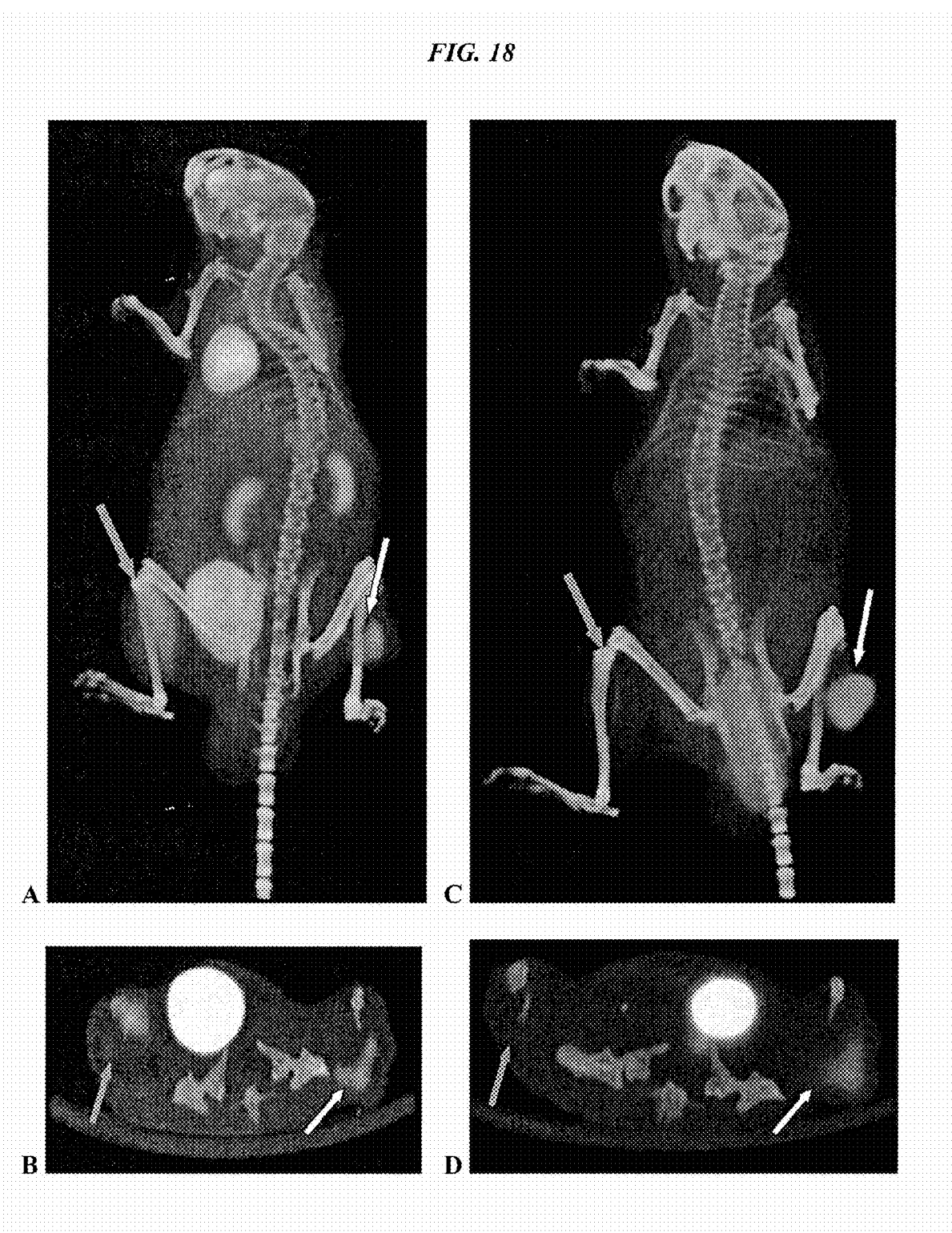
FIG. 18. PET/CT images of a BALB/c nude mouse with a subcutaneous LS174T tumor (0.1 g) on the right hind leg (light arrow) and a inflammation in the left thigh muscle (dark arrow), that received 5 MBq $^{18}$F-FDG, and one day later 6.0 nmol TF2 and 5 MBq $^{68}$Ga-IMP 288 (0.25 mmol) with a 16 hour interval. The animal was imaged one hour after the $^{18}$F-FDG and $^{68}$Ga-IMP 288 injection. The panel shows the 3D volume rendering (A), transverse sections of the tumor region (B) of the FDG-PET scan, and the 3D volume rendering (C), transverse sections of the tumor region (D) of the pretargeted immunoPET scan.

The corresponding PET/CT image of a mouse that received $^{68}$Ga-IMP 288, following pretargeting with TF2, clearly showed the efficient accretion of the radiolabeled peptide in the tumor, while the inflamed muscle was not visualized (FIG. 18). In contrast, on the images of the mice that received $^{18}$F-FDG, the tumor, as well as the inflammation were visible (FIG. 18). In the mice that received $^{68}$Ga-IMP 288, the tumor-to-inflamed tissue ratio was 5.4; tumor-to-background ratio was 48; inflamed muscle-to-background ratio was 8.9. [$^{18}$F] FDG uptake had a tumor-to-inflamed muscle ratio of 0.83; tumor-to-background ratio was 2.4; inflamed muscle-to-background ratio was 2.9.

Figure 19:
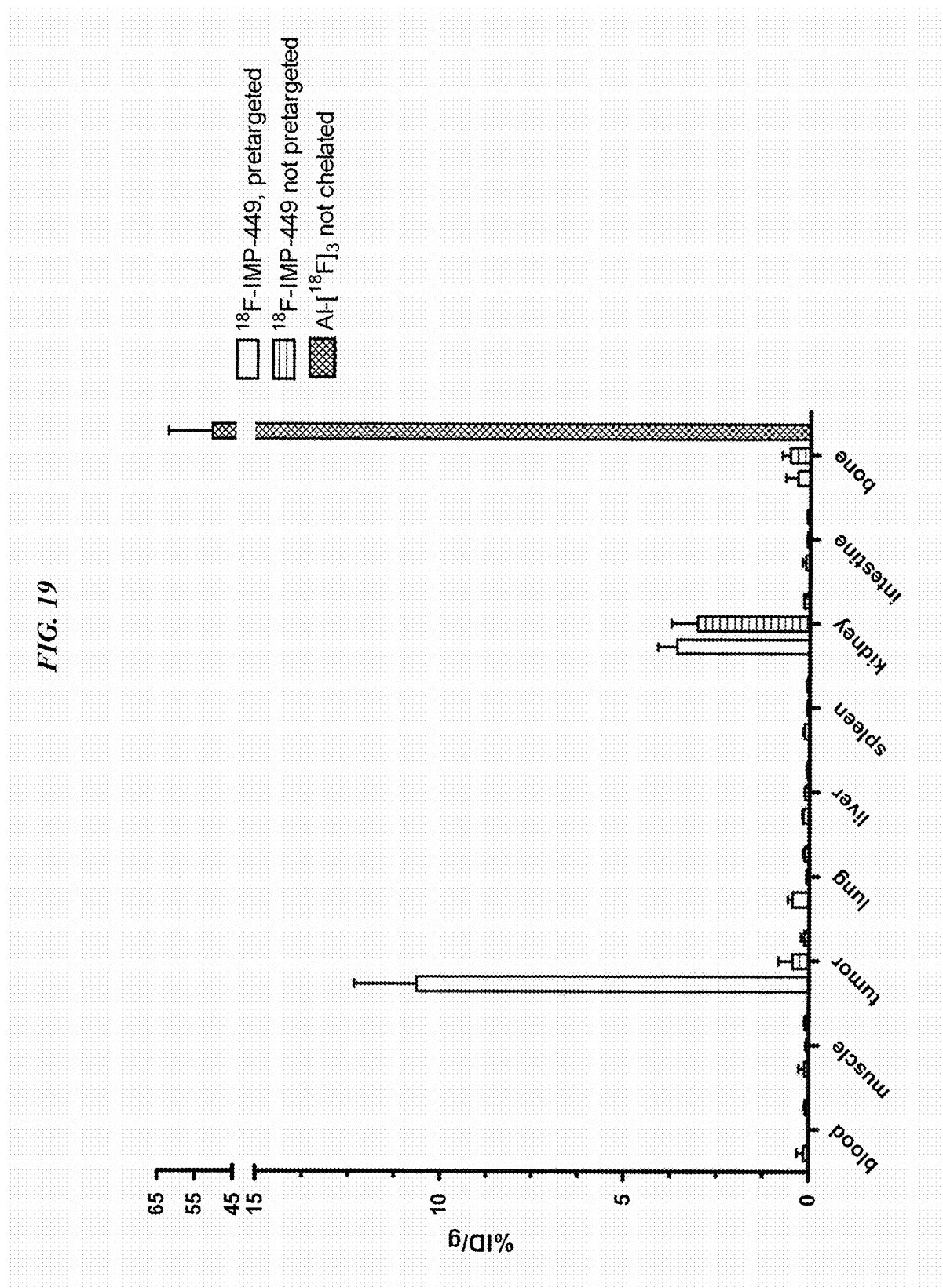
FIG. 19. Biodistribution of 0.25 nmol $Al^{18}F$-IMP 449 (5 MBq) 1 hour after i.v. injection of 6.0 nmol TF2 16 hours earlier, biodistribution of $Al^{18}F$-IMP 449 without pretargeting, or biodistribution of Al[$^{18}$F]. Values are given as means±standard deviation.

The pretargeted immunoPET imaging method was tested using the Al$^{18}$F-labeled IMP 449. Five mice received 6.0 nmol TF2, followed 16 h later by 5 MBq Al$^8$F-IMP 449 (0.25 nmol). Three additional mice received 5 MBq Al$^{18}$F-IMP 449 without prior administration of TF2, while two control mice were injected with [Al$^{18}$F] (3 MBq). The results of this experiment are summarized in FIG. 19. Uptake of Al$^{18}$F-IMP 449 in tumors pretargeted with TF2 was high (10.6±1.7% ID/g), whereas it was very low in the non-pretargeted mice (0.45±0.38% ID/g). [Al$^{18}$F] accumulated in the bone (50.9±11.4% ID/g), while uptake of the radiolabeled IMP 449 peptide in the bone was very low (0.54±0.2% ID/g), indicating that the Al$^{18}$F-IMP 449 was stable in vivo. The biodistribution of Al$^{18}$F-IMP 449 in the TF2 pretargeted mice with s.c. LS174T tumors were highly similar to that of $^{68}$Ga-IMP 288.

Figure 20:
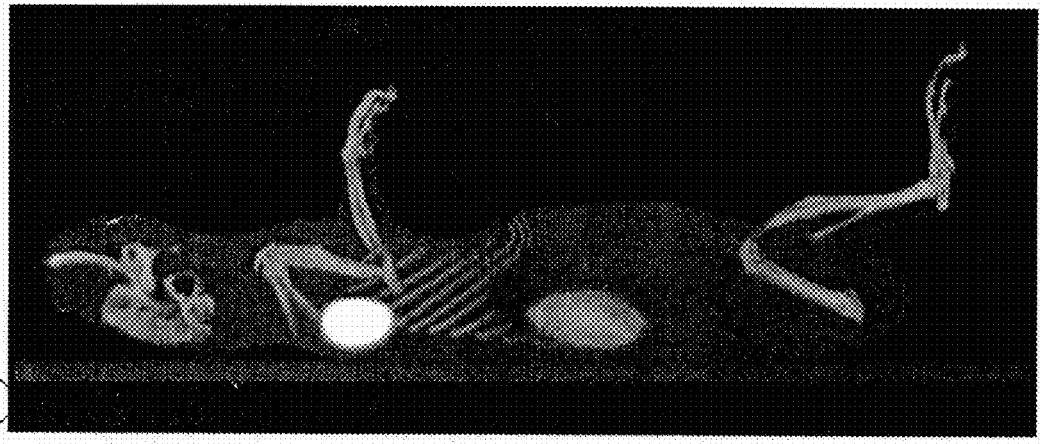
FIG. 20. Static PET/CT imaging study of a BALB/c nude mouse with a subcutaneous LS174T tumor (0.1 g) on the right side (arrow), that received 6.0 nmol TF2 and 0.25 nmol $Al^{18}F$-IMP 449 (5 MBq) intravenously with a 16 hour interval. The animal was imaged one hour after injection of $Al^{18}F$-IMP 449. The panel shows the 3D volume rendering (A) posterior view, and cross sections at the tumor region, (B) coronal, (C) sagital.
Figure 20:
Figure 20:
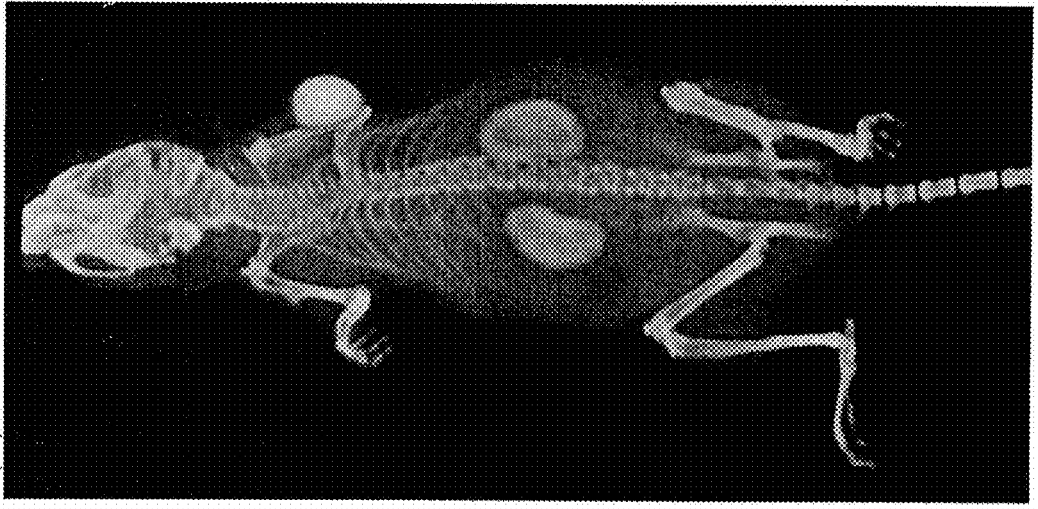

The PET-images of pretargeted immunoPET with Al$^{18}$F-IMP 449 show the same intensity in the tumor as those with $^{68}$Ga-IMP 288, but the resolution of the $^{18}$F-images was superior to those of the $^{68}$Ga-images (FIG. 20). The tumor-to-background ratio of the Al$^{18}$F-IMP 449 signal was 66.

Conclusions

The present study showed that pretargeted immunoPET with the anti-CEA× anti-HSG bispecific antibody TF2 in combination with a $^{68}$Ga- or $^{18}$F-labeled di-HSG-DOTA-peptide is a rapid and specific technique for PET imaging of CEA-expressing tumors. Pretargeted immunoPET with TF2 in combination with $^{68}$Ga-IMP 288 or Al$^{18}$F-IMP 449 involves two intravenous administrations. An interval between the infusion of the bsMAb and the radiolabeled peptide of 16 h was used. After 16 h most of the TF2 had cleared from the blood (blood concentration <1% ID/g), preventing complexation of TF2 and IMP 288 in the circulation.

For these studies the procedure to label IMP 288 with $^{68}$Ga was optimized, resulting in a one-step labeling technique. We found that purification on a C18/HLB cartridge was needed to remove the $^{68}$Ga colloid, that is formed when the peptide was labeled at specific activities exceeding 150 GBq/nmol at 95° C. If a preparation contains a small percentage of colloid and is administered intravenously, the $^{68}$Ga colloid accumulates in tissues of the mononuclear phagocyte system (liver, spleen, and bone marrow), detonating image quality. The $^{68}$Ga-labeled peptide could be rapidly purified on a C18-cartridge. Radiolabeling and purification for administration could be accomplished within 45 minutes.

The half-life of $^{68}$Ga matches with the kinetics of the IMP 288 peptide in the pretargeting system: maximum accretion in the tumor is reached within 1 h. $^{68}$Ga can be eluted twice a day form a $^{68}$Ge/$^{68}$Ga generator, avoiding the need for an on-site cyclotron. However, the high energy of the positrons emitted by $^{68}$Ga (1.9 MeV) limits the spatial resolution of the acquired images to 3 mm, while the intrinsic resolution of the microPET system is as low as 1.5 mm.

$^{18}$F, the most widely used radionuclide in PET, has an even more favorable half-life for pretargeted PET imaging ($t_{1/2}$=110 min). The NOTA-conjugated peptide IMP 449 was labeled with $^{18}$F, as described above. Like labeling with $^{68}$Ga, it is a one-step procedure. Labeling yields as high as 50% were obtained. The biodistribution of Al[18]F-IMP 449 was highly similar to that of $^{68}$Ga-labeled IMP 288, suggesting that with this labeling method $^{18}$F is a residualizing radionuclide.

In contrast with FDG-PET, pretargeted radioimmunodetection is a tumor specific imaging modality. Although a high sensitivity and specificity for FDG-PET in detecting recurrent colorectal cancer lesions has been reported in patients (Huebner et al., 2000, J Nucl Med 41:11277-89), FDG-PET images could lead to diagnostic dilemmas in discriminating malignant from benign lesions, as indicated by the high level of labeling observed with inflammation. In contrast, the high tumor-to-background ratio and clear visualization of CEA-positive tumors using pretargeted immunoPET with TF2 [68]Ga- or $^{18}$F-labeled peptides supports the use of the described methods for clinical imaging of cancer and other conditions. Apart from detecting metastases and discriminating CEA-positive tumors from other lesions, pretargeted immunoPET could also be used to estimate radiation dose delivery to tumor and normal tissues prior to pretargeted radioimmunotherapy. As TF2 is a humanized antibody, it has a low immunogenicity, opening the way for multiple imaging or treatment cycles.

Example 28

Synthesis of Folic Acid NOTA Conjugate

Folic acid is activated as described (Wang et. al. Bioconjugate Chem. 1996, 7, 56-62.) and conjugated to Boc-NH—CH$_2$—CH$_2$—NH$_2$. The conjugate is purified by chromatography. The Boc group is then removed by treatment with TFA. The amino folate derivative is then mixed with p-SCN-Bn-NOTA (Macrocyclics) in a carbonate buffer. The product is then purified by HPLC. The folate-NOTA derivative is labeled with Al $^{18}$F as described in the preceding Examples and then HPLC purified. The $^{18}$F-labeled folate is injected i.v. into a subject and successfully used to image the distribution of folate receptors, for example in cancer or inflammatory diseases (see, e.g., Ke et al., Advanced Drug Delivery Reviews, 56:1143-60, 2004).

Example 29

Pretargeted PET Imaging in Humans

A patient (1.7 m$^2$ body surface area) with a suspected recurrent tumor is injected with 17 mg of bispecific monoclonal antibody (bsMab). The bsMab is allowed to localize to the target and clear from the blood. The $^{18}$F-labeled peptide (5-10 mCi on 5.7×10$^{-9}$ mol) is injected when 99% of the bsMab has cleared from the blood. PET imaging shows the presence of micrometastatic tumors.

Example 30

Imaging of Angiogenesis Receptors by [18]F Labeling

Labeled Arg-Gly-Asp (RGD) peptides have been used for imaging of angiogenesis, for example in ischemic tissues, where $\alpha_v\beta_3$ integrin is involved. (Jeong et al., J. Nucl. Med. 2008, Apr. 15 epub). RGD is conjugated to SCN-Bn-NOTA according to Jeong et al. (2008). [Al[18]F] is attached to the NOTA-derivatized RGD peptide as described above, by mixing aluminum stock solution with $^{18}$F and the derivatized RGD peptide and heating at 110° C. for 15 min, using an excess of peptide to drive the labeling reaction towards completion. The $^{18}$F labeled RGD peptide is used for in vivo biodistribution and PET imaging as disclosed in Jeong et al. (2008). The [Al[18]F] conjugate of RGD-NOTA is taken up into ischemic tissues and provides PET imaging of angiogenesis.

Example 31

Use of [18]F-Labeled NOTA for Renal Flow Imaging

Aluminum stock solution (20 μL 0.05 M in pH 4 NaOAc buffer) is mixed with 200 μL of QMA purified [18]F. The [Al[18]F] solution is then mixed with 500 μL pH 4, 0.2 M NOTA and heated for 15 min. The sample is then diluted in 5 mL PBS for injection. The $^{18}$F labeled NOTA is used directly for successful renal flow imaging.

Example 32

Carbohydrate Labeling

A NOTA thiosemicarbazide derivative is prepared by reacting the p-SCN-Bn-NOTA with hydrazine and then purifying the ligand by HPLC. [Al[18]F] is prepared as described in the preceding Examples and the [Al[18]F] is added to the NOTA thiosemicarbazide and heated for 15 min. Optionally the [Al[18]F] NOTA thiosemicarbazide complex is purified by HPLC. The [Al[18]F] NOTA thiosemicarbazide is conjugated to oxidized carbohydrates by known methods. The $^{18}$F-labeled carbohydrate is successfully used for imaging studies using PET scanning.

Example 33

Lipid Labeling

A lipid comprising an aldehyde is conjugated to the [Al[18]F] NOTA thiosemicarbazide of Example 32 and the $^{18}$F-labeled lipid is used for successful imaging studies using PET scanning.

In an alternative embodiment, a lipid comprising an amino group is reacted with p-SCN-Bn-NOTA. The NOTA-labeled lipid is reacted with [Al[18]F] as described in the Examples above. The $^{18}$F-labeled lipid is used for successful imaging studies using PET scanning.

Example 34

Aptamer Labeling

An aptamer comprising an aldehyde is conjugated to the [Al[18]F] NOTA thiosemicarbazide of Example 32. The $^{18}$F-labeled aptamer is administered to a subject and used for successful imaging studies using PET scanning.

Example 35

Effect of Organic Solvents on F-18 Labeling

The affinity of chelating moieties such as NETA and NOTA for aluminum is much higher than the affinity of aluminum for [18]F. The affinity of Al for $^{18}$F is affected by factors such as the ionic strength of the solution, since the presence of other counter-ions tends to shield the positively charged aluminum and negatively charged fluoride ions from each other and therefore to decrease the strength of ionic binding. Therefore low ionic strength medium should increase the effective binding of Al and [18]F. It was considered possible that adding organic solvents to the medium, to decrease the hydrophilicity of the medium, might also increase the strength of ionic binding.

An initial study adding ethanol to the $^{18}F$ reaction was found to increase the yield of radiolabeled peptide. IMP 461 was prepared according to Example 15.

TABLE 30

$^{18}F$ labeling of IMP 461 in ethanol

| # | 2 mM AlCl$_3$ | F-18 | 2 mM IMP 461 | Solvent | | Yield* |
|---|---|---|---|---|---|---|
| 1 | 10 µL | 741 µCi | 20 µL | EtOH | 60 µL | 64.9% |
| 2 | 10 µL | 739 µCi | 20 µL | H$_2$O | 60 µL | 21.4% |
| 3 | 10 µL | 747 µCi | 20 µL | EtOH | 60 µL | 46.7% |
| 4 | 5 µL | 947 µCi | 10 µL | EtOH | 60 µL | 43.2% |

*Yield after HLB column purification, Rxn # 1,2 and 4 were heated to 101° C. for 5 minutes, Rxn # 3 was heated for 1 minute in a microwave oven.

Preliminary results showed that addition of ethanol to the reaction mixture more than doubled the yield of $^{18}F$-labeled peptide. Table 30 also shows that microwave irradiation can be used in place of heating to promote incorporation of [Al$^{18}F$] into the chelating moiety of IMP 461. Sixty seconds of microwave radiation (#3) appeared to be slightly less (18%) effective than heating to 101° C. for 5 minutes (#1).

The effects of additional solvents on $^{19}F$ labeling of peptides was examined. In each case, the concentration of reactants was the same and only the solvent varied. Reaction conditions included mixing 25 µL Na$^{19}F$+20 µL AlCl$_3$+20 µL IMP-461±60 µL solvent, followed by heating at 101° C. for 5 min. Table 31 shows that the presence of a solvent does improve the yields of [Al$^{19}F$] IMP-461 (IMP 473) considerably.

TABLE 31

$^{19}F$ labeling of IMP 461 in various solvents

| Solvent | H$_2$O | MeOH | EtOH | CH$_3$CN |
|---|---|---|---|---|
| Al-IMP-461 | 2.97 | 3.03 | 2.13 | 1.54 |
| IMP-465 | 52.46 | 34.19 | 31.58 | 24.58 |
| IMP-473 | 14.99 | 30.96 | 33.00 | 37.48 |
| IMP-473 | 15.96 | 31.81 | 33.29 | 36.40 |
| IMP-461 | 13.63 | — | — | — |

| Solvent | IPA | Acetone | THF | Dioxane |
|---|---|---|---|---|
| Al-IMP-461 | 2.02 | 2.05 | 2.20 | 16.67 |
| IMP-465 | 32.11 | 28.47 | 34.76 | 10.35 |
| IMP-473 | 27.31 | 34.35 | 29.38 | 27.09 |
| IMP-473 | 27.97 | 35.13 | 29.28 | 11.62 |
| IMP-461 | 10.58 | — | 4.37 | 34.27 |

| Solvent | DMF | DMSO | $t_R$ (min) |
|---|---|---|---|
| Al-IMP-461 | — | — | 9.739 |
| IMP-465 | 19.97 | 37.03 | 10.138 |
| IMP-473 | 27.77 | 31.67 | 11.729 |
| IMP-473 | 27.34 | 31.29 | 11.952 |
| IMP-461 | — | — | 12.535 |

[Al$^{19}F$] IMP 461 = IMP 473

RP-HPLC analysis: WATERS® 2695 HPLC system equipped with a PHENOMENEX® GEMINI™ C$_{18}$ reverse-phase column (4.6×250 mm, 5 µm, 110 Å), using a linear gradient of 100% A (0.1% TFA) to 90% A in 5 minutes, 90% A to 20% B (90% acetonitrile, 10% water, 0.1% TFA) in 16 minutes at a flow rate of 1 mL/min, absorbance was detected at 220 nm using WATERS® PDA 2996 detector. (Run time: 20 minutes)

Example 36

Elution of $^{18}F$ with Bicarbonate $^{18}F$, 10.43 mCi, was received in 2 mL in a syringe. The solution was passed through a SEP-PAK® Light, WATERS® ACCELL™ Plus QMA Cartridge. The column was then washed with 5 mL of DI water. The $^{18}F$ was eluted with 0.4 M KHCO$_3$ in fractions as shown below.

| Vial | Vol. Acetic acid µL | Vol. 0.4 M KHCO$_3$ µL | Activity mCi |
|---|---|---|---|
| 1 | 7.5 | 150 | 0.0208 |
| 2 | 10 | 200 | 7.06 |
| 3 | 5 | 100 | 1.653 |
| 4 | 25 | 500 | 0.548 |

The effects of the amount of additional solvent (CH$_3$CN) on $^{18}F$ labeling of IMP-461 was examined. In each case, the concentration of reactants was the same and only the amount of solvent varied. Reaction conditions included mixing 10 µL AlCl$_3$+20 µL $^{18}F$+20 µL IMP-461+CH$_3$CN followed by heating at 101° C. for 5 min. Table 32 shows that following an initial improvement the labeling efficiency decreases in the presence of excess solvent.

TABLE 32

$^{18}F$ labeling of IMP 461 using varying amounts of CH$_3$CN

| CH3CN (µL) | F-18 mCi | $t_R$ 2.70 min (%) | $t_R$ 8.70 min (%) | RCY % (HLB) |
|---|---|---|---|---|
| 0 | 0.642 | 13.48 | 86.52 | 50.7 |
| 100 | 0.645 | 1.55 | 98.45 | 81.8* |
| 200 | 0.642 | 2.85 | 97.15 | 80.8 |
| 400 | 0.645 | 14.51 | 85.49 | 57.8 |

*Aqueous wash contains labeled peptide. RCY = radiochemical yield after HLB purification Example 37

High Dose Radiolabeling of IMP 461

$^{18}F$, 163 mCi, was received in 2 mL in a syringe. The solution was passed through a SEP-PAK® Light, WATERS® ACCELL™ Plus QMA Cartridge. The column was then washed with 5 mL of DI water. The $^{18}F$ was eluted with 0.4 M K$_2$CO$_3$ in fractions as shown in Table 33.

TABLE 33

High Dose Labeling

| Vial | Vol. Acetic acid µL | Vol. 0.4 M K$_2$CO$_3$ µL | Activity mCi |
|---|---|---|---|
| 1 | 18.5 | 185 | 5.59 |
| 2 | 5 | 50 | 35.8 |
| 3 | 5 | 50 | 59.9 |
| 4 | 5 | 50 | 20.5 |
| 5 | 5 | 50 | 5.58 |
| 6 | 50 | 500 | 4.21 |

An aluminum chloride solution (10 µL, 2 mM in pH 4, 2 mM NaOAc) was added to vial number 3 from Table 33. The peptide (20 µL, 2 mM in pH 4, 2 mM NaOAc) was added to the vial followed by the addition of 170 µL of CH$_3$CN. The solution was heated for 10 min at 103° C. the diluted with 6 mL of water. The solution was pulled into a 10 mL syringe and injected onto two WATERS® HLB Plus Cartridges arranged in tandem. The cartridges were washed with 8 mL water. The radiolabeled peptide Al[18]F IMP 461 was then eluted with 10 mL 1:1 EtOH/H$_2$O, 30.3 mCi, 63.5% yield, specific activity 750 Ci/mmol.

The labeled peptide was free of unbound $^{18}$F by HPLC. The total reaction and purification time was 20 min.

Example 38

Preparation of [19]F Labeled Peptides

Products containing [27]Al and/or $^{19}$F are useful for certain applications like NMR imaging. An improved method for preparing [Al[19]F] labeled compounds was developed. IMP 461 was prepared as described in Example 15 and labeled with [19]F. Reacting IMP 461 with AlCl$_3$+NaF resulted in the formation of three products (not shown). However, by reacting IMP 461 with AlF$_3$.3H$_2$O we obtained a higher yield of [Al[19]F] IMP 461.

Synthesis of IMP 473: ([Al[19]F] IMP 461) To (14.1 mg, 10.90 μmol) IMP 461 in 2 mL NaOAc (2 mM, pH 4.18) solution added (4.51 mg, 32.68 μmol) AlF$_3$.3H$_2$O and 500 μL ethanol. The pH of the solution to adjusted to 4.46 using 3 μL 1 N NaOH and heated in a boiling water bath for 30 minutes. The crude reaction mixture was purified by preparative RP-HPLC to yield 4.8 mg (32.9%) of IMP 473. HRMS (ESI-TOF) MH$^+$ expected 1337.6341; found 1337.6332

WATERS® 2695 HPLC system equipped with a PHENOMENEX® GEMINI™ C$_{18}$ reverse-phase column (4.6×250 mm, 5 μm, 110 Å), using a linear gradient of 100% A (0.1% TFA) to 20% B (90% acetonitrile, 10% water, 0.1% TFA) in 20 minutes at a flow rate of 1 mL/min, absorbance was detected at 220 nm using WATERS® PDA 2996 detector. Two closely eluting peaks were observed on analytical RP-HPLC, indicating the presence of diastereomers as observed for other [Al[18]F] labeled peptides.

These results demonstrate that $^{19}$F labeled molecules may be prepared by forming metal-$^{19}$F complexes and binding the metal-$^{19}$F to a chelating moiety, as discussed above for $^{18}$F labeling. The instant Example shows that a targeting peptide of use for pretargeting detection, diagnosis and/or imaging may be prepared using the instant methods.

Example 39

Other Prosthetic Group Labeling Methods Using A $^{18}$F or Al[19]F

In certain embodiments, the aluminum fluoride labeling method may be performed using prosthetic group labeling methods for molecules that are sensitive to heat. Prosthetic group conjugation may be carried out at lower temperatures for heat-sensitive molecules.

The prosthetic group NOTA is labeled with $^{18}$F or $^{19}$F as described above and then it is attached to the targeting molecule. In one non-limiting example, this is performed with an aldehyde NOTA that is then attached to an amino-oxy compound on a targeting molecule. Alternatively an amino-oxy maleimide is reacted with the aldehyde and then the maleimide is attached to a cysteine on a targeting molecule (Toyokuni et al., 2003, Bioconj Chem 14:1253).

In another alternative, the AlF-chelator complexes are attached to targeting molecules through click chemistry. The ligands are first labeled with Al[18]F or Al $^{19}$F as discussed above. The AlF-chelator is then conjugated to a targeting molecule through click chemistry as disclosed below. For example, an alkyne NOTA is labeled according to Marik and Stucliffe (2006, Tetrahedron Lett 47:6681) and conjugated to an azide containing targeting agent.

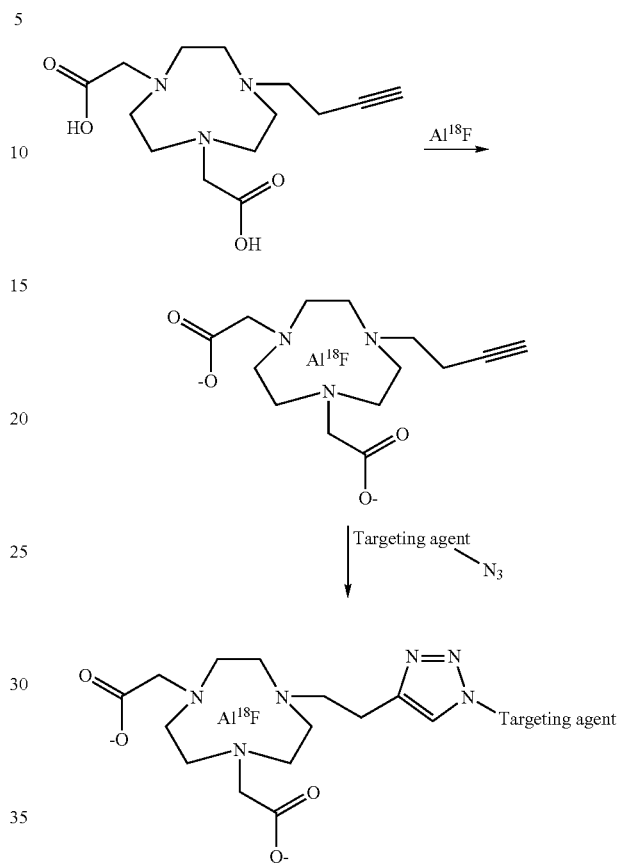

In another alternative embodiment, the azide is on the chelator moiety and the alkyne is on the targeting agent (Glaser and Arstad, 2007, Bioconj Chem 18:989).

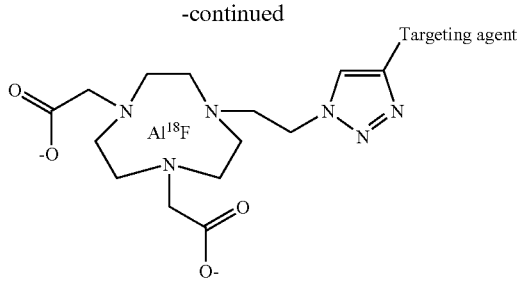

What is claimed is:

1. A method of labeling a molecule with $^{18}$F comprising:
   a) reacting the $^{18}$F with a group IIIA metal to form a metal-$^{18}$F complex; and
   b) attaching the metal-$^{18}$F complex to a molecule to form one or more $^{18}$F-labeled molecules to be administered to a subject.

2. The method of claim 1, wherein the metal-$^{18}$F complex attaches to a chelating moiety on the molecule.

3. The method of claim 1, wherein the molecule is a protein or peptide.

4. The method of claim 1, wherein the metal is selected from the group consisting of aluminum, gallium, indium, and thallium.

5. The method of claim 1, wherein the $^{18}$F-labeled molecule is stable in serum for at least 4 hours.

6. The method of claim 2, wherein the chelating moiety is selected from the group consisting of DOTA, TETA, NOTA, NETA, C-NETA, L-NETA, S-NETA or an iminodiacetic acid derivative of NOTA wherein the iminodiacetic acid is attached to a ring nitrogen or carbon atom of NOTA.

7. The method of claim 3, wherein the peptide is selected from the group consisting of
   IMP 449 (NOTA-ITC benzyl-D-Ala-D-Lys(HSG)-D-Tyr-D-Lys(HSG)-NH$_2$);
   IMP 460 (NODA-Ga-D-Ala-D-Lys(HSG)-D-Tyr-D-Lys(HSG)-NH$_2$;
   IMP 461 (NOTA-D-Ala-D-Lys(HSG)-D-Tyr-D-Lys(HSG)-NH$_2$);
   IMP 462 (NOTA-D-Asp-D-Lys(HSG)-D-Tyr-D-Lys(HSG)-NH$_2$);
   IMP 465 (NOTA-D-Ala-D-Lys(HSG)-D-Tyr-D-Lys(HSG)-NH$_2$);
   IMP 466 (NOTA-D-Phe-Cys-Phe-D-Trp-Lys-Thr-Cys-Thro1);
   IMP 467 (C-NETA-succinyl-D-Lys(HSG)-D-Tyr-D-Lys(HSG)-NH$_2$);
   IMP 468 (NOTA-NH—(CH$_2$)$_7$CO-Gln-Trp-Val-Trp-Ala-Val-Gly-His-Leu-Met-NH$_2$; SEQ ID NO:20);
   IMP 469 (S-NETA-D-Lys(HSG)-D-Tyr-D-Lys(HSG)-NH$_2$) and
   IMP 470 (L-NETA-succinyl-D-Lys(HSG)-D-Tyr-D-Lys(HSG)-NH$_2$).

8. The method of claim 1, further comprising administering the $^{18}$F-labeled molecules to a subject without separating the $^{18}$F-labeled molecule from unlabeled molecules.

9. The method of claim 1, further comprising:
   c) separating the $^{18}$F-labeled molecules from unlabeled molecules to produce purified $^{18}$F-labeled molecules; and
   d) administering the purified $^{18}$F-labeled molecules to a subject.

10. The method of claim 9, wherein the purified $^{18}$F-labeled molecules are produced in less than one hour from the start of the method.

11. The method of claim 1, wherein the metal is aluminum.

12. The method of claim 2, wherein the metal-$^{18}$F complex is attached to the chelating moiety by heating in aqueous medium at a temperature of between 95° C. and 110° C.

13. The method of claim 12, wherein an organic solvent is added to the aqueous medium.

14. The method of claim 2, wherein the metal-$^{18}$F complex is attached to the chelating moiety by microwave irradiation.

15. A method of labeling a molecule with $^{18}$F comprising:
   a) adding $^{18}$F to a group IIIA metal-complexed molecule; and
   b) allowing the $^{18}$F to bind to the group IIIA metal.

16. The method of claim 15, wherein the metal is attached to a chelating moiety that is conjugated to the molecule.

17. A method of labeling a molecule with $^{19}$F comprising:
   a) reacting the $^{19}$F with a group IIIA metal to form a group IIIA metal-$^{19}$F complex; and
   b) attaching the group IIIA metal-$^{19}$F complex to a molecule to form one or more $^{19}$F-labeled molecules to be administered to a subject.

18. The method of claim 17, wherein the complex attaches to a chelating moiety on the molecule.

19. The method of claim 17, wherein the molecule is a protein or peptide.

20. The method of claim 17, wherein the metal is selected from the group consisting of aluminum, gallium, indium and thallium.

21. The method of claim 17, wherein the $^{19}$F labeled molecule is stable in serum for at least 4 hours.

22. The method of claim 18, wherein the chelating moiety is selected from the group consisting of DOTA, TETA, NOTA, NETA, C-NETA, L-NETA, S-NETA or an iminodiacetic acid derivative of NOTA; wherein the iminodiacetic acid is attached to a ring nitrogen or carbon atom of NOTA.

23. The method of claim 19, wherein the peptide is selected from the group consisting of
   IMP 449 (NOTA-ITC benzyl-D-Ala-D-Lys(HSG)-D-Tyr-D-Lys(HSG)-NH$_2$);
   IMP 460 (NODA-Ga-D-Ala-D-Lys(HSG)-D-Tyr-D-Lys(HSG)-NH$_2$;
   IMP 461 (NOTA-D-Ala-D-Lys(HSG)-D-Tyr-D-Lys(HSG)-NH$_2$);
   IMP 462 (NOTA-D-Asp-D-Lys(HSG)-D-Tyr-D-Lys(HSG)-NH$_2$);
   IMP 465 (NOTA-D-Ala-D-Lys(HSG)-D-Tyr-D-Lys(HSG)-NH$_2$);
   IMP 466 (NOTA-D-Phe-Cys-Phe-D-Trp-Lys-Thr-Cys-Thro1);
   IMP 467 (C-NETA-succinyl-D-Lys(HSG)-D-Tyr-D-Lys(HSG)-NH$_2$);
   IMP 468 (NOTA-NH—(CH$_2$)$_7$CO-Gln-Trp-Val-Trp-Ala-Val-Gly-His-Leu-Met-NH$_2$; SEQ ID NO:20);
   IMP 469 (S-NETA-D-Lys(HSG)-D-Tyr-D-Lys(HSG)-NH$_2$) and
   IMP 470 (L-NETA-succinyl-D-Lys(HSG)-D-Tyr-D-Lys(HSG)-NH$_2$).

24. The method of claim 17, further comprising administering the $^{19}$F-labeled molecules to a subject without separating the $^{19}$F-labeled molecule from unlabeled molecules.

25. The method of claim 17, further comprising:
   c) separating the $^{19}$F-labeled molecules from unlabeled molecules to produce purified $^{19}$F-labeled molecules; and
   d) administering the purified $^{19}$F-labeled molecules to a subject.

26. The method of claim 25, wherein the purified $^{19}$F-labeled molecules are produced in less than one hour from the start of the method.

27. The method of claim 17, wherein the metal is aluminum.

* * * * *